(12) United States Patent
Lo et al.

(10) Patent No.: US 11,435,339 B2
(45) Date of Patent: Sep. 6, 2022

(54) ANALYSIS OF CELL-FREE DNA IN URINE

(71) Applicant: The Chinese University of Hong Kong, Shatin (HK)

(72) Inventors: Yuk-Ming Dennis Lo, Hong Kong (CN); Rossa Wai Kwun Chiu, Hong Kong (CN); Kwan Chee Chan, Hong Kong (CN); Peiyong Jiang, Hong Kong (CN); Hua Tse Timothy Cheng, Hong Kong (CN)

(73) Assignee: The Chinese University of Hong Kong, Shatin (HK)

( * ) Notice: Subject to any disclaimer, the term of this patent is extended or adjusted under 35 U.S.C. 154(b) by 343 days.

(21) Appl. No.: 15/827,565

(22) Filed: Nov. 30, 2017

(65) Prior Publication Data

US 2018/0149636 A1 May 31, 2018

Related U.S. Application Data

(60) Provisional application No. 62/427,999, filed on Nov. 30, 2016.

(51) Int. Cl.
*G01N 33/493* (2006.01)
*C12Q 1/6806* (2018.01)
(Continued)

(52) U.S. Cl.
CPC ......... *G01N 33/493* (2013.01); *C12Q 1/6806* (2013.01); *C12Q 1/6827* (2013.01); *C12Q 1/6886* (2013.01); *C12Q 2600/154* (2013.01)

(58) Field of Classification Search
None
See application file for complete search history.

(56) References Cited

U.S. PATENT DOCUMENTS

| 6,773,897 B2 | 8/2004 | Herman et al. |
| 7,749,702 B2 | 7/2010 | Lofton-Day et al. |

(Continued)

FOREIGN PATENT DOCUMENTS

| CN | 102021233 | 4/2011 |
| CN | 102105586 | 6/2011 |

(Continued)

OTHER PUBLICATIONS

Lichtenstein, Anatoly V., et al. "Novel applications of polymerase chain reaction to urinary nucleic acid analysis." Clinical Applications of PCR. Humana Press, 2006. 145-154. (Year: 2006).*

(Continued)

*Primary Examiner* — Olivia M. Wise
(74) *Attorney, Agent, or Firm* — Kilpatrick Townsend & Stockton LLP

(57) ABSTRACT

Diseases (e.g., cancer) of a particular organ can be detected by analyzing cell-free DNA. Some embodiments may use an organ-associated sample that is from a particular organ or passes through the particular organ, as may occur, for example, in urine, saliva, blood, and stool samples. In some embodiments, methylation levels of cell-free DNA can be measured in a sample. Tissue-specific methylation patterns can be used to determine fractional contributions from different tissue types. In other embodiments, sizes of organ-associated cell-free DNA can be measured. A statistical measure of the size profile may indicate that cell-free DNA fragments are collectively longer than expected for subjects with healthy tissue compared to non-healthy tissue. In other embodiments, two different samples can be analyzed to determine whether a particular organ has cancer. Cell-free DNA in a blood sample and organ-associated sample can both be analyzed to identify chromosomal regions exhibiting a copy number aberration.

24 Claims, 46 Drawing Sheets
(22 of 46 Drawing Sheet(s) Filed in Color)

(51) Int. Cl.
  *C12Q 1/6827* (2018.01)
  *C12Q 1/6886* (2018.01)

(56) References Cited

U.S. PATENT DOCUMENTS

| | | | |
|---|---|---|---|
| 7,803,929 | B2 | 9/2010 | Melkonyan et al. |
| 7,899,626 | B2 | 3/2011 | Kruglyak et al. |
| 7,914,982 | B2 | 3/2011 | Melkonyan et al. |
| 7,973,154 | B2 | 7/2011 | Melkonyan et al. |
| 8,150,626 | B2 | 4/2012 | Fan et al. |
| 8,383,335 | B2 | 2/2013 | Melkonyan et al. |
| 8,455,190 | B2 | 6/2013 | Makrigiorgos |
| 8,486,626 | B2 | 7/2013 | Umansky et al. |
| RE44,596 | E | 11/2013 | Stroun et al. |
| 8,642,261 | B2 | 2/2014 | Melkonyan et al. |
| 8,712,697 | B2 | 4/2014 | Struble et al. |
| 8,741,811 | B2 | 6/2014 | Lo et al. |
| 8,822,155 | B2 | 9/2014 | Sukumar et al. |
| 8,927,209 | B2 | 1/2015 | Hamamoto et al. |
| 9,121,069 | B2 | 9/2015 | Lo et al. |
| 9,163,229 | B2 | 10/2015 | Melkonyan et al. |
| 9,183,349 | B2 | 11/2015 | Kupershmidt et al. |
| 9,222,137 | B2 | 12/2015 | Tiacci et al. |
| 9,260,745 | B2 | 2/2016 | Rava et al. |
| 9,290,803 | B2 | 3/2016 | Laird et al. |
| 9,292,660 | B2 | 3/2016 | Von Hoff et al. |
| 9,361,426 | B2 | 6/2016 | Akmaev et al. |
| 9,453,265 | B2 | 9/2016 | Umansky et al. |
| 9,598,731 | B2 | 3/2017 | Talasaz |
| 9,732,390 | B2 | 8/2017 | Lo et al. |
| 9,758,814 | B2 | 9/2017 | Fehr et al. |
| 9,834,822 | B2 | 12/2017 | Talasaz |
| 9,840,743 | B2 | 12/2017 | Talasaz |
| 9,902,992 | B2 | 2/2018 | Talasaz et al. |
| 2005/0221314 | A1 | 10/2005 | Berlin et al. |
| 2007/0141582 | A1 | 6/2007 | Li et al. |
| 2008/0081338 | A1 | 4/2008 | Lo et al. |
| 2009/0280479 | A1 | 11/2009 | Hoon et al. |
| 2010/0068720 | A1 | 3/2010 | Li et al. |
| 2011/0028333 | A1 | 2/2011 | Christensen et al. |
| 2011/0171647 | A1 | 7/2011 | Tomigahara et al. |
| 2012/0003636 | A1 | 1/2012 | Lo et al. |
| 2012/0041683 | A1 | 2/2012 | Vaske et al. |
| 2012/0221249 | A1 | 8/2012 | Lizardi et al. |
| 2013/0085681 | A1 | 4/2013 | Deciu et al. |
| 2014/0045181 | A1 | 2/2014 | Lo et al. |
| 2014/0080715 | A1 | 3/2014 | Lo et al. |
| 2014/0100121 | A1 | 4/2014 | Lo et al. |
| 2014/0178348 | A1 | 6/2014 | Kelsey et al. |
| 2014/0256574 | A1 | 9/2014 | Herold et al. |
| 2014/0274740 | A1 | 9/2014 | Srinivasan et al. |
| 2014/0274752 | A1 | 9/2014 | Blume et al. |
| 2014/0274767 | A1 | 9/2014 | Yegnasubramanian et al. |
| 2014/0357497 | A1 | 12/2014 | Zhang et al. |
| 2015/0197785 | A1 | 7/2015 | Carter et al. |
| 2015/0211070 | A1 | 7/2015 | Seligson et al. |
| 2015/0322513 | A1 | 11/2015 | Gromminger et al. |
| 2015/0344970 | A1 | 12/2015 | Vogelstein et al. |
| 2015/0368708 | A1 | 12/2015 | Talasaz |
| 2015/0376700 | A1 | 12/2015 | Schnall-Levin et al. |
| 2016/0002739 | A1 | 1/2016 | Schütz et al. |
| 2016/0017419 | A1 | 1/2016 | Chiu et al. |
| 2016/0017430 | A1 | 1/2016 | Badosa |
| 2016/0040229 | A1 | 2/2016 | Talasaz et al. |
| 2016/0046979 | A1 | 2/2016 | Leamon et al. |
| 2016/0160288 | A1 | 6/2016 | Pan et al. |
| 2016/0168643 | A1 | 6/2016 | Ahlquist et al. |
| 2016/0168648 | A1 | 6/2016 | Allawi et al. |
| 2016/0201142 | A1 | 7/2016 | Lo et al. |
| 2016/0210403 | A1 | 7/2016 | Zhang et al. |
| 2016/0232290 | A1 | 8/2016 | Rava et al. |
| 2016/0239604 | A1 | 8/2016 | Chudova et al. |
| 2016/0251704 | A1 | 9/2016 | Talasaz et al. |
| 2016/0275239 | A1 | 9/2016 | Devogelaere et al. |
| 2016/0298183 | A1 | 10/2016 | Wen et al. |
| 2016/0304936 | A1 | 10/2016 | Ji et al. |
| 2016/0326593 | A1 | 11/2016 | Clement et al. |
| 2016/0333417 | A1 | 11/2016 | Talasaz |
| 2016/0340740 | A1 | 11/2016 | Zhang |
| 2017/0016054 | A1 | 1/2017 | Southern et al. |
| 2017/0024513 | A1 | 1/2017 | Lo et al. |
| 2017/0029900 | A1 | 2/2017 | Lo et al. |
| 2017/0073774 | A1 | 3/2017 | Lo et al. |
| 2017/0101685 | A1 | 4/2017 | Lo et al. |
| 2017/0107576 | A1 | 4/2017 | Babiarz et al. |
| 2017/0121767 | A1 | 5/2017 | Dor et al. |
| 2017/0211143 | A1 | 7/2017 | Shendure et al. |
| 2017/0233829 | A1 | 8/2017 | Lo et al. |
| 2017/0249421 | A1 | 8/2017 | Eberle et al. |
| 2017/0260590 | A1 | 9/2017 | Eltoukhy et al. |
| 2017/0342500 | A1 | 11/2017 | Marquard et al. |
| 2017/0349948 | A1 | 12/2017 | Lo et al. |
| 2017/0362638 | A1 | 12/2017 | Chudova et al. |
| 2018/0023125 | A1 | 1/2018 | Talasaz et al. |
| 2018/0119230 | A1 | 5/2018 | Velculescu et al. |

FOREIGN PATENT DOCUMENTS

| | | |
|---|---|---|
| CN | 103902809 | 7/2014 |
| EP | 1342794 A1 | 9/2003 |
| EP | 2771483 | 9/2014 |
| EP | 2893040 | 7/2015 |
| EP | 2997159 | 3/2016 |
| EP | 3018213 | 5/2016 |
| EP | 3194612 | 7/2017 |
| JP | 2013143946 | 7/2013 |
| TW | 201418474 | 5/2014 |
| WO | 2005019477 | 3/2005 |
| WO | 2005118852 | 12/2005 |
| WO | 2006128192 | 11/2006 |
| WO | 2008038000 | 4/2008 |
| WO | 2009013492 | 1/2009 |
| WO | 2011038507 | 4/2011 |
| WO | 2011130751 | 10/2011 |
| WO | 2012031329 | 3/2012 |
| WO | 2012/071621 A1 | 6/2012 |
| WO | 2012/103031 A2 | 8/2012 |
| WO | 2012012703 | 10/2012 |
| WO | 2013/045432 A1 | 4/2013 |
| WO | 2013052907 | 4/2013 |
| WO | 2013060762 | 5/2013 |
| WO | 2013066641 | 5/2013 |
| WO | 2014/043763 A1 | 3/2014 |
| WO | 2014039556 | 3/2014 |
| WO | 2014184199 | 11/2014 |
| WO | 2015116837 | 8/2015 |
| WO | 2015159292 | 10/2015 |
| WO | 2015/169947 A1 | 11/2015 |
| WO | 2015159292 | 12/2015 |
| WO | 2016/008451 A1 | 1/2016 |
| WO | 2016028316 | 2/2016 |
| WO | 2016097251 | 6/2016 |
| WO | 2016101258 | 6/2016 |
| WO | 2016/112850 A1 | 7/2016 |
| WO | 2016127844 | 8/2016 |
| WO | 2016183106 | 11/2016 |
| WO | 2016189288 | 12/2016 |

OTHER PUBLICATIONS

Yong et al. Profiling genome-wide DNA methylation. Epigenetics & Chromatin Jun. 29, 2016, vol. 9, No. 26, pp. 1-16 (Year: 2016).*
Beermann et al. Methods for Separate Isolation of Cell-Free DNA and CEllular DNA from Urine—Application of Methylation-Specific PCR on both DNA Fractions. The Open Biomarkers Journal 2011, vo. 4, pp. 15-17 (Year: 2011).*
Kim et al. Epigenetic biomarkers in urothelial bladder cancer. Expert Rev. Mol. Diagn. 2009, vol. 9, No. 3, pp. 259-269 (Year: 2009).*
How Kit et al. DNA methylation based biomarkers: Practical considerations and applications. Biochimie 2012, vol. 94, pp. 2314-2337 (Year: 2012).*

(56) References Cited

OTHER PUBLICATIONS

Bryzgunova et al. Extracellular Nucleic Acids in Urine: Sources, Structure, Diagnostic Potential. Acta Naturae 2015, vol. 7, No. 3, pp. 48-54 (Year: 2015).*
Ilumina. Infinium HD Assay Methylation Protocol Guide Nov. 2015, pp. 1-244 (Year: 2015).*
Sharma et al. Diagnosis and Treatment of Bladder Cancer. American Family Physician 2009, vol. 80, No. 1, pp. 718-723 (Year: 2009).*
International Search Report and Written Opinion from PCT/CN2017/113813 dated Nov. 30, 2017, 13 pages.
Stroun, et al., "The Origin and Mechanism of Circulating DNA," Annals New York Academy of Sciences 2000, 906, 161-168.
Lo, et al., "Presence of Fetal DNA in Maternal Plasma and Serum," Lancet 1997, 350, 485-87.
Chen, et al., "Microsatellite Alterations in Plasma DNA of Small Cell Lung Cancer Patients," Nature Medicine, 1996, vol. 2, No. 9, 1033-1035.
Lo, et al., "Presence of Donor-Specific DNA in Plasma of Kidney and Liver-Transplant Recipients," Lancet 1998, vol. 351, 1329-1330.
Chiu, et al., "Noninvasive Prenatal Diagnosis of Fetal Chromosomal Aneuploidy By Massively Parallel Genomic Sequencing of DNA in Maternal Plasma," PNAS 2009, vol. 105, No. 51, 20458-20463.
Leary, et al., "Detection of Chromosomal Alterations in the Circulation of Cancer Patients with Whole-Genome Sequencing," Science Translational Medicine 2012, vol. 4, Issue 162, 1-14.
Hung, et al., "Presence of Donor-Derived DNA and Cells in the Urine of Sex-Mismatched Hematopoietic Stem Cell Transplant Recipients: Implication for the Transrenal Hypothesis," Clinical Chemistry 2009, 55:4, 715-722.
Botezatu, et al., "Genetic Analysis of DNA Excreted in Urine: A New Approach for Detecting Specific Genomic DNA Sequences from Cells Dying in an Organism," Clinical Chemistry 2000, 46:8, 1078-1084.
Togneri et al., "Genomic Complexity of Urothelial Bladder Cancer Revealed in Urinary cfDNA," European Journal of Human Genetics 2016, 24, 1167-1174.
Patel, et al., "Association of Plasma and Urinary Mutant DNA with Clinical Outcomes in Muscle Invasive Bladder Cancer," 2017, 7:5554, 1-12.
Chan, et al., "Noninvasive Detection of Cancer-Associated Genome-Wide Hypomethylation and Copy Number Aberrations By Plasma DNA Bisulfite Sequencing," PNAS 2013, 110:47, 18761-18768.
De Vlaminck, et al., "Circulating Cell-Free DNA Enables Noninvasive Diagnosis of Heart Transplant Rejection," Science Translational Medicine 2014, 6:241, 1-9.
Al-Yatama, et al., "Detection of Y Chromosome-Specific DNA in the Plasma and Urine of Pregnant Women Using Nested Polymerase Chain Reaction," Prenatal Diagnosis 2001, 21, 399-402.
Tsui, et al., "High Resolution Size Analysis of Fetal DNA in the Urine of Pregnant Women by Paired-End Massively Parallel Sequencing," PLOS ONE 2012, 7:10, 1-7.
Su, et al., "Detection of Mutated K-ras DNA in Urine, Plasma, and Serum of Patients with Colorectal Carcinoma or Adenomatous Polyps," Ann. N.Y. Acad. Sci. 2008, 1137, 197-206.
Chan, et al., "Quantitative Analysis of the Transrenal Excretion of Circulating EBV DNA in Nasopharyngeal Carcinoma Patients," Clin Cancer Res 2008, 14(15), 4809-4813.
Zhang, et al., "Presence of Donor- and Recipient-derived DNA in Cell-free Urine Samples of Renal Transplantation Recipients: Urinary DNA Chimerism," Clinical Chemistry 1999, 45:10, 1741-1746.
Szarvas, et al., "Deletion Analysis of Tumor and Urinary DNA to Detect Bladder Cancer: Urine Supernatant Versus Urine Sediment," Oncology Reports 2007, 18, 405-409.
Birkenkamp-Demtroder, et al., "Genomic Alterations in Liquid Biopsies from Patients with Bladder Cancer," European Urology 2016, 70, 75-82.
Li, et al., "Inability to Detect Cell Free Fetal DNA in the Urine of Normal Pregnant Women nor in Those Affected by Preeclampsia Associated HELLP Syndrome," J Soc Gynecol Investig 2003, 10:8, 503-508.
Fernandez, et al., "A DNA Methylation Fingerprint of 1,628 Human Samples," Genome Res 2011, 1-38.
Kundaje, et al., "Integrative Analysis of 111 Reference Human Epigenomes," Nature 2015, 518, 317-330.
Houseman, et al., "DNA Methylation Arrays as Surrogate Measures of Cell Mixture Distribution," BMC Bioinformatics 2012, 13:86, 1-16.
Sun, et al., "Plasma DNA Tissue Mapping By Genome-Wide Methylation Sequencing for Noninvasive Prenatal, Cancer, and Transplantation Assessments," PNAS 2015, E5503-E5512.
Yu, et al., "High-Resolution Profiling of Fetal DNA Clearance from Maternal Plasma by Massively Parallel Sequencing," Clinical Chemistry 2013, 59:8, 1-10.
Chan, et al., "Cancer Genome Scanning in Plasma: Detection of Tumor-Associated Copy Number Aberrations, Single-Nucleotide Variants, and Tumoral Heterogeneity by Massively Parallel Sequencing," Clinical Chemistry 2013, 59:1, 211-224.
Lun, et al., "Noninvasive Prenatal Methylomic Analysis by Genomewide Bisulfite Sequencing of Maternal Plasma DNA," Clinical Chemistry 2013, 59:11, 1583-1594.
Jiang, et al., "Methy-Pipe: An Integrated Bioinformatics Pipeline for Whole Genome Bisulfite Sequencing Data Analysis," PLOS ONE 2014, 9:6, 1-11.
Lui, et al., "Predominant Hematopoietic Origin of Cell-Free DNA in Plasma and Serum After Sex-Mismatched Bone Marrow Transplantation," Clinical Chemistry 2002, 48:3, 421-427.
Hodges, et al., "Directional DNA Methylation Changes and Complex Intermediate States Accompany Lineage Specificity in the Adult Hematopoietic Compartment," Molecular Cell 2011, 44, 17-28.
Ito, et al., "Human Urine DNase I: Immunological Identity with Human Pancreatic DNase I, and Enzymic and Proteochemical Properties of the Enzyme," J. Biochem. 1984, 95, 1399-1406.
Nadano, et al., "Measurement of Deoxyribonuclease I Activity in Human Tissues and Body Fluids by a Single Radial Enzyme-Diffusion Method," Clin. Chem. 1993, 39:3, 448-452.
Jiang, et al., "Lengthening and Shortening of Plasma DNA in Hepatocellular Carcinoma Patients," PNAS 2015, E1317-E1325.
Underhill, et al., "Fragment Length of Circulating Tumor DNA," PLOS Genetics 2016, 12:7, 1-24.
Feinberg, et al., "Hypomethylation Distinguishes Genes of Some Human Cancers From Their Normal Counterparts," Nature 1983, 301, 89-92.
Beroukhim, et al., "The Landscape of Somatic Copy-Number Alteration Across Human Cancers," Nature 2010, 463, 899-906.
Krzywinski, et al., "Circos: An Information Aesthetic for Comparative Genomics," Genome Research 2009, 19, 1639-1645.
Lo, et al., "Maternal Plasma DNA Sequencing Reveals the Genome-Wide Genetic and Mutational Profile of the Fetus," Science Translational Medicine 2010, 2:61, 1-13.
Snyder, et al., "Cell-free DNA Comprises an In Vivo Nucleosome Footprint that Informs Its Tissues-Of-Origin," Cell 2016, 164, 57-68.
The Cancer Genome Atlas Research Network, "Comprehensive Molecular Characterization of Urothelial Bladder Carcinoma," Nature 2014, 507, 315-322.
Van Den Meersche, et al., "xsample(): An R Function for Sampling Linear Inverse Problems," Journal of Statistical Software 2009, 30, 1-15.
Non-Final Office Action dated Jun. 12, 2018 in U.S. Appl. No. 14/803,692, filed Jul. 20, 2015. 21 pages.
Gil, M.M. et al.; "Analysis of cell-free DNA in maternal blood in screening for fetal aneuploidies: updated meta-analysis"; Ultrasound in Obstetrics & Gynecology; 2015 (published online Feb. 1, 2015); vol. 45, Issue 3; pp. 249-266.
Houseman, Eugene Andres et al.; "Reference-free cell mixture adjustments in analysis of DNA methylation data"; Bioinformatics; Advance Access publication Jan. 21, 2014; vol. 30, No. 10; pp. 1431-1439.

(56) References Cited

OTHER PUBLICATIONS

Non-Final Office Action dated Mar. 26, 2019 in U.S. Appl. No. 14/803,692, filed Jul. 20, 2015. 17 pages.
Wong, Ada I.C. et al.; "Noninvasive fetal genomic, methylomic, and transcriptomic analyses using maternal plasma and clinical implications"; Trends in Molecular Medicine; Feb. 2015; vol. 21, No. 2; pp. 98-108.
Schwarzenbach, Heidi et al.; "Cell-free nucleic acids as biomarkers in cancer patients"; Nature Reviews Cancer; Jun. 2011; vol. 11, No. 6; pp. 426-437.
Extended European Search Report dated Jun. 21, 2019 in EP Patent Application No. 19171637.2. 8 pages.
Extended European Search Report dated May 28, 2020 in EP Patent Application No. 17875411.5. 11 pages.
Inoue., DNA Analysis Using Noninvasive Samples: Methods of Sample Collection, DNA Extraction, PCR Amplification and Kinship Analysis, Primate Research, vol. 31, 2015, pp. 3-18.
Accomando et al., Quantitative Reconstruction of Leukocyte Subsets Using DNA Methylation, Genome Biology, vol. 15, No. R50, 2014, 12 pages.
Avraham et al., Tissue Specific DNA Methylation in Normal Human Breast Epithelium and in Breast Cancer, PLoS One, vol. 9, No. 3, e91805, Mar. 2014, 8 pages.
Castellanos-Rizaldos, COLD-PCR Amplification of Bisulfite-Converted DNA Allows the Enrichment and Sequencing of Rare Un-Methylated Genomic Regions, PLoS One, vol. 9, No. 4, e94103, Apr. 2014, 5 pages.
Chu et al.. Chapter 12 Solving Linear Equations, An Introduction to Optimization, Spring 2014, Available online at: https://www.cs.ccu.edu.tw/-wtchu/courses/2015s_OPT/Lectures/Chapter%2012%20Solving%20Linear%20Equations.pdf (Year: 2014), 2014, pp. 1-47.
Guo et al., Identification of Methylation Haplotype Blocks Aids in Deconvolution of Heterogeneous Tissue Samples and Tumor Tissue-of-origin Mapping from Plasma DNA, Nature Genetics, vol. 49, No. 4, 2017, 21 pages.
Houseman et al., Cell-Composition Effects in the Analysis of DNA Methylation Array Data: A Mathematical Perspective, BMC Bioinformatics, vol. 16, No. 95, 2015, 16 pages.
Husseiny et al.. Development of a Quantitative Methylation-Specific Polymerase Chain Reaction Method for Monitoring Beta Cell Death in Type 1 Diabetes, PLoS One, vol. 7, No. 10; e47942, Oct. 2012, 11 pages.
Husseiny et al., Tissue-Specific Methylation of Human Insulin Gene and PCR Assay for Monitoring Beta Cell Death, PLoS One, vol. 9, No. 4, e94591, Apr. 2014, 9 pages.
Jin et al., Circulating Methylated DNA as Biomarkers for Cancer Detection, Chapter 6, Available online at: https://www.intechopen.com/books/methylationfrom-dna-rna-and-histones-to-diseases-and-treatmenUcirculating-methylated-dnaas-biomarkers-for-cancer-detection, Nov. 28, 2012, pp. 137-152.
Kit et al., DNA Methylation Based Biomarkers: Practical Considerations and Applications, Biochimie 2012, vol. 94, Jul. 27, 2012, pp. 2314-233.
Koh et al., Noninvasive in Vivo Monitoring of Tissue-Specific Global Gene Expression in Humans, PNAS, vol. 111, No. 20, plus of Supporting Information, May 20, 2014, pp. 7361-7366.
Lebastchi, Immune Therapy and B-Cell Death in Type 1 Diabetes, Diabetes, vol. 62, No. 5, May 2013, pp. 1676-1680.
Lee et al., Analyzing the Cancer Methylome Through Targeted Bisulfite Sequencing, Cancer Letters 2013, vol. 340, 2013, pp. 171-178.
Madi et al., The Determination of Tissue-Specific DNA Methylation Patterns in Forensic Biofluids Using Bisulfite Modification and Pyrosequencing, Electrophoresis, vol. 33, No. 12, Jul. 2012, pp. 1736-1745.
Miller et al., Read Depth: A Parallel R Package for Detecting Copy Number Alterations from Short Sequencing Reads, PLoS ONE, vol. 6, No. 1, e16327, Jan. 2011, pp. 1-7.
Page et al., Detection of HER2 Amplification in Circulating Free DNA in Patients with Breast Cancer, British Journal of Cancer, vol. 104, No. 8, Apr. 2011, pp. 1342-1348.
International Application No. PCT/CN2015/084442, International Preliminary Report on Patentability, dated Feb. 2, 2017, 6 pages.
International Application No. PCT/CN2015/084442, International Search Report and Written Opinion, dated Sep. 30, 2015, 11 pages.
Radpour et al., Hypermethylation of Tumor Suppressor Genes Involved in Critical Regulatory Pathways for Developing a Blood-Based Test in Breast Cancer, PLoS One, vol. 6, No. 1, e16080, Jan. 2011, pp. 1-11.
Shaw et al., Genomic Analysis of Circulating Cell-Free DNA Infers Breast Cancer Dormancy, Genome Research, vol. 22, No. 2, Feb. 2012, pp. 220-231.
Toyota et al., Identification of Differentially Methylated Sequences in Colorectal Cancer by Methylated CpG Island Amplification, Cancer Research, vol. 59, May 15, 1999, pp. 2307-2312.
Taiwan Application No. TW104123505, Office Action, dated Feb. 13, 2017, 7 pages.
Taiwan Application No. TW104123505, Office Action, dated Sep. 29, 2017, 9 pages.
Kang, Shuli et al.; "CancerLocator: non-invasive cancer diagnosis and tissue-of-origin prediction using methylation profiles of cell-free DNA"; Genome Biology; 2017; vol. 18, No. 53; 12 pages.
Extended European Search Report dated Aug. 12, 2021 in EP Patent Application No. 21174356.2. 9 pages.

\* cited by examiner

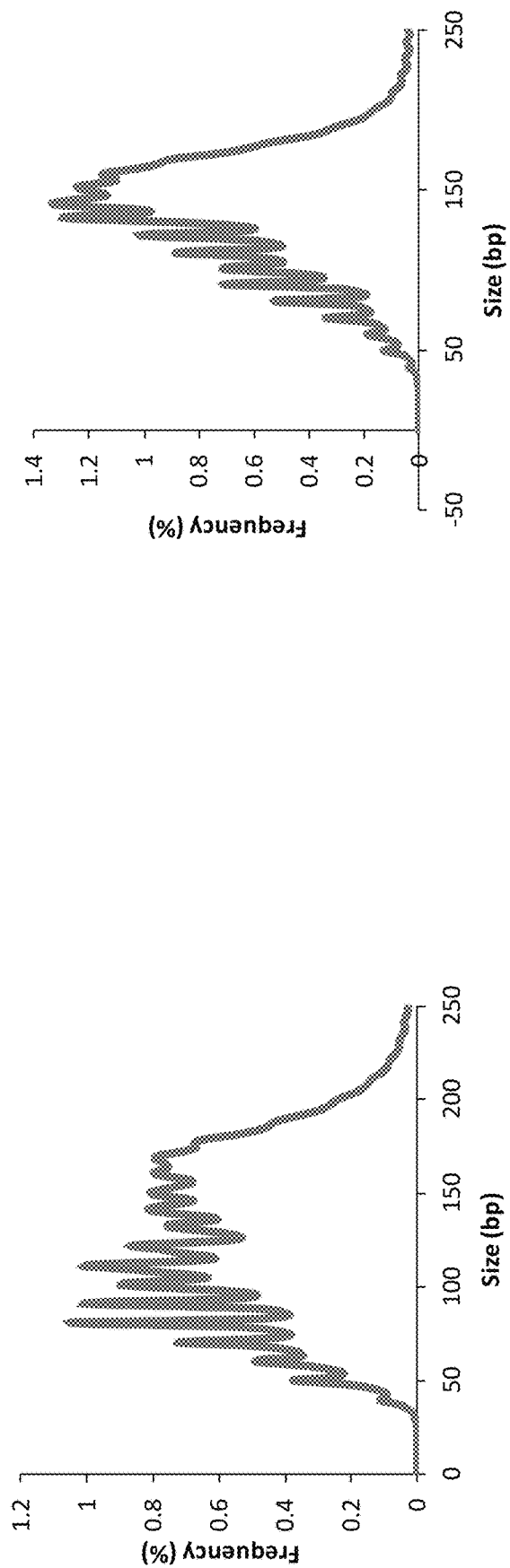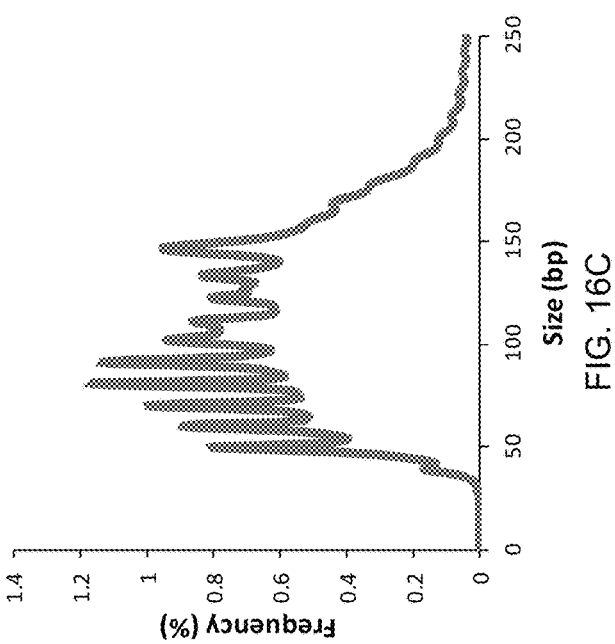
FIG. 16A
FIG. 16B
FIG. 16C

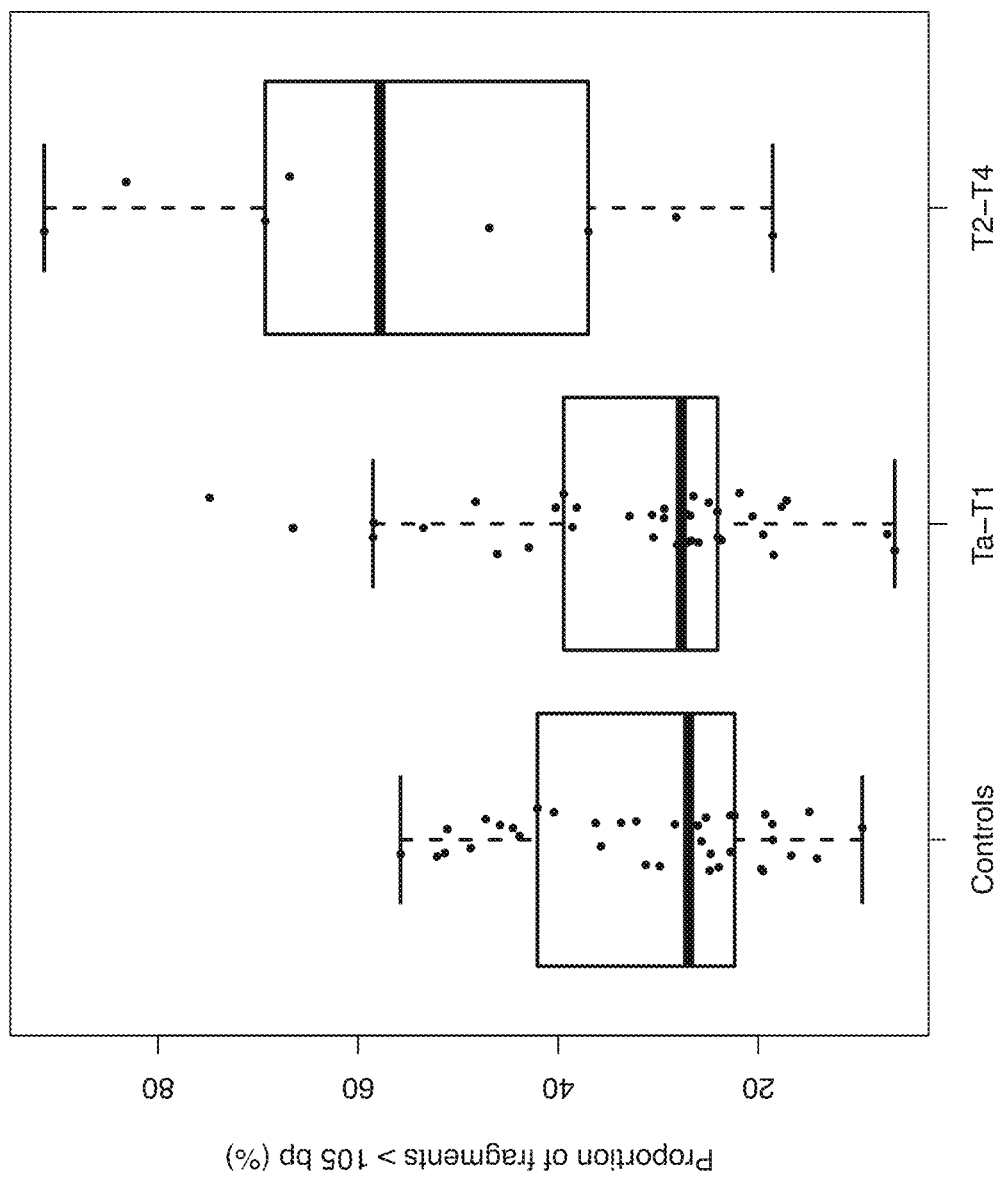

ANALYSIS OF CELL-FREE DNA IN URINE

CROSS REFERENCE TO RELATED APPLICATION

The present application claims priority from U.S. Provisional Application No. 62/427,999, entitled "Analysis of Cell-Free DNA in Urine and Other Samples" filed Nov. 30, 2016, the entire contents of which are herein incorporated by reference for all purposes.

BACKGROUND

Short fragments of extracellular DNA found in human body fluids are released during apoptosis and necrosis from dying cells (1). Analyses of cell-free (cf) DNA in circulating plasma originating from the fetus (2), tumor cells (3) and transplant allograft (4) have enabled the development of noninvasive prenatal testing (5), 'liquid biopsy' for assessing tumors (6,7), and the monitoring of the clinical status of transplanted organs (8).

Urine analysis is truly noninvasive and understanding the origin of urinary cfDNA is useful for guiding its clinical use as a form of 'liquid biopsy'. DNA isolated from the cell-free supernatant of urine can be broadly categorized as arising from the pre-renal, renal, or post-renal system. Using blood transfusion (9), pregnancy (9-11), hematopoietic stem cell transplantation (12), non-urologic malignancies (13,14), renal transplantation (15), and bladder cancer (16,17) as model systems, a number of groups have demonstrated that a proportion of urinary cfDNA is derived from the systemic circulation, the kidney, and from the post-renal urothelium.

Previous studies focus on detecting cfDNA from a single source of interest at a time, and there is a large variation in the quantity of urinary cfDNA derived from a particular source. The proportional contribution of each tissue source to the total urinary cfDNA is unknown, and in some studies, the concentration of cfDNA from the source of interest is extremely low, or even undetectable (15,16,18). Accordingly, it has been difficult to use urine (or non-invasive biopsies besides blood, such as saliva or stool samples) to detect cancer or other diseases.

Other techniques analyze point mutations for monitoring patients previously diagnosed with cancer. However, such techniques are not readily amendable to broadly applicable screening techniques of asymptomatic patients to diagnose cancer. The specific point mutations have to be identified before cancer can be detected. Thus, only screening for well-known point mutations is possible for screening, or the specific point mutations for a patient must be identified through previous invasive biopsied for a previously detector tumor.

BRIEF SUMMARY

Embodiments can analyze cell-free DNA for disease detection (e.g., cancer) of a particular organ. Some embodiments may use an organ-associated sample that is from a particular organ or passes through the particular organ, as may occur, for example, in urine, saliva, blood, and stool samples. The analysis may be performed in various ways.

In some embodiments, methylation levels of cell-free DNA can be measured in a sample. Tissue-specific methylation patterns can be used to determine fractional contributions from different tissue types. One tissue type can be a diseased tissue type of a particular disease of a particular organ. The fractional contribution of the diseased tissue type can be used to determine a level (classification) of the particular disease in the sample. As an example, methylation patterns can be used determine a percentage of cancerous bladder lining cells, and the percentage can be used to determine a level of cancer.

In other embodiments, sizes of organ-associated cell-free DNA can be measured. In an example using a urine sample voided from the bladder, a size profile can be measured of cell-free DNA fragments that naturally occur in the urine. A statistical measure of the size profile can indicate that the cell-free DNA fragments are collectively longer than expected for subjects with healthy bladder tissue. The indication of longer fragments can be used to identify bladder cancer in the subject. In another example using a urine sample, the urine sample can be retrieved from the renal pelvis. A determination about whether the kidney is inflamed can be made based on the statistical measure indicating that the cell-free DNA fragments are collectively longer than expected for subjects with a non-inflamed kidney.

In other embodiments, two different samples can be analyzed to determine whether a particular organ has cancer. Cell-free DNA in a blood sample and organ-associated sample (e.g., urine, saliva, or a stool sample) can both be analyzed to identify chromosomal regions exhibiting a copy number aberration. If the blood sample does not indicate cancer and the organ-associated sample does, then the subject can be identified as having cancer in an organ associated with the sample. For example, for a urine sample, the subject can be identified as having bladder cancer. Other cancers can also be detected, such as cancers of the urinary tract, transitional cell carcinomas that arise from the urothelium, and kidney cancers.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 16A-16C show the size profile for three void urine samples from patients with bladder cancer according to embodiments of the present invention.

FIGS. 19A and 19B show boxplots for the proportion of urinary cfDNA fragments longer than 70 bp (P>70 bp) in controls, bladder cancer patients with Ta-T1 disease, and bladder cancer patients with T2-T4 disease according to embodiments of the present invention.

TERMS

Figure 1:
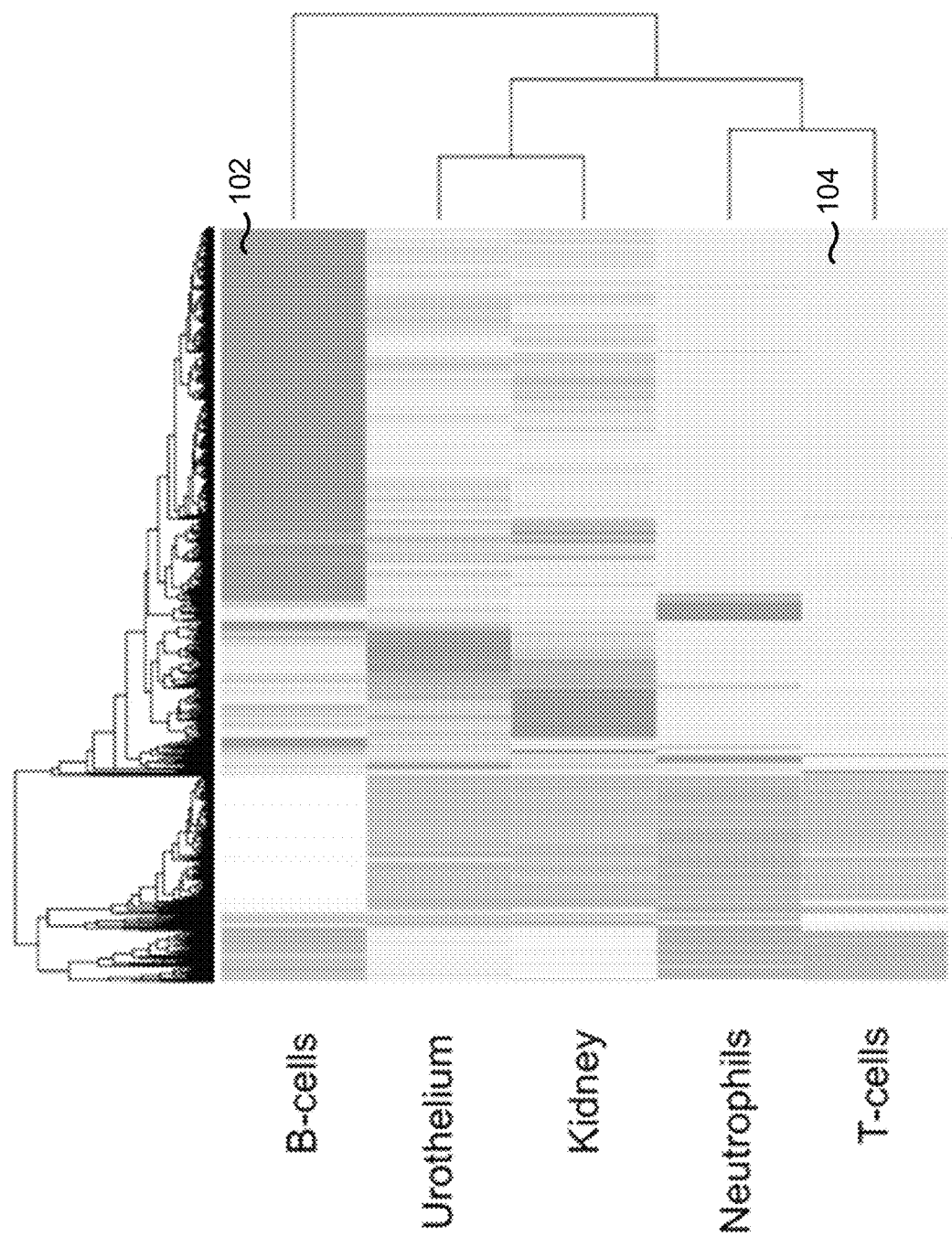
FIG. 1 displays the methylation density in 19,418 differentially methylated regions identified from the kidney, urothelium, B-cells, T-cells, and neutrophils according to embodiments of the present invention. Each vertical line represents a single differentially methylated region color-coded based on methylation density. Differentially methylated regions (DMR) with a high methylation density are represented in red, whereas loci with a low methylation density are represented in yellow.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia)) and contains one or more nucleic acid molecule(s) of interest. The biological sample can be a bodily fluid, such as blood, plasma, serum, urine, vaginal fluid, fluid from a hydrocele (e.g. of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at, for example, 30,000 g for another 10 minutes to remove residual cells.

As used herein, the term "locus" or its plural form "loci" is a location or address of any length of nucleotides (or base pairs) which has a variation across genomes. A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

The term "size profile" generally relates to the sizes of DNA fragments in a biological sample. A size profile may be a histogram that provides a distribution of an amount of DNA fragments at a variety of sizes. Various statistical parameters (also referred as size parameters or just parameter) can be used to distinguish one size profile to another. One parameter is the percentage of DNA fragment of a particular size or range of sizes relative to all DNA fragments or relative to DNA fragments of another size or range.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts.

"DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as N6-methyladenine, has also been reported.

A "site" corresponds to a single site, which may be a single base position or a group of correlated base positions, e.g., a CpG site. A "locus" may correspond to a region that includes multiple sites. A locus can include just one site, which would make the locus equivalent to a site in that context.

A "methylome" provides a measure of an amount of DNA methylation at a plurality of sites or loci in a genome. The methylome may correspond to all of the genome, a substantial part of the genome, or relatively small portion(s) of the genome. A "tumor methylome" corresponds to a methylome of a tumor of an organism (e.g., a human). The tumor methylome can be determined using tumor tissue or cell-free tumor DNA in maternal plasma. Other examples of tissue-specific methylomes of interest are the methylomes of organs (e.g. methylomes of brain cells, bones, the lungs, the heart, the muscles and the kidneys, etc.) that can contribute DNA into a bodily fluid (e.g. plasma, serum, sweat, saliva, urine, genital secretions, semen, stools fluid, diarrheal fluid, cerebrospinal fluid, secretions of the gastrointestinal tract, ascitic fluid, pleural fluid, intraocular fluid, fluid from a hydrocele (e.g. of the testis), fluid from a cyst, pancreatic secretions, intestinal secretions, sputum, tears, aspiration fluids from breast and thyroid, etc.). The organs may be transplanted organs.

A "tissue" corresponds to a group of cells of a same type. Different types of tissue may consist of different types of cells (e.g., hepatocytes, alveolar cells or blood cells), but also may correspond to tissue from different organisms (mother vs. fetus) or to healthy cells vs. tumor cells. "Reference tissues" correspond to tissues used to determine tissue-specific methylation levels. Multiple samples of a same tissue type from different individuals may be used to determine a tissue-specific methylation level for that tissue type.

The "methylation index" for each genomic site (e.g., a CpG site) refers to the proportion of sequence reads showing methylation at the site over the total number of reads covering that site. The "methylation density" of a region is the number of reads at sites within the region showing methylation divided by the total number of reads covering the sites in the region. The sites may have specific characteristics, e.g., being CpG sites. Thus, the "CpG methylation density" of a region is the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" refers the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels."

The term "level of a disease" or "level of a condition" can refer to whether a disease (e.g., cancer) exists, a stage of the disease, a size of tumor when the disease is cancer, whether there is metastasis, the total tumor burden of the body, and/or other measure of a severity of the disease. The level of disease could be a number or other indicia, such as symbols, alphabet letters, and colors. The level could be zero. The level of cancer also includes premalignant or precancerous conditions (states) associated with mutations or a number of mutations. The level of disease can be used in various ways. For example, screening can check if the disease is present in someone who is not known previously to have the disease. Assessment can investigate someone who has been diagnosed with the disease to monitor the progress of the disease over time, study the effectiveness of therapies or to determine the prognosis. In one embodiment, the prognosis can be expressed as the chance of a patient dying of the disease, or the chance of the disease progressing after a specific duration or time, or the chance of cancer metastasizing. Detection can mean 'screening' or can mean checking if someone, with suggestive features of the disease (e.g. symptoms or other positive tests), has the disease.

A "type" for a genomic locus (marker) corresponds to specific attributes for a locus across tissue types. A locus of a given type can have specific statistical variation in methylation levels across tissue types. A "category" for a genomic locus (marker) corresponds to specific variation in methylation levels for a locus across different individuals for a same tissue type. A set of genomic loci (markers) can be composed of any number of loci of various types and/or categories. Thus, a set of loci corresponds to loci selected for a particular measurement and does not connote any particular properties of the loci in the set. The description primarily refers to type I loci and type II loci. A set of genomic sites may not have a specific methylation signature for a specific tissue type, e.g., only or predominantly methylated in the specific tissue type. Such a set is referred to as type II sites. These genomic sites can be used in combination with genomic sites that do have a specific signature, which are referred to as type I sites.

An "organ-associated sample" can refer to a sample that is created by a particular organ (e.g., urine created by kidneys) or passes through the particular organ (e.g., urine passing though the bladder), as may occur, for example, in urine, saliva, pleural fluid, blood, and stool samples. The sample includes cell-free DNA and can be a mixture of cell-free and cellular DNA.

Urothelium (or uroepithelium) is an example of "transitional epithelium". It is the type of epithelium that lines much of the urinary tract including the renal pelvis, the ureters, the bladder, and parts of the urethra.

DETAILED DESCRIPTION

Urinary cell-free (cf) DNA, as well as other organ-associated samples, hold great potential as a completely noninvasive form of liquid biopsy, or other non-invasive biopsy, such as a stool sample. Knowledge of the composition of cfDNA by tissue of origin is useful for guiding its clinical uses. However, the composition of such samples can be highly variable, thereby limiting wide applicability for use as a biopsy. For example, the amount of transrenal DNA from any particular organ can vary widely from sample to sample, thereby making the percentage of cell-free DNA from a kidney vary as well.

CpG site methylation is an important form of epigenetic regulation and methylation signatures can be identified for different tissues (19,20) and cell types (21). We have recently demonstrated that the proportional contribution of plasma cfDNA from different tissues can be ascertained using genomewide bisulfite sequencing and deconvolution analyses of the sequencing data (22).

The present disclosure analyzes the composition of urinary cfDNA by employing methylation deconvolution, which uses tissue-specific methylation patterns (also called reference patterns), to infer the proportional contribution of urinary cfDNA from different tissues. Such analysis can involve using methylation patterns of a disease tissue type, e.g., cancerous urothelium cells. Techniques using such deconvolution can determine a level of the associated disease. Results show the analysis of urinary cfDNA from bladder cancer patients to using methylation deconvolution to identify an increased proportion of cfDNA originating from the bladder tumor.

Other changes in fragment sizes, tumor-associated copy numbers, and methylation levels are also analyzed. For example, the size profile of voided urine is used to identify whether the subject has bladder cancer. Further, the size profile of urine from the renal pelvis is used to identify whether the kidney is inflamed.

Additionally, copy number aberrations can be used to detect cancer using blood, e.g., as is described in U.S. Pat. No. 8,741,811, which is incorporated by reference in its entirety. However, it may not be known which organ has a tumor, as blood includes tissue from many organs and is thus associated with many organs. Urine or other samples that typically have tissue from fewer organs can be analyzed, but transrenal DNA having copy number aberrations can still be from various organs. Thus, it may be challenging to identify the particular organ having the tumor. One way to address this involves techniques described herein where a copy number analysis of cell-free DNA from an organ-associated sample (e.g., saliva, pleural fluid, urine, or a stool sample) and a blood sample to obtain separate determinations of a level of cancer. If the blood sample does not indicate cancer and the voided sample does, then cancer can be identified as being from an organ associated with the voided sample, e.g., bladder cancer for urine.

I. DECONVOLUTION USING DISEASED TISSUE REFERENCE PATTERN

Samples (e.g., blood and urine) can include multiple tissue types, each contributing different fractions of cell-free DNA. As the DNA of different types of tissues typically have different methylation patterns, the methylation levels measured in a particular sample can be used to determine the fractional contributions of each of a plurality of tissue types in the sample. A process of deconvolution can use tissue-specific methylation patterns to determine the fractional contributions, e.g., as described in U.S. Patent Publication 2016/0017419, which is incorporated by reference in its entirety.

Changes in the fractional contribution can be used to detect abnormalities. However, problems can arise when certain samples have high variability in fractional contributions, e.g., in urine. Some embodiments can address this problem by using a tissue-specific methylation pattern that corresponds specifically with the diseased tissue, as opposed to using a methylation pattern that determined from healthy tissue of the organ. First, issues with urine as a sample are discussed, as well as details about deconvolution.

A. Urine as the Sample

While hematopoietic cells are consistently the predominant contributor to plasma cfDNA which is present at relatively stable concentrations (22,27), the quantity and composition of urinary cfDNA is highly variable. For example, the kidney contribution to cfDNA can vary from 4.2-94%, or 104-3,970 GE/ml urine in kidney transplant patients who are clinically stable. This degree of compositional variation compounds the variation in the concentration of total cfDNA in urine (225-25,710 GE/ml urine from transplant patients) and may explain why an assay aimed solely at the sensitive detection of cfDNA from a single source may encounter samples with undetectable levels. This may highlight the difference between the contents of plasma being maintained at a homeostatic equilibrium, while the contents of voided urine is the excretory by-product of homeostatic requirements after the one time, unidirectional passage through the urinary system. While varying hydration status could conceivably affect total cfDNA concentration, the dilutional effects cannot account for the variation in proportional contribution from each tissue.

Investigation of urinary cfDNA is further complicated by the fact that the majority of urinary cfDNA fragments are short (<100 bp) and DNaseI, the major secretory DNA-hydrolyzing enzyme, is highly expressed in the kidney and bladder (proteinatlas.org/) and is present (Ito et al. 1984) and highly active (Nadano et al. 1993) in urine. The variation in cfDNA quantity detectable from each tissue source calls for an enhanced understanding of urinary cfDNA composition by tissue of origin, and also changes that cfDNA may undergo as it descends the urinary tract.

Accordingly, a challenge in determining the composition in cfDNA in urine lies in the fact that urinary cfDNA is shorter than that in plasma (about 50 bases in urine and 150 in plasma), and urinary DNA is continually degraded as it passes through the urinary tract. Further, extraction of cell-free DNA from urine is more difficult that from plasma due to the presence of DNaseI. Thus, it is not clear that methylation deconvolution would work for fragments that are so much shorter.

We hypothesized that blood cells, the kidney, and urothelium were the major contributors, respectively, for the pre-renal, renal, and post-renal release of cfDNA into urine. Around 80% of the cfDNA in plasma is from hematopoietic cells (27) and thus if a significant amount of plasma cfDNA is able to be filtered through the kidney into the urine, these DNA fragments would likely bear characteristics of the hematopoietic cells. However, the composition of transrenal DNA from various tissues is variable in urine.

We conducted a global survey of urinary cfDNA composition using genomewide bisulfite sequencing. DNA fragments were mapped onto the Watson and Crick strands. Using one lane per sample, we achieved a median of 80 million uniquely mappable, non-duplicated reads, with an average sequencing depth of 2.42 at CpG sites across the genome. We used tissue specific methylation signatures and methylation deconvolution to deduce the proportional contribution from each tissue.

We demonstrate that we are able to determine the proportional contribution of cell-free and cellular DNA in urine. The proportional contributions derived from methylation deconvolution are highly correlated with those calculated using allograft-derived donor-specific genetic markers in the urine of hematopoietic stem cell and renal transplant recipients. We found a large variation of proportional contributions from different tissues. cfDNA from urine obtained from the renal pelvis has a higher proportion of longer fragments compared with voided urine. In vitro incubation of urinary cfDNA at 37° C. to mimic in vivo degradation revealed that the absolute concentration of urinary cfDNA decreased with a half-life of 3.5-4.9 hours. Despite in vivo degradation, validation using the void urine of renal and bone marrow transplant patients showed a high correlation in proportional contribution between methylation deconvolution and donor-specific SNPs.

The DNA methylation from the cell-free urine and urine pellet is compared with reference methylomes from different normal and pathological tissues, including tissues that constitute the urinary tract. Methylation deconvolution of urinary cfDNA from bladder cancer patients identified an increased proportional contribution from the cancer. Such urinary cfDNA also exhibited aberrations in size profile, copy numbers, and global hypomethylation and/or hypermethylation.

This global survey of urinary cfDNA has deepened our understanding of the composition, degradation, and variation of cfDNA in the urinary tract and has laid a foundation for the use of genomewide urinary cfDNA sequencing as a molecular diagnostics tool.

B. Methylation Deconvolution

The principle of methylation deconvolution can be illustrated using a single methylation genomic site (methylation marker) to determine a composition of a DNA mixture from an organism. An organism may be an animal, including a mammal or a human. Assume that tissue A is completely methylated for the genomic site, i.e. methylation density (MD) of 100% and tissue B is completely unmethylated, i.e. MD of 0%. In this example, methylation density refers to the percentage of cytosine residues with the context of CpG dinucleotides being methylated in the region of interest.

If the DNA mixture C is composed of tissue A and tissue B and the overall methylation density of the DNA mixture C is 60%, we can deduce the proportional contribution of tissues A and B to the DNA mixture C according to the following formula:

$$MD_C = MD_A \times a + MD_B \times b,$$

where $MD_A$, $MD_B$, $MD_C$ represent the MD of tissues A, tissue B and the DNA mixture C, respectively; and a and b are the proportional contributions of tissues A and B to the DNA mixture C. In this particular example, it is assumed that tissues A and B are the only two constituents of the DNA mixture. Therefore, a+b=100%. Thus, it is calculated that tissues A and B contribute 60% and 40%, respectively, to the DNA mixture.

The methylation densities in tissue A and tissue B can be obtained from samples of the organism or from samples from other organisms of the same type (e.g., other humans, potentially of a same subpopulation). If samples from other organisms are used, a statistical analysis (e.g., average, median, geometric mean) of the methylation densities of the samples of tissue A can be used to obtain the methylation density $MD_A$, and similarly for $MD_B$.

Genomic sites can be chosen to have minimal inter-individual variation, for example, less than a specific absolute amount of variation or being within a lowest portion of genomic sites tested. For instance, for the lowest portion, embodiments can select only genomic sites having the lowest 10% of variation among a group of genomic sites tested. The other organisms can be taken from healthy persons, as well as those with particular physiologic conditions (e.g. pregnant women, or people with different ages or people of a particular sex), which may correspond to a particular subpopulation that includes the current organism being tested.

The other organisms of a subpopulation may also have other pathologic conditions (e.g. patients with hepatitis or diabetes, etc.). Such a subpopulation may have altered tissue-specific methylation patterns for various tissues. The methylation pattern of the tissue under such disease condition can be used for the deconvolution analysis in addition to using the methylation pattern of the normal tissue. This deconvolution analysis may be more accurate when testing an organism from such a subpopulation with those conditions. For example, a cirrhotic liver or a fibrotic kidney may have a different methylation pattern compared with a normal liver and normal kidney, respectively. Thus, if a patient with liver cirrhosis was screened for other diseases, it can be more accurate to include a cirrhotic liver as one of the candidates contributing DNA to the plasma DNA, together with the healthy tissues of other tissue types.

More genomic sites (e.g., 10 or more) may be used to determine the constitution of the DNA mixture when there are more potential candidate tissues. The accuracy of the estimation of the proportional composition of the DNA mixture is dependent on a number of factors including the number of genomic sites, the specificity of the genomic sites (also called "sites") to the specific tissues, and the variability of the sites across different candidate tissues and across different individuals used to determine the reference tissue-specific levels. The specificity of a site to a tissue refers to the difference in the methylation density of the genomic sites between the particular tissue and other tissue types.

The larger the difference between their methylation densities, the more specific the site to the particular tissue would be. For example, if a site is completely methylated in the liver (methylation density=100%) and is completely unmethylated in all other tissues (methylation density=0%), this site would be highly specific for the liver. Whereas, the variability of a site across different tissues can be reflected by, for example, but not limited to, the range or standard deviation of methylation densities of the site in different types of tissue. A larger range or higher standard deviation would allow a more precise and accurate determination of the relative contributions of the different organs to the DNA mixture mathematically. The effects of these factors on the accuracy of estimating the proportional contribution of the candidate tissues to the DNA mixture are illustrated in the later sections of this application.

Here, we use mathematical equations to illustrate the deduction of the proportional contribution of different organs to the DNA mixture. The mathematical relationship between the methylation densities of the different sites in the DNA mixture and the methylation densities of the corresponding sites in different tissues can be expressed as:

$$\overline{MD}_i = \Sigma_k(p_k \times MD_{ik}),$$

where $\overline{MD}_i$ represents the methylation density of the site i in the DNA mixture; $p_k$ represents the proportional contribution of tissue k to the DNA mixture; $MD_{ik}$ represents the methylation density of the site i in the tissue k. When the number of sites is the same or larger than the number of organs, the values of individual $p_k$ can be determined. The tissue-specific methylation densities can be obtained from other individuals, and the sites can be chosen to have minimal inter-individual variation, as mentioned above.

Additional criteria can be included in the algorithm to improve the accuracy. For example, the aggregated contribution of all tissues can be constrained to be 100%, i.e.

$$\Sigma_k p_k = 100\%.$$

Furthermore, all the organs' contributions can be required to be non-negative:

$$p_k \geq 0, \forall k$$

Due to biological variations, the observed overall methylation pattern may not be completely identical to the methylation pattern deduced from the methylation of the tissues. In such a circumstance, mathematical analysis would be required to determine the most likely proportional contribution of the individual tissues. In this regard, the difference between the observed methylation pattern in the DNA and the deduced methylation pattern from the tissues is denoted by W.

$$W = O - \sum_k (p_k \times M_k)$$

where O is the observed methylation pattern for the DNA mixture and $M_k$ is the methylation pattern of the individual tissue k. $p_k$ is the proportional contribution of tissue k to the DNA mixture. The most likely value of each $p_k$ can be determined by minimizing W, which is the difference between the observed and deduced methylation patterns. This equation can be resolved using mathematical algorithms, for example by, but not limited to, using quadratic programming, linear/non-linear regression, expectation-maximization (EM) algorithm, maximum likelihood algorithm, maximum a posteriori estimation, and the least squares method.

C. Identification of Differentially Methylated Regions for Urinary cfDNA Tissue Mapping A reference methylome can be assembled based on publically-available methylomes, and also the whole-genome bisulphite sequencing of normal and pathological samples obtained from different tissues. Sample tissues can be derived from tissues including, but not restricted to the kidney cortex, kidney medulla, ureter, bladder urothelium, bladder muscle, prostate (luminal, central, and peripheral), and seminal vesicle. The tissue and cellular composition of the sample can be obtained intra-operatively and ascertained via gross dissection.

We aimed to characterize the methylome of blood cells (neutrophils, T-cells and B-cells), the kidney, and urothelium in order to identify methylation signatures that could differentiate between these tissues. We made use of publicly available whole genome bisulfite sequencing data for blood cells (Human Epigenome Atlas, genboree.org/epigenomeatlas/index.rhtml, (28)) and we obtained kidney and urothelial tissues from patients undergoing renal transplantation or urologic surgery, in order to perform whole genome bisulfite sequencing to 35-40× coverage.

Tissues which have a similar methylation density across multiple CpG sites can be grouped together and differentially methylated regions (DMR) that are informative can be identified. Using the kidney, urothelium, neutrophils, B-cells, and T-cells, 19,418 DMRs were identified for use as methylation markers. This includes 3,549 type 1 markers, where the methylation density at DMR is significantly different (Z-score>3) in one tissue compared with the other 4 tissues, and 15,869 type 2 markers where the methylation density shows variation across different tissues.

FIG. 1 is a heat map showing methylation densities at the 19,418 differentially methylated regions (DMR) in neutrophils, B-cells, T-cells, kidney and urothelium. Each vertical line represents a DMR and high to low methylation densities are represented from red (e.g., section 102) to yellow (e.g., section 104). Hierarchical clustering shows that the methylation pattern at these DMRs in blood cells are grossly different to those in the kidney and urothelium.

Urinary cfDNA was sequenced after bisulfite treatment and the methylation patterns observed in cfDNA fragments at the DMRs were compared with the methylation signatures in the five reference tissues, and using the methylation deconvolution algorithm as previously described (22). We then inferred the proportional contributions of neutrophils, B-cells, T-cells, kidney and urothelium. FIG. 1 shows that blood cells, kidney, and urothelium are in the composition of normal urinary cfDNA.

We sequenced a total of 46 bladder cancer cases and 39 controls to a median of 29.2 M uniquely mappable reads using 41×2 paired end bisulfite sequencing. Bladder cancer cases ranged from non-invasive very low grade (Ta PUNLMP) to T4 high grade disease. All controls had either blood in uristix or gross hematuria. Eight controls underwent flexible cystoscopy for persistent blood in uristix or gross hematuria as part of their routine clinical care and were confirmed to be negative for malignancy. Fifteen controls were used to establish the baseline level of methylation and copy number. The remaining 24 controls were used in the testing group.

Figure 2:
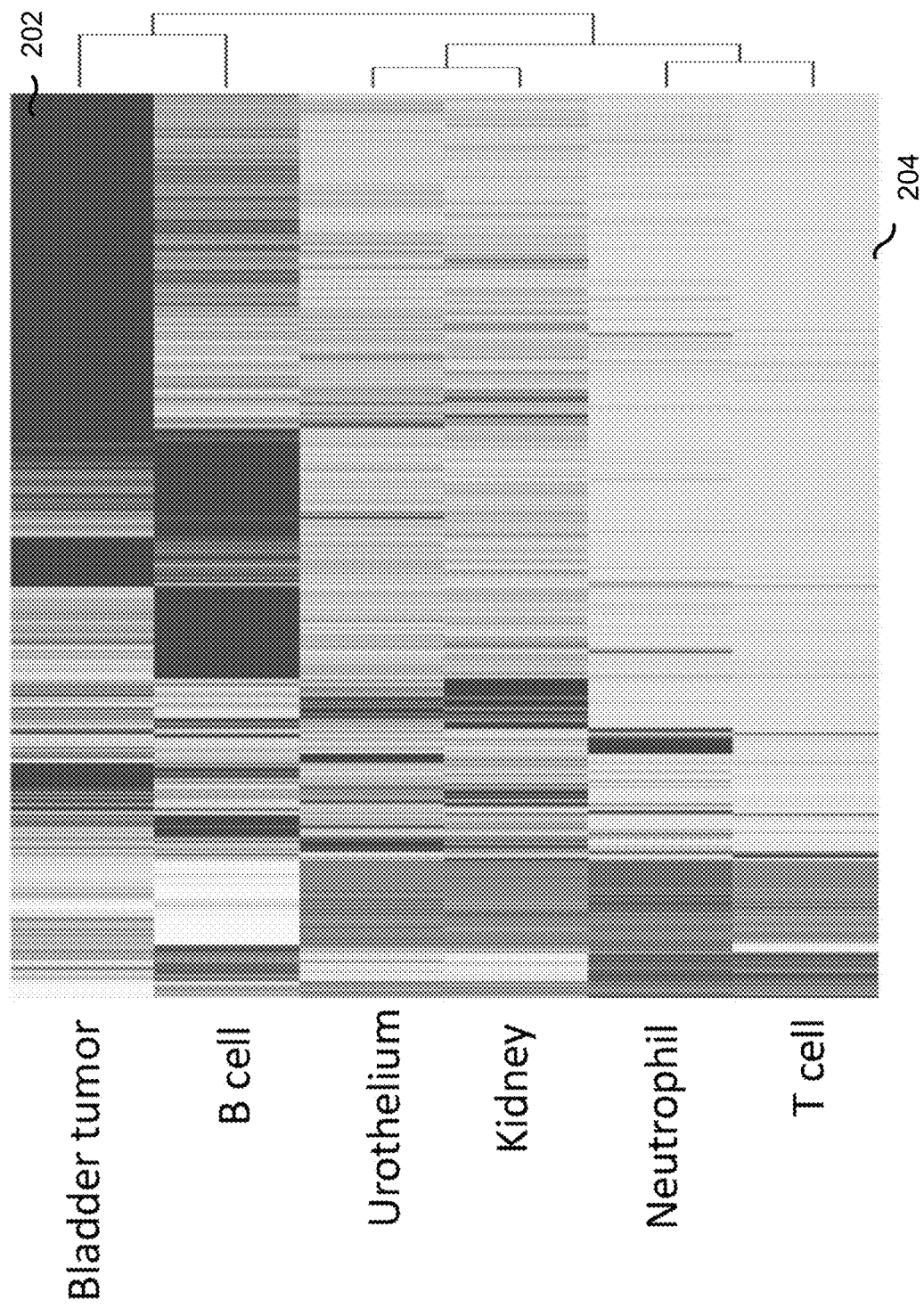
FIG. 2 is a heat map showing the methylation densities of 27,371 differentially methylated regions (DMR) in bladder tumor, B-cells, urothelium, kidney, neutrophils, and T-cells according to embodiments of the present invention.

FIG. 2 is a heat map showing the methylation densities of 27,371 differentially methylated regions (DMR) in bladder tumor, B-cells, urothelium, kidney, neutrophils, and T-cells. Each vertical line represents a DMR color code based on methylation density. The DMRs in FIG. 2 are slightly different from the DMRs in FIG. 1. The vertical lines are ordered by methylation level. Only DMRs in autosomes are included. Hypomethylation is colored red (e.g., section 202), and hypermethylation is colored yellow (e.g., section 204). These DMRs are employed for methylation deconvolution to identify the proportion of urinary cfDNA contributed from bladder tumor in each urine sample. Bladder tumor tissue was sequenced to 8.5× coverage of the haploid genome to identify the DMRs for methylation deconvolution. FIG. 2 shows that the bladder tumor DNA can be detected. Any tissue with an aberrant methylome can be detected in other physiological or pathological conditions.

Genomewide bisulfite sequencing can be used to longitudinally monitor bladder cancer patients as evidenced by pre- and post-operative urine samples.

D. Methylation Deconvolution in Hematopoietic Stem Cell and Renal Transplant Patients and Validation Using Donor-Specific Genotypes We conducted whole genome bisulphite sequencing for the cfDNA from 26 and 5 urine samples from the kidney and transplant HSCT patients respectively. The methylation density at 19,418 DMR across the genome allowed us to determine the proportion of DNA that originated from the kidney, urothelium, B-cells, T-cells, and neutrophils. Donor specific SNPs allowed us to identify the proportion of DNA fragments from the kidney and blood cells in each urine sample and the accuracy of methylation deconvolution was compared with the gold standard determined by donor specific SNPs. The proportional contribution of blood cells from methylation deconvolution was the summation of B-cells, T-cells, and neutrophils.

We ascertained donor and recipient germline genotype information using the Illumina OMNI 2M SNP arrays for HSCT and renal transplant patients. We collected 31 urine samples for bisulfite sequencing. We obtained an average of 80 million uniquely mapped reads for each sample, and the identification of fragments harboring donor and recipient-specific SNPs allowed the accurate calculation of the proportion of cfDNA fragments from the donor tissues.

Figure 3:
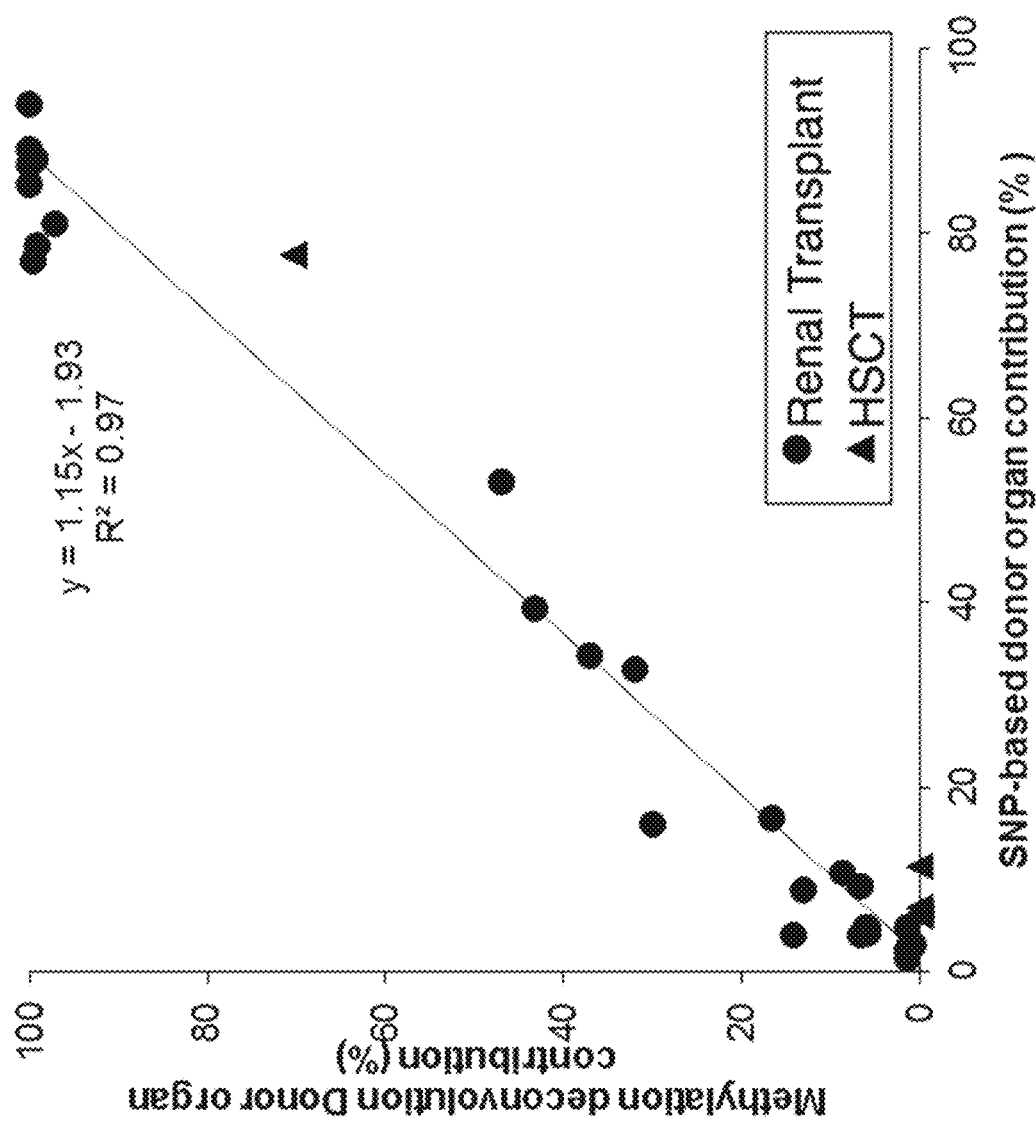
FIG. 3 shows the proportional contribution of cfDNA derived from the blood cells and kidney in 31 urine samples from and hematopoietic stem cell transplantation (HSCT) (triangles) and renal transplant (round dots) patients according to embodiments of the present invention.

FIG. 3 shows the proportional contribution of cfDNA derived from the blood cells and kidney in the 31 urine samples from and HSCT (triangles) and renal transplant (round dots) patients according to embodiments of the present invention. The x axis displays the percentage contribution from the donor organ as calculated from donor-specific SNPs, and the y axis displays the percentage contribution of the donor organ as deduced by methylation deconvolution. The proportional contributions of the donor tissues determined by methylation deconvolution and the proportions determined using donor and recipient specific genotypes were highly correlated ($R^2=0.97$).

These results demonstrated the ability of methylation deconvolution to determine the proportional contribution of different tissues into urinary cfDNA over a good dynamic range. Using donor-specific SNPs, the proportion of donor hematopoietic cell contribution to urinary cfDNA varied from 6-78%, and the proportion of donor kidney contribution varied from 1-94%. The full urinary cfDNA methylation deconvolution results for the 31 transplant urine samples are listed in Table 1.

TABLE 1

Methylation deconvolution results for 31 HSCT and renal transplant samples. The percentage contribution from the kidney, urothelium, neutrophil, T cell and B cell is displayed for each sample.

| | Transplant type | Kidney | Urothelium | Neutrophils | T-cells | B-cells |
|---|---|---|---|---|---|---|
| T10 | Renal | 97.2 | 0.0 | 0.0 | 0.0 | 2.8 |
| T11 | Renal | 0.7 | 8.5 | 85.4 | 2.5 | 3.0 |
| T18 | Renal | 6.5 | 9.0 | 79.2 | 4.0 | 1.3 |

TABLE 1-continued

Methylation deconvolution results for 31 HSCT and renal transplant samples. The percentage contribution from the kidney, urothelium, neutrophil, T cell and B cell is displayed for each sample.

| | Transplant type | Kidney | Urothelium | Neutrophils | T-cells | B-cells |
|---|---|---|---|---|---|---|
| T20 | Renal | 1.4 | 8.4 | 83.2 | 5.2 | 1.8 |
| T29 | Renal | 100.0 | 0.0 | 0.0 | 0.0 | 0.0 |
| T34 | Renal | 43.2 | 16.2 | 39.0 | 0.0 | 1.6 |
| T35 | Renal | 14.1 | 3.8 | 78.7 | 0.0 | 3.4 |
| T40 | Renal | 100.0 | 0.0 | 0.0 | 0.0 | 0.0 |
| T42 | Renal | 36.9 | 11.4 | 50.5 | 0.0 | 1.2 |
| T50 | Renal | 31.8 | 64.0 | 0.0 | 0.0 | 4.2 |
| T51 | Renal | 46.8 | 35.8 | 12.6 | 3.7 | 1.1 |
| T53 | Renal | 16.5 | 13.8 | 65.4 | 0.0 | 4.3 |
| T54 | Renal | 8.5 | 8.3 | 79.1 | 1.7 | 2.3 |
| T56 | Renal | 13.0 | 20.8 | 59.3 | 6.9 | 0.0 |
| T57 | Renal | 1.3 | 13.8 | 80.0 | 1.7 | 3.1 |
| T63 | Renal | 5.7 | 5.5 | 83.7 | 2.1 | 3.0 |
| T64 | Renal | 1.4 | 6.0 | 85.6 | 4.5 | 2.5 |
| T65 | Renal | 6.0 | 5.0 | 82.0 | 4.9 | 2.1 |
| T69 | Renal | 99.3 | 0.0 | 0.0 | 0.0 | 0.7 |
| T72 | Renal | 5.7 | 12.0 | 72.0 | 7.8 | 2.6 |
| T75_A | Renal | 99.1 | 0.0 | 0.0 | 0.0 | 0.9 |
| T75_B | Renal | 99.6 | 0.0 | 0.0 | 0.0 | 0.4 |
| T80_A | Renal | 100.0 | 0.0 | 0.0 | 0.0 | 0.0 |
| T80_B | Renal | 100.0 | 0.0 | 0.0 | 0.0 | 0.0 |
| T88 | Renal | 30.0 | 16.3 | 49.0 | 2.9 | 1.7 |
| T89 | Renal | 6.6 | 4.1 | 87.0 | 0.3 | 2.0 |
| T45 | HSCT | 29.6 | 0.0 | 60.5 | 8.5 | 1.4 |
| T85 | HSCT | 100.0 | 0.0 | 0.0 | 0.0 | 0.0 |
| T86 | HSCT | 100.0 | 0.0 | 0.0 | 0.0 | 0.0 |
| T102_A | HSCT | 100.0 | 0.0 | 0.0 | 0.0 | 0.0 |
| T102_B | HSCT | 100.0 | 0.0 | 0.0 | 0.0 | 0.0 |

These results demonstrated that the contributions of blood cells, kidney, and urothelium were highly variable between different samples. In some samples, there was a large variation in the proportional contribution from a particular tissue in the urine samples from the same individual taken on different days (e.g. T45 and T86). The proportional contribution of each of these tissues can be as low as 0%, and can rise up to 93%, 100% and 64% for blood cells, kidney and urothelium, respectively. Across the 31 urine samples the median and interquartile ranges of the proportional contributions measured using methylation deconvolution for blood cells, kidney and urothelium were 52% (0-84%), 32% (7-100%) and 5% (0-12%), respectively.

E. Determination of Cancer Using Methylation Deconvolution

This section describes methylation deconvolution of urinary cfDNA using the methylome of urothelium and bladder tumor DNA. The deconvolution can account for variability in the absolute amounts of DNA from different tissues. But, as described above, there is high variability in the contributions of different tissues in urine. Thus, if contribution from one source is low or high, it is not necessarily abnormal.

Figure 4C:
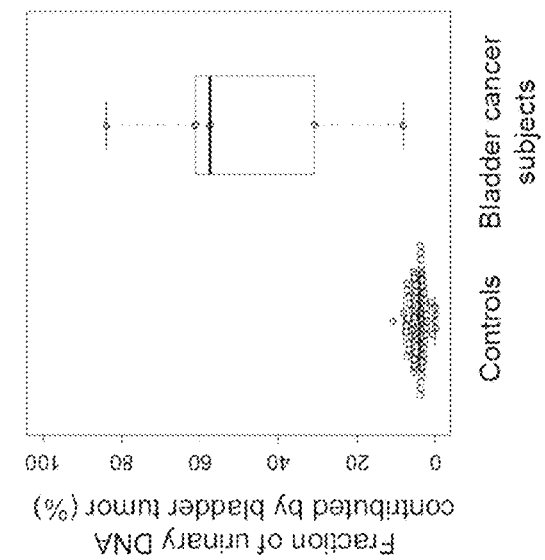
FIGS. 4A-4C show plots of methylation deconvolution for bladder cancer cases and cancer-free controls for fractions defined using different tissue-specific methylation patterns, including normal urothelium cells (FIG. 4A), urothelium and bladder cancer cells as a single tissue-specific methylation patterns (FIG. 4B), and urothelium and bladder cancer cells as separate tissue-specific methylation patterns (FIG. 4C) according to embodiments of the present invention.
Figure 4B:
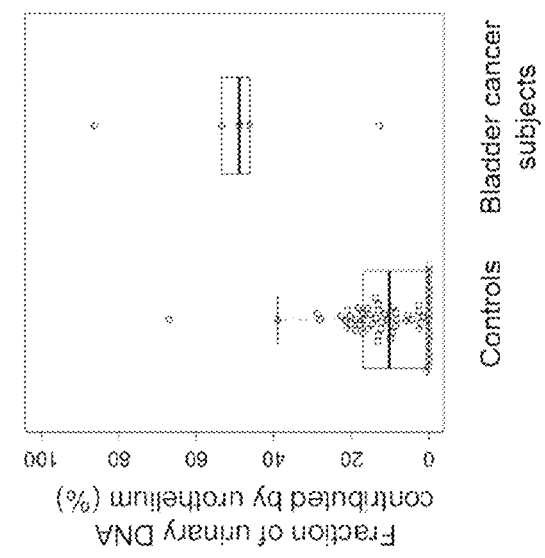
Figure 4A:
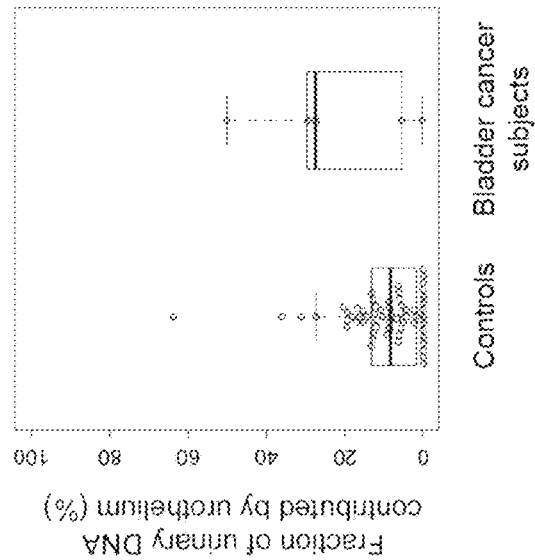

FIG. 4A-4C shows plots of methylation deconvolution for bladder cancer cases and cancer-free controls for fractions defined using different tissue-specific methylation patterns (also referred to as reference patterns), including normal urothelium cells (FIG. 4A), urothelium and bladder cancer cells as a single tissue-specific methylation patterns (FIG. 4B), and urothelium and bladder cancer cells as separate tissue-specific methylation patterns (FIG. 4C). Proportional contribution derived from methylation deconvolution is displayed on the y axis.

1. Use of Normal Urothelium as Reference

The vast majority of bladder cancers are transitional cell carcinomas that arise from urothelial cells. However, the methylation of bladder tumor derived DNA could resemble normal urothelium, or could display a grossly different and distinct methylation pattern. We studied the proportional contribution of urothelium into the urinary cfDNA from bladder cancer patients compared with cancer-free controls, reasoning that bladder tumors could have an increased cell turnover and could release cfDNA fragments resembling normal urothelium FIG. 4A shows the fractional contribution of normal urothelium when tissue-specific methylation patterns include kidney, normal urothelium, B-cell, T-cell, and neutrophil in methylation deconvolution. The percentage contribution of normal urothelium in non-cancer and bladder cancer cases are variable and largely overlapping, with no significant difference between the two groups (Mann-Whitney U test p=0.15). Thus, methylation deconvolution found that there was no significant difference in the urothelial contribution between the bladder cancer patients and tumor-free controls. This suggests that there is no marked increase in cfDNA that resembles normal urothelium in the urine of patients with bladder cancer.

2. Use of Sites with Common Methylation Between Normal and Cancer

Since bladder cancers are thought to arise from urothelial cells that have undergone malignant change, we sequenced a bladder tumor sample to 8.5× coverage to identify similarities and differences between the methylome of bladder tumors and normal urothelium. We identified 7,201 DMRs where the methylation density was similar (<10% difference) between bladder tumors and normal urothelium. We then conducted methylation deconvolution with this definition of urothelium, along with kidney, B-cell, T-cell, and neutrophils.

FIG. 4B shows the fractional contribution of urothelium when tissue-specific methylation patterns include kidney, B-cell, T-cell, neutrophil, and urothelial markers that were conserved in bladder cancer according to embodiments of the present invention. The urothelial contribution, as defined by the DMR that were conserved in normal urothelium and bladder cancer, is highly variable in non-cancer (0-67%) and bladder cancer patients (13-86%). Using methylation markers that were conserved in normal urothelium and bladder cancer, there was an increased urothelial contribution from bladder cancer subjects compared with controls (Mann-Whitney U test P=0.003). There was a 4.5 fold increase in the median urothelial contribution from bladder cancer subjects compared with controls. The median for controls was 10.34, and the median for bladder cancer subjects was 48.9.

3. Use of Tumor Urothelium as a Separate Reference

Lastly, we included the bladder tumor methylome as a separate reference pattern, together with neutrophils, T-cells, B-cells, kidney, and normal urothelium. Thus, the normal and tumor urothelial are treated as separate tissues. The tumor urothelial was determined based on a biopsied tumor. The tumor reference pattern can be determined based on one or multiple such biopsied tumors. When using multiple biopsies, the tumor reference pattern can be limited to DMRs that occur in all or a specified percentage (e.g., greater than 50%) of the biopsies. Different tumor biopsies could also be considered separate tissues having different reference patterns, thereby allowing classification of a particular group of tumor cells. We identified DMRs across the six cells/tissues and used the identified DMRs in methylation deconvolution.

FIG. 4C shows the fractional contribution of bladder tumor cells when tissue-specific methylation patterns include kidney, urothelium, B-cell, T-cell, neutrophil, and bladder cancer according to embodiments of the present invention. We found that the cases with bladder cancer had 14-fold increase in the median bladder tumor contribution while the non-cancer controls had very low levels of bladder tumor contribution. The non-cancer cases have a very low bladder tumor contribution (0-11%) while the bladder cancer cases have an elevated bladder tumor contribution of up to 84%. The Mann-Whitney U test showed that there was a significant difference between the two groups (p=0.0002). The median contribution for the controls is 4.13, and the median contribution for the bladder cancer subjects is 57.45.

Accordingly, a cutoff value of about 20 would provide an accurate classification of the level of cancer. Other values near 20 would provide similar sensitivity and specificity. For other diseases or cancers, the specific cutoff value may vary.

The significant difference between the percentage contribution of bladder tumor in the urine of bladder cancer patients versus normal controls suggests that the bladder tumor contribution can be used to differentiate bladder cancer patients from non-cancer controls. As the bladder cancer methylome was determined based on DNA from one bladder tumor, this suggests that there are methylation patterns that are shared in the bladder cancer DNA from different patients.

For the two cases of muscle-invasive bladder cancer undergoing radical cystecomy, a section of the small intestines was used to form an ileal conduit or neobladder, for urine drainage and storage in lieu of the bladder. With the small intestines being in direct contact with urine, we performed methylation deconvolution with bladder tumor and small intestines in the pre- and post-operative urine samples to see if we could detect the reduction in bladder tumor contribution and increase in small intestines contribution. Both post-operative bladder cancer samples showed a marked decrease in bladder tumor contribution to the level observed by the normal controls (Table 2). In post-operative samples, there was also a significant increase in contributions from the neutrophils as well as the small intestines.

TABLE 2

Methylation deconvolution results showing proportional tissue contribution, using neutrophils, T-cells, B-cells, kidney, urothelium, bladder tumor, and small intestines as references in the pre- and post-operative urine samples. The two patients A and B correspond to the size profiles in FIGS. 15A and 15B, respectively.

|  | Kidney | Uro-thelium | Bladder tumor | Small intestines | Neutro-phils | T-cells | B-cells |
|---|---|---|---|---|---|---|---|
| A pre-op | 9.9 | 0.0 | 56.2 | 1.9 | 24.7 | 0.0 | 7.3 |
| A post-op | 3.2 | 8.8 | 4.9 | 19.9 | 59.3 | 1.8 | 2.1 |
| B pre-op | 0.0 | 0.0 | 78.8 | 7.2 | 0.0 | 0.0 | 14.0 |
| B post-op | 1.5 | 3.5 | 3.1 | 24.4 | 61.8 | 2.9 | 2.8 |

Comparing pre- and post-operative results, there is a decrease in contribution from the bladder tumor and an increase in contribution from the small intestines and neutrophils. The increase in the neutrophils would be expected just after surgery. Accordingly, in the pre-operative samples from the five bladder cancer patients, embodiments were able to use methylation deconvolution to detect a significant increase in cfDNA contribution from the bladder tumor cells into the urine, but there was no significant difference in normal urothelial contribution between cancer cases and normal controls. This suggests that the bladder tumor methylome is grossly different to that of normal urothelial cells and that embodiments can use a single bladder tumor reference methylome to identify increased tumor contribution in the urinary cfDNA from different bladder cancer patients. The current results show that a representative bladder cancer methylome can be used as a reference to detect an increased contribution.

For urinary cfDNA to be used as a 'liquid biopsy' for disease detection and monitoring, it is useful to understand the origin of urinary cfDNA and the changes that it undergoes in the urinary tract. Here, we demonstrate that whole genome bisulfite sequencing of urinary cfDNA allows the recognition of methylation signatures that are characteristic of different tissues and thus allows a global survey of the composition of urinary cfDNA by tissue type. While previous studies generally concentrated on identifying urinary cfDNA from a single source, a global survey of the cfDNA in a urine sample shows the proportional contribution of each tissue type and allows the simultaneous comparison of different tissue contributions in different urine samples. The use of methylation signatures to detect the origin of cfDNA has the advantage over methods based on genetic variations, which require prior knowledge of donor specific alleles, or tumor specific somatic mutations that may be unique to each patient.

F. Method of Determining Disease Using Diseased Tissue as a Reference

Figure 5:
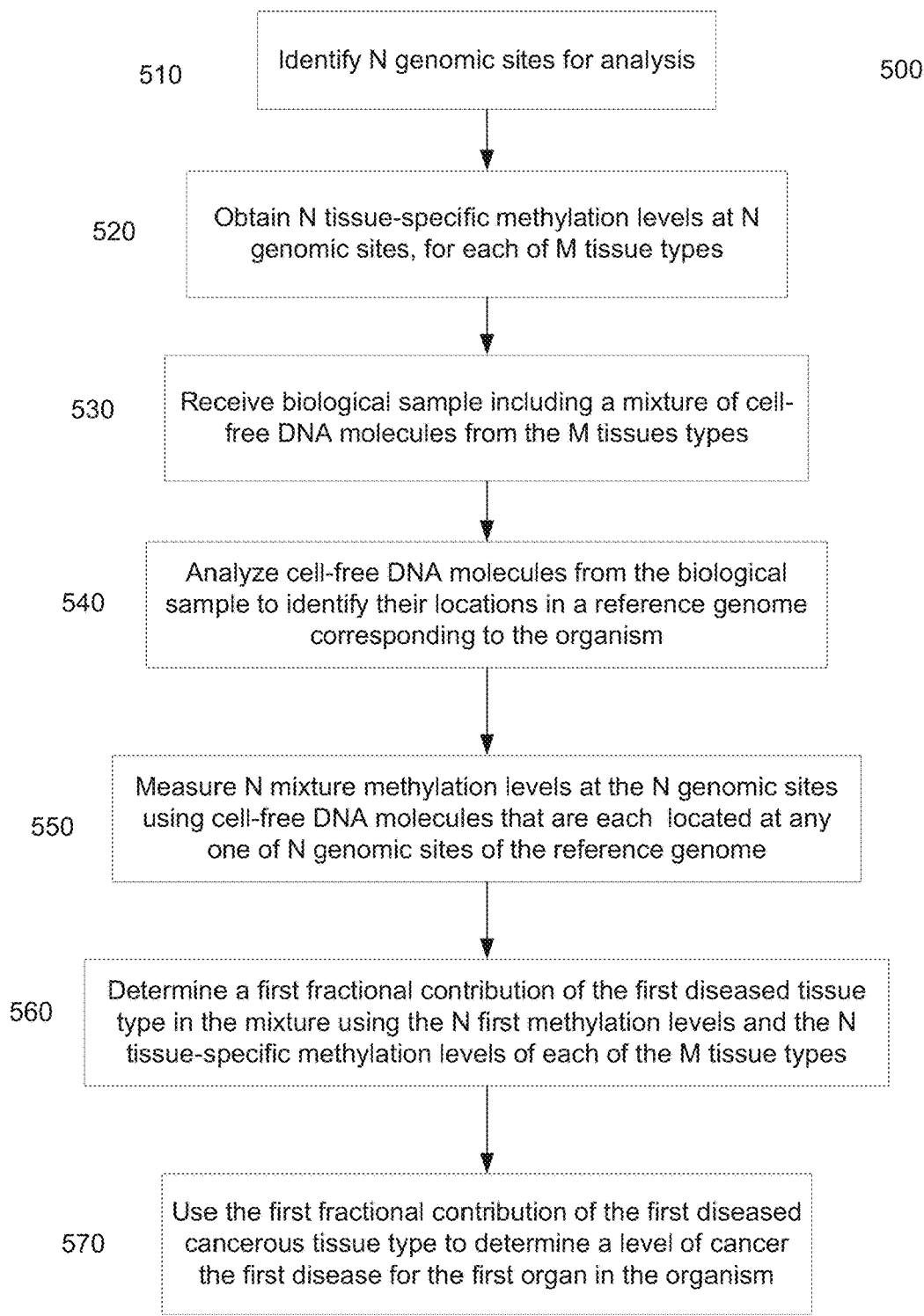
FIG. 5 is a flowchart illustrating a method 500 of analyzing a biological sample of an organism using a tissue-specific methylation pattern of a diseased tissue type according to embodiments of the present invention.

FIG. 5 is a flowchart illustrating a method 500 of analyzing a biological sample of an organism using a tissue-specific methylation pattern of a diseased tissue type according to embodiments of the present invention. The biological sample includes a mixture of cell-free DNA molecules from a plurality of tissues types, which include a first tissue type. Method 500 can be used to determine a level of a disease in a particular organ, e.g., for which a tissue-specific methylation pattern corresponding to diseased cells of that organ is used in the deconvolution. Method 500 can be performed using a computer system.

At block 510, N genomic sites are identified for analysis, where N is an integer. The N genomic sites can have various attributes, e.g., as described in more detail in section II, which describes type I and type II genomic sites. As examples, the N genomic sites can include type I or type II sites only, or a combination of both. The genomic sites can be identified based on analyses of one or more other samples, e.g., based on data obtained from databases about methylation levels measured in various individuals. In some embodiments, at least 10 of the N genomic sites are type II. The N genomic sites can also include type I sites (e.g., at least 10).

These methylation properties of the genomic loci can be measured for one sample or a set of samples. The set of samples may be for a subpopulation of organisms that includes the instant organism being tested, e.g., a subpopulation having a particular trait that is shared with the instant organism. These other samples can be referred to as reference tissues, and different reference tissues may be used from different samples.

At block 520, N tissue-specific methylation levels are obtained at the N genomic sites for each of M tissue types. N is greater than or equal to M, so that the tissue-specific methylation levels can be used in the deconvolution to determine the fractional percentages. The tissue-specific methylation levels can form a matrix A of dimensions N by M. Each column of the matrix A can correspond to a methylation pattern for a particular tissue type, where the pattern is of methylation levels at the N genomic sites.

For detection of a particular disease of an organ, one of the M tissue types can correspond to a first diseased tissue type corresponding to a first disease of a first organ. A second tissue type of the M tissue types can correspond to healthy tissue of the first organ. In various embodiments, the tissue-specific methylation patterns can be retrieved from public database(s) or previous studies. These tissue-specific methylation patterns can be used to identify the N genomic sites to be used in the deconvolution analysis.

At block 530, the biological sample including a mixture of cell-free DNA molecules from the M tissues types is received. The biological sample may be obtained from the patient organism in a variety of ways. The manner of obtaining such samples may be non-invasive or invasive. Examples of non-invasively obtained samples include certain types of fluids (e.g. plasma or serum or urine) or stools. For instance, plasma and urine include cell-free DNA molecules from multiple organ tissues, and is thus useful for analyzing multiple organs via one sample.

In some instances, the biological sample may include cellular DNA. For example, with a urine sample, the biological sample may include cellular DNA from the urine pellet. Cellular DNA is generally longer than cell-free DNA and a fragmentation process, such as sonication, may be used to produce shorter fragments for short read sequencing.

At block 540, cell-free DNA molecules from the biological sample are analyzed to identify their locations in a reference genome corresponding to the organism. For example, the cell-free DNA molecules can be sequenced to obtain sequence reads, and the sequence reads can be mapped (aligned) to the reference genome. If the organism was a human, then the reference genome would be a reference human genome, potentially from a particular subpopulation. As another example, the cell-free DNA molecules can be analyzed with different probes (e.g., following PCR or other amplification), where each probe corresponds to a different genomic site. In some embodiments, the analysis of the cell-free DNA molecules can be performed by receiving sequence reads or other experimental data corresponding to the cell-free DNA molecules, and then analyzing the experimental data.

A statistically significant number of cell-free DNA molecules can be analyzed so as to provide an accurate deconvolution for determining the fractional contributions from the M tissue types. In some embodiments, at least 1,000 cell-free DNA molecules are analyzed. In other embodiments, at least 10,000 or 50,000 or 100,000 or 500,000 or 1,000,000 or 5,000,000 cell-free DNA molecules or more can be analyzed. The total number of molecules to analyze can depend on M and N, and the desired precision (accuracy).

At block 550, N mixture methylation levels are measured at the N genomic sites using a first group (set) of cell-free DNA molecules that are each located at any one of N genomic sites of the reference genome. The N mixture methylation levels refer to methylation levels in the mixture of the biological sample. As an example, if a cell-free DNA molecule from the mixture is located at one of the N genomic sites, then a methylation index for that molecule at the site can be included in an overall methylation density for that site. The N mixture methylation levels can form a methylation vector b of length N, where b corresponds to observed values from which the fractional contributions of the tissue types can be determined.

In one embodiment, the methylation levels for the genomic sites in the DNA mixture can be determined using whole genome bisulfite sequencing. In other embodiments, the methylation levels for the genomic sites can be determined using methylation microarray analysis, such as the Illumina HumanMethylation450 system, or by using methylation immunoprecipitation (e.g. using an anti-methylcytosine antibody) or treatment with a methylation-binding protein followed by microarray analysis or DNA sequencing, or by using methylation-sensitive restriction enzyme treatment followed by microarray or DNA sequencing, or by using methylation aware sequencing e.g. using a single molecule sequencing method (e.g. by a nanopore sequencing (Schreiber et al., Proc Natl Acad Sci 2013; 110: 18910-18915) or by the Pacific Biosciences single molecule real time analysis (Flusberg et al., Nat Methods 2010; 7: 461-465)). Tissue-specific methylation levels can be measured in a same way. As other example, targeted bisulfite sequencing, methylation-specific PCR, non-bisulfite based methylation-aware sequencing (e.g. by single molecule sequencing platforms (Powers et al., Efficient and accurate whole genome assembly and methylome profiling of *E. coli*, BMC Genomics, 2013; 14:675) can be used for the analysis of the methylation level of the plasma DNA for plasma DNA methylation deconvolution analysis. Accordingly, methylation-aware sequencing results can be obtained in a variety of ways.

At block 560, a fractional contribution of the first diseased tissue type in the mixture is determined using the N first methylation levels and the N tissue-specific methylation levels of each of the M tissue types. In some embodiments, M values of a composition vector can be determined. Each M value corresponds to a fractional contribution of a particular tissue type of the M tissue types to the DNA mixture. The M values of the composition vector can be solved to provide the N mixture methylation levels (e.g., methylation vector b) given the N×M tissue-specific methylation levels. The M fractional contributions can correspond to a vector x that is determined by solving Ax=b, which can be solved in a variety of ways (e.g., matrix factorization and/or inversion, or by an optimization process), as will be appreciated by one skilled in the art. When N is greater than M, the solution can involve a minimization of errors, e.g., using least-squares.

The composition vector can be used determine an amount of each of the M tissue types in the mixture. The M values of the composition vector may be taken directly as the fractional contributions of the M tissue types. In some implementations, the M values can be converted to percentages. Error terms can be used to shift the M values to higher or lower values. Each of the values of the composition vector can be considered a component, and a particular component can correspond to a particular tissue type.

At block 570, the fractional contribution of the first diseased tissue type is used to determine a level of the first disease for the first organ in the organism. The fractional contribution can be compared to a cutoff value (threshold). For example, in FIG. 4C, the cutoff value can be 20. The cutoff value can be determined using samples from organisms that are healthy for the tissue type and diseased for the tissue type. The samples can have various levels of the first disease besides having or not having the first disease. One skilled in the art will appreciate how to determine desired cutoff values based on data measured from samples having a known level of the first disease.

Examples of the first organ can be a kidney (e.g., when urine is sample), a bladder (e.g., when urine is sample), a liver (e.g., when plasma or serum is sample), or a salivary gland (e.g., when saliva is sample). Examples of the first disease can be cancer, glomerulonephritis when the first organ is the kidney, or nephrotic syndrome when the first organ is the kidney.

In some embodiments, reference patterns can be used for multiple diseased tissues, potentially from a same organ or a different organ. In this manner, multiple disease types can be measured at the same time.

In some embodiments, the fractional contribution could be used to determine an index value, which can be compared to a cutoff value. A fractional contribution is limited to a particular range, and the sum of the contributions would equal 100%. Thus, when a contribution increases, it is at the expense of others. An index value can have a larger range, and not be dependent on the contributions of other tissue types. The index value may be the fractional contribution multiplied by the total cfDNA genome equivalents (GE) per milliliter of urine, termed the bladder tumor GE index.

Figure 6B:
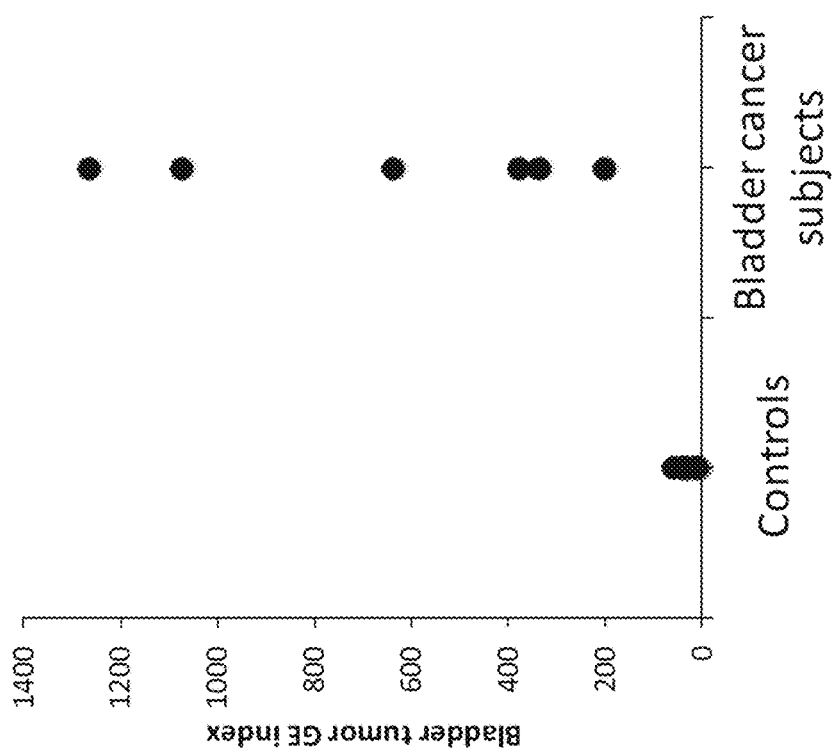
FIG. 6B shows the bladder tumor GE index values for six bladder cancer cases and six controls according to embodiments of the present invention.
Figure 6A:
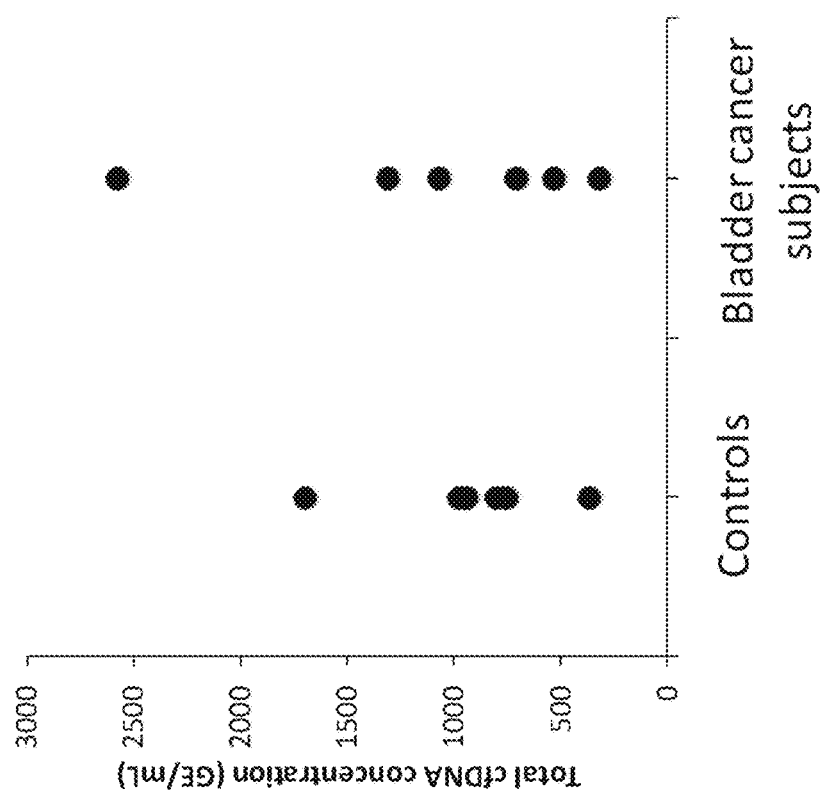
FIG. 6A shows the total cfDNA concentration in genome equivalents (GE) per milliliter of urine for six bladder cancer cases and six controls according to embodiments of the present invention.

As shown in FIG. 6A, six cases and six controls showed no statistical difference between the total cell-free DNA concentration in urine as measured in GE/ml. As shown in FIG. 6B, when the determined fractional contribution of bladder tumor tissue was multiplied by total GE/ml (bladder tumor GE index) to calculate an index value, the index value was significantly higher in bladder cancer cases compared to controls.

In some embodiments, the fractional contribution can be used to adjust the number and amplitude of CNAs and/or hypomethlyation identified in urine to calculate a new index value.

II. SIZE OF URINARY CFDNA

The length of cfDNA fragments can be ascertained to single base pair resolution using whole genome sequencing. Specifically, the length of urinary cfDNA can be determined at single base pair resolution using paired end massively parallel sequencing and visualized in a size profile plot of the frequency at different fragment lengths. The majority of urinary cfDNA fragments are relatively short. In the void urine of normal controls, the median cfDNA fragment length is 65-80 bp. Visualization of the frequency of cfDNA fragments at different lengths in a size profile analysis reveals a distinct 10 bp periodicity in cfDNA fragments <100 bp, where the frequency of the peaks are up to three times that of the troughs.

As discussed below, the data from paired samples from the renal pelvis and voided urine suggest that there is a larger proportion of long cfDNA fragments in the upper urinary tract. In vitro incubation experiments suggest that cfDNA is degraded in the urinary tract under first order kinetics. This is reflected in the size profile by a reduced proportion of long fragments and the accentuation of the 10 bp periodicity in the 50-80 bp range. The 10 bp periodicity observed in urinary cfDNA is reminiscent of that seen in plasma (36,37), albeit at a larger amplitude in urine compared with plasma. Although this degradation process affects the global methylation density and also causes fluctuation in the methylation deconvolution results, the high degree of correlation observed in the voided urine of transplant patients suggests that the methylation deconvolution process is robust despite in vivo degradation.

A. Size of Urinary cfDNA in HSCT and Renal Transplant Patients

Our previous study showed that fetal-derived urinary cfDNA fragments were shorter than maternally-derived fragments (Tsui et al. PLos One 2012). Here, we investigate the size of transplant urine cfDNA fragments, particularly if allograft-derived cfDNA would be a different size profile compared to recipient derived fragments.

Figure 7B:
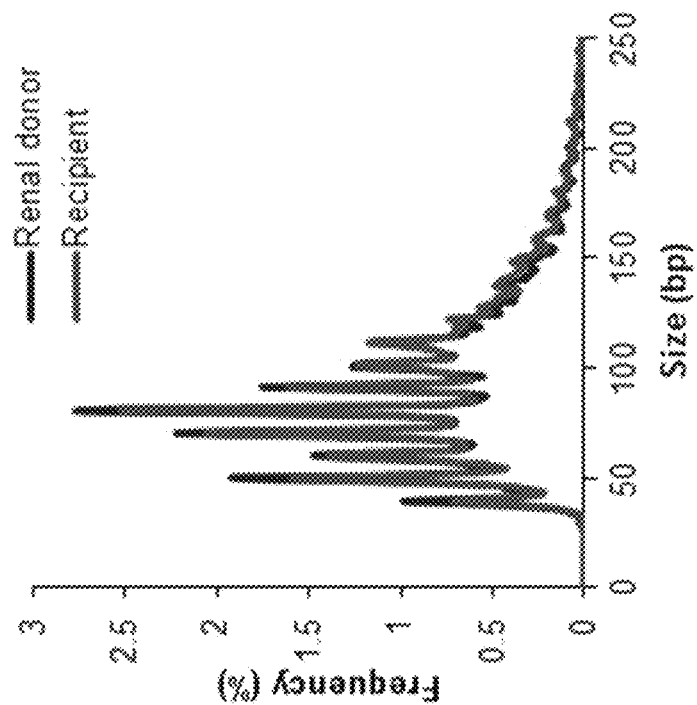
FIGS. 7A and 7B show urinary cfDNA size profiles of recipient and donor DNA from a representative HSCT patient (FIG. 7A) and a renal transplant patient (FIG. 7B) according to embodiments of the present invention.
Figure 7A:
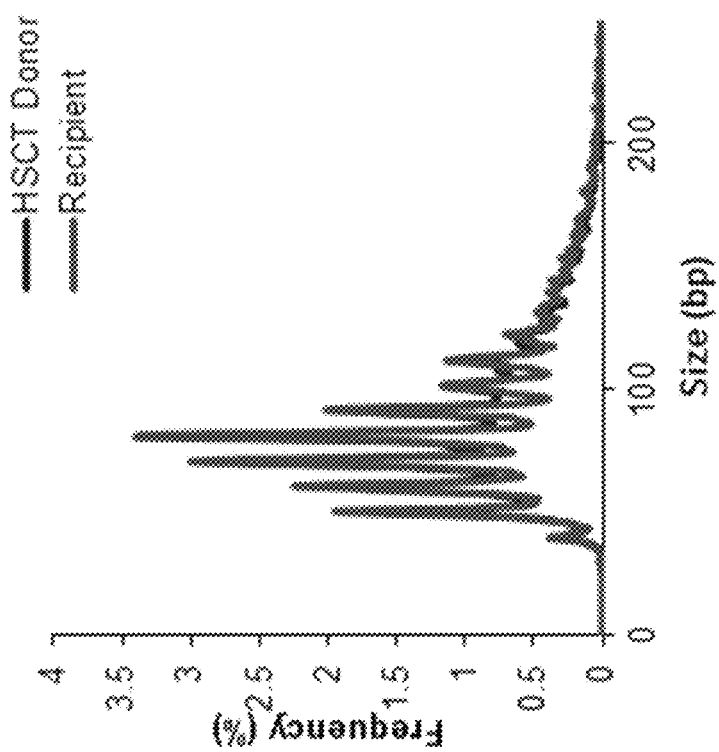

FIGS. 7A and 7B show urinary cfDNA size profiles of recipient and donor DNA from a representative HSCT patient (FIG. 7A) and a renal transplant patient (FIG. 7B) according to embodiments of the present invention. The x-axis displays the size in single base pair resolution and the y-axis shows the frequency at each length. Donor and recipient size profiles are colored in blue and red, respectively.

The urine samples from the 31 HSCT and renal transplant patients show a similar pattern, with a median length of 81 bp and a distinct 10 bp periodicity at lengths that are a multiple of 10, especially at the 50-80 bp range. After separation of donor and recipient specific size profiles from HSCT (FIG. 7A) and kidney transplant (FIG. 7B) patients, there was no observable difference between the size of urinary cfDNA originating from the donor haematopetic and kidney tissue compared with recipient tissue. Accordingly, the size profiles of donor specific cfDNA from allogeneic hematopoetic cells and kidney are almost identical to the size profile of cfDNA from the recipient.

This may suggest that cfDNA released from hematopoetic and kidney tissue are of a similar size as recipient tissue, or that the degradative environment of the urinary tract causes cfDNA released from different tissues to assume a common size profile after a certain period of time. Although both hematopoietically-derived and fetal-derived cfDNA contribute to urine via kidney filtration of plasma, hematopoietic cells in the urinary tract may contribute cfDNA directly into the urine, accounting for the difference between their size profiles.

B. Size and Composition of Urinary cfDNA in the Renal Pelvis Vs Voided Urine

The size and composition of plasma cfDNA appears to attain equilibrium during circulation and remains largely consistent with repeat sampling of peripheral blood. In contrast, urine is produced in the kidneys and it unidirectionally descends via the ureters into the bladder, where it is stored before it is voided.

Since DNaseI is highly expressed in the kidney and bladder (proteinatlas.org/) and is present (29) and highly active in urine (30), we investigated if cfDNA fragments would be of a different size in the renal pelvis compared with the voided urine. We obtained urine samples from a patient who suffered from a 2 cm ureteric stone causing complete obstruction of the right-sided urinary system and requiring the insertion of a percutaneous nephrostomy (tube into a kidney pelvis where urine is formed) that drained urine directly from the renal pelvis. The left sided kidney produced urine as normal that was voided via the urinary tract. The stone caused a complete obstruction of the right side. We collected urine simultaneously from the renal pelvis of the right kidney and the voided urine on two occasions and found that urine from the renal pelvis had a larger proportion of long fragments. The second occasion was after inflammation had decreased in the kidney pelvis.

Figure 8B:
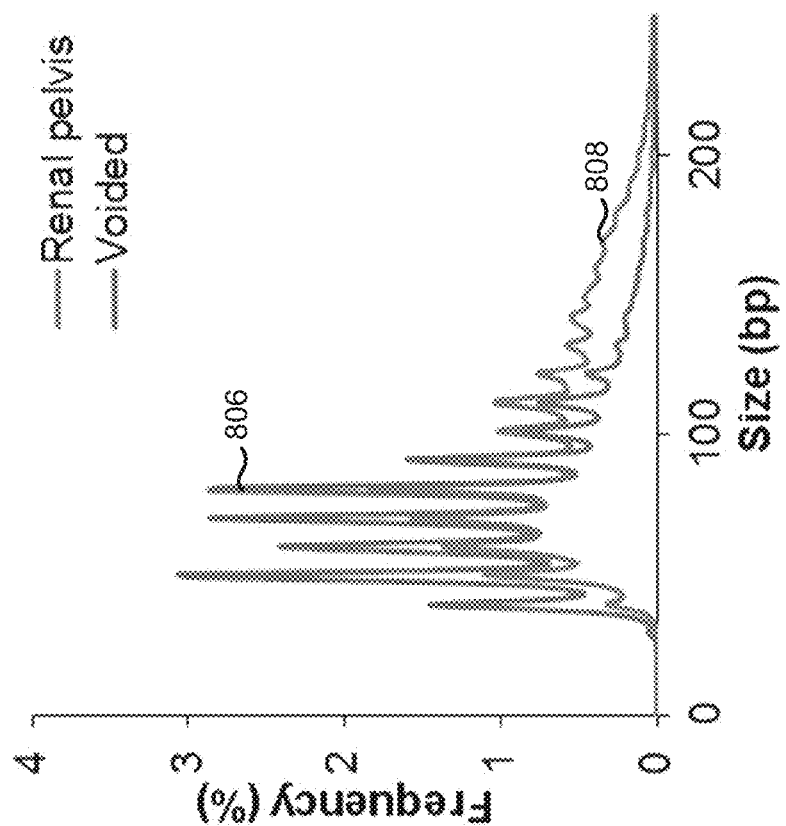
FIGS. 8A and 8B show size profiles of cfDNA from the kidney pelvis of the right kidney, which was blocked due to a stone, and void urine from the left kidney according to embodiments of the present invention.
Figure 8A:
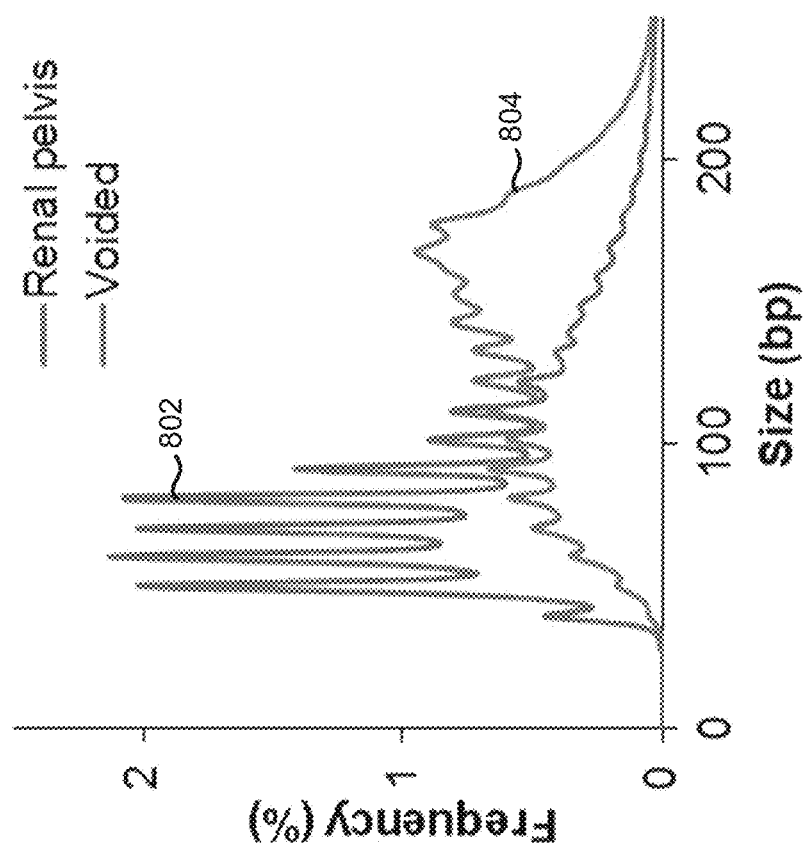

FIGS. 8A and 8B show size profiles of cfDNA from the kidney pelvis of the right kidney, which was blocked due to a stone, and void urine from the left kidney according to embodiments of the present invention. The size profiles of urinary cfDNA are from paired samples from the renal pelvis and voided urine on two occasions 37 days apart. FIG. 8A represents the kidney pelvis and void urine collected five days after percutaneous nephrolithotomy (PCN) insertion. FIG. 8B represents urine samples collected 42 days after PCN insertion, which is after the patient had recovered. The X-axis displays the size in single base pair resolution, and the Y-axis shows the frequency of uniquely mappable fragments at a particular length. Lines 802 and 806 represent voided urine produced by the left kidney. Lines 804 and 808 represent urine from the right renal pelvis collected simultaneously.

On both occasions, there is a larger proportion of long urinary cfDNA fragments in the kidney pelvis urine compared with void urine, and reduced amplitude of periodicity in the 50-80 bp range. Further, the average length of the urinary cfDNA fragments for the initial sample (FIG. 8A) is longer than the average length of the urinary cfDNA fragments for the later sample (FIG. 8B), which occurred after inflammation reduced in the right kidney.

Methylation deconvolution results for kidney pelvis and void urine show that there is a significant contribution from neutrophils in all four urine samples, with a higher proportional contribution in kidney pelvis urine compared with void urine (Table 3). CfDNA fragments bearing the methylation signature of neutrophils could either be of pre-renal origin from the plasma, or from white cell aggregates in the kidney pelvis. There is also a higher global methylation density across CpG sites in kidney pelvis urine compared with voided urine.

TABLE 3

|  | Neutrophil (%) | T-cell (%) | B-cell (%) | Kidney (%) | Urothelium (%) | Global CpG Methylation density (%) |
| --- | --- | --- | --- | --- | --- | --- |
| A Kidney Pelvis | 89.8 | 1.2 | 2.6 | 0.0 | 6.4 | 75.0 |
| A Void | 80.7 | 0.0 | 2.4 | 10.7 | 6.3 | 71.2 |
| B Kidney Pelvis | 77.9 | 2.2 | 2.3 | 5.4 | 12.3 | 74.1 |
| B Void | 52.0 | 0.0 | 3.9 | 16.9 | 27.2 | 64.3 |

Table 3 table displays the proportional contribution from each tissue by methylation deconvolution and the global methylation density at CpG sites for cfDNA from the kidney pelvis and void urine. A and B correspond to the paired right kidney pelvis and void urine samples displayed in FIGS. 8A and 8B.

C. Change in Size Profile of Urinary cfDNA from Renal Pelvis Over Time

By sampling urine from different parts of the urinary tract, we found that there is a larger proportion of long cfDNA fragments in the kidney pelvis. As the urine descends the urinary tract, there is a decrease in the absolute concentration of cfDNA, and an increase in the proportion of shorter fragments with a characteristic 10 base pair (bp) periodicity that is most pronounced between 50-80 bp.

1. Renal Pelvis Urine Incubated Over Time

Some of the differences observed between kidney pelvis urine and void urine may be due to the in vivo degradation of cfDNA. After observing the differences between kidney pelvis and void urine on the first occasion (FIG. 8A), for the second collection (FIG. 8B), we collected a larger volume of kidney pelvis urine and the additional urine was put into a sealed container and incubated at 37° C. The in vitro incubation of kidney pelvis urine mimics the in vivo passage of urine in the urinary tract and storage in the bladder. Urine was drawn out of the container and processed at 3 hours, 6 hours and 24 hours of incubation.

Figure 9B:
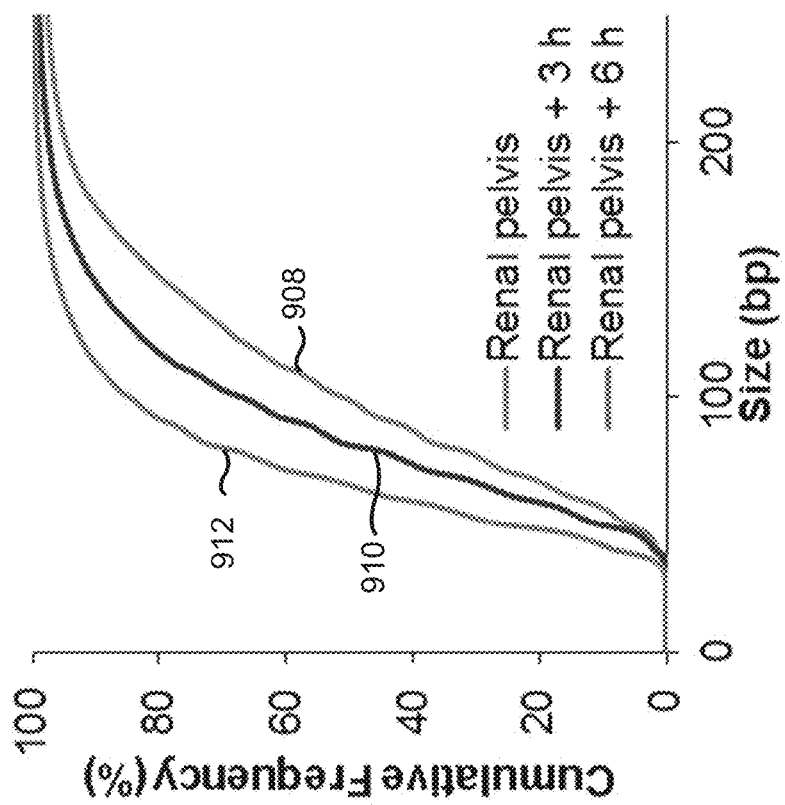
FIGS. 9A and 9B are the size profiles of cfDNA from urine from the renal pelvis at 0, 3, and 6 hours of in vitro incubation at 37° C. according to embodiments of the present invention.
Figure 9A:
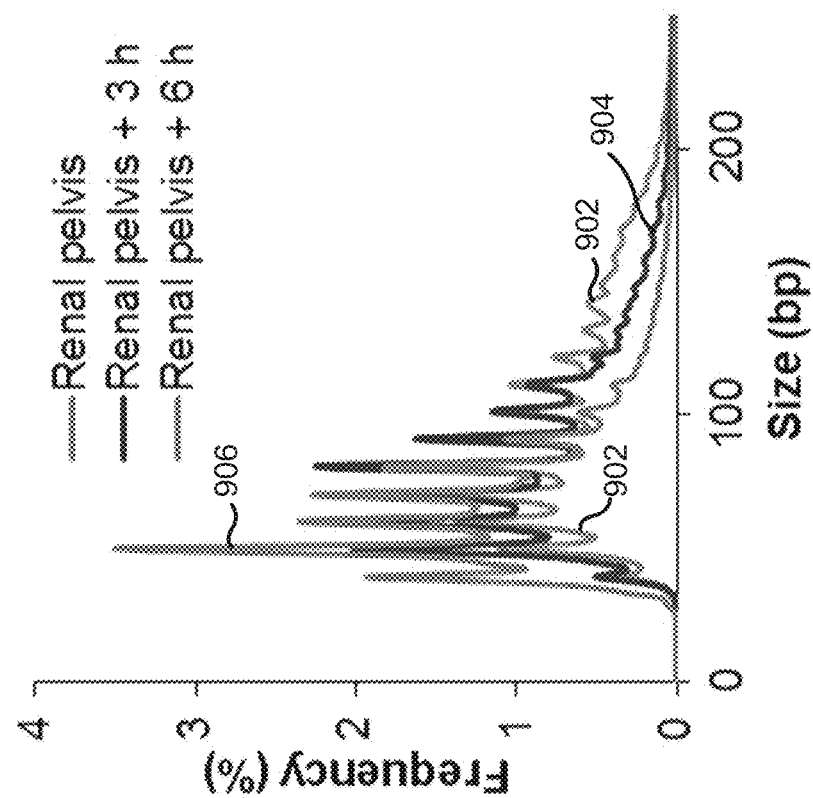

FIGS. 9A and 9B are the size profiles of cfDNA from urine from the renal pelvis at 0, 3, and 6 hours of in vitro incubation at 37° C. FIG. 9A displays the frequency at each base pair length, and FIG. 9B displays the cumulative frequency. Lines 902 and 908 represent the size profiles of cfDNA at the time of collection. Lines 904 and 910 represent the size profiles after 3 hours of incubation. Lines 906 and 912 represent the size profiles after 6 hours of incubation. These graphs illustrate the increase in the amplitude of the 10 bp periodicity and a reduction in the proportion of long cfDNA fragments with in vitro incubation. As can be seen, after 3 and 6 hours of incubation, the size profiles of these samples displayed a progressive reduction in the proportion of long fragments and an increase in amplitude of the 10 bp periodicity in the 50-80 bp region. This in vitro incubation of cfDNA from urine from the kidney pelvis shows that even in the absence of contact with the urinary tract, incubation at 37° C. causes a decrease in the concentration of cfDNA, a larger proportion of short cfDNA, and an increased 10 bp periodicity. The size profile of kidney pelvis urine resembles that of void urine after incubation at 37° C. for 3 to 6 hours.

Figure 10B:
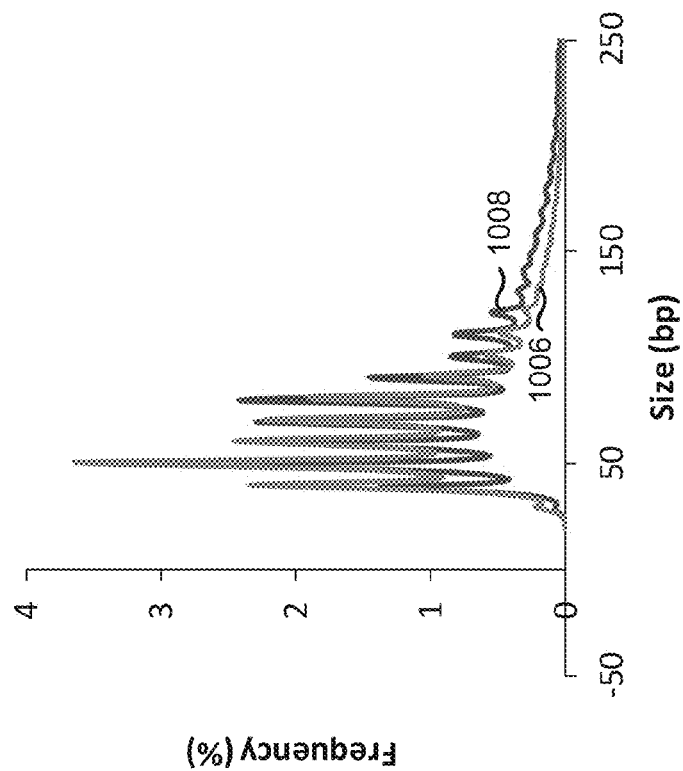
FIGS. 10A and 10B show the size profile of void urine compared with that of kidney pelvis urine incubated for (a) 3 hours and (b) 6 hours according to embodiments of the present invention.
Figure 10A:
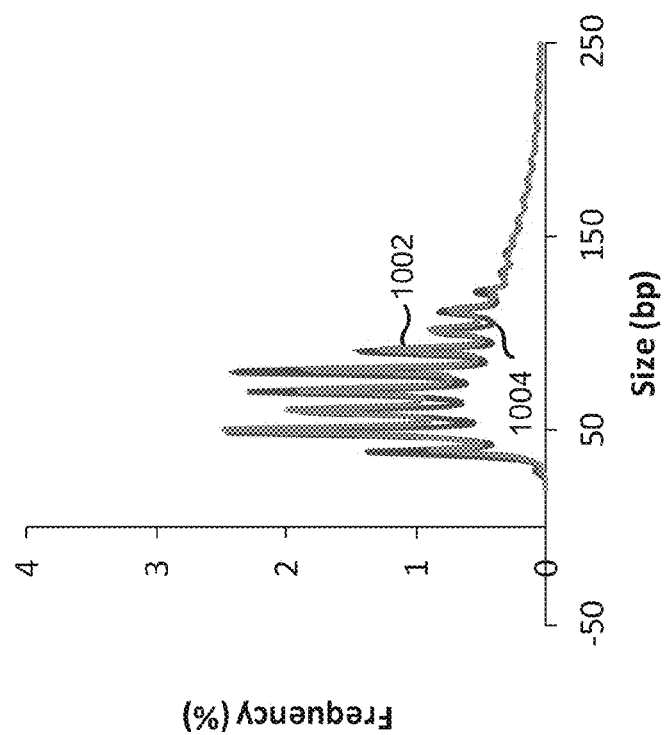

FIGS. 10A and 10B show the size profile of void urine compared with that of kidney pelvis urine incubated for (a) 3 hours and (b) 6 hours. Line 1002 represents kidney pelvis urine incubated for 3 hours. Lines 1004 and 1008 represent voided urine. Line 1006 represents kidney pelvis urine incubated for 6 hours. As can be seen, the size profile of void urine is highly similar to that of kidney pelvis incubated for 3 and 6 hours. These data suggest that during the in vivo passage of urine from the kidney pelvis down the urinary tract, there is likely to be a degradation process that reduces the concentration of cfDNA and shortens the length of cfDNA fragments.

2. Relation of Different Size Parameters to Each Other

The length of the urinary cfDNA fragments from a single urine sample, and thus the degree of degradation of urinary cfDNA can be characterized using several quantitative measures: the median length, proportion of fragments longer than 70 bp (labeled as P>70 bp), and a fragmentation (periodicity) index. The proportion of fragments longer than 70 bp (P>70 bp) can be determined as the number of fragments longer than 70 bp is divided by the total number of fragments and expressed as a percentage.

The 10 bp periodicity is most pronounced between 50 and 80 bp, and the amplitude of the periodicity can be represented by the difference in frequency between the peak lengths at 50, 60, and 70 bp and the trough lengths at 55, 65, and 75 bp. This can be represented as a periodicity index (PI). The periodicity index may represent a difference in the frequency of DNA fragments at the plurality of peak lengths in the size profile from the frequency of DNA fragments at the plurality of trough lengths in the size profile. The plurality of peak lengths may be present at regular size intervals. The plurality of trough lengths may be present at regular size intervals offset from the plurality of peak lengths. For example, the regular size interval may be 10 bp, but the trough lengths may be offset (or out of phase) with the peak lengths by 5 bp. An example of a periodicity index can be calculated as follows:

$$PI=(F(50)+F(60)+F(70))-(F(55)+F(65)+F(75))$$

where F50, F60 F70, F55, F65, and F75 represent the frequency of cfDNA fragments at that particular length. A high periodicity index represents a large difference in the frequency between cfDNA fragments at the peaks compared with the troughs and thus, a larger amplitude of periodicity. As shown in FIGS. 10A and 10B, the 10 bp periodicity was most pronounced between 50 and 80 bp, and the amplitude of the periodicity could be represented by the difference in the sum of the frequency between the peak lengths at 50, 60, and 70 bp and the sum of the trough lengths at 55, 65, and 75 bp.

Figure 11B:
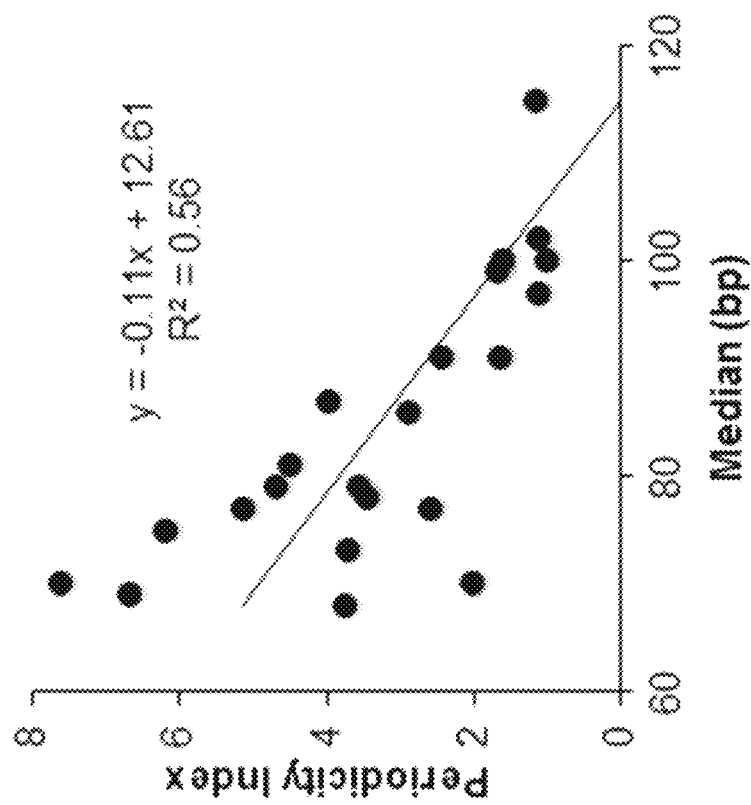
FIGS. 11A and 11B are graphs displaying the relationship between cfDNA fragment size parameters for the 31 HSCT and renal transplant urine samples according to embodiments of the present invention.
Figure 11A:
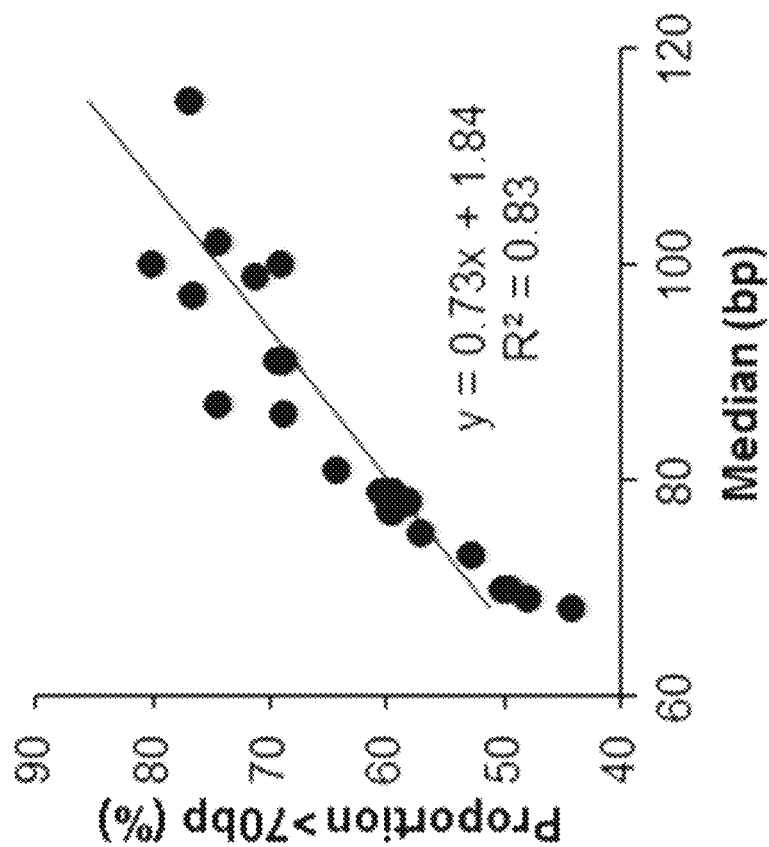

FIGS. 11A and 11B are graphs displaying the relationship between cfDNA fragment size parameters for the 31 HSCT and renal transplant urine samples. The parameters are median (bp), proportion >70 bp ($P_{>70}$) and periodicity index (PI). FIG. 11A shows there is a strong positive correlation between the median length and $P_{>}70$. FIG. 11B shows there is a negative (inverse) correlation between the median and PI, and thus also with P>70 bp. This latter observation reinforces the notion that length and periodicity of cfDNA fragments are related and represent the degree of degradation each sample.

The changes seen in the kidney pelvis urine with incubation seen in the size profile is reflected by the decreasing median, decreasing P>70 bp and increase in the PI (Table 4). The median, P>70 bp and PI of the kidney pelvis urine become very comparable to that of the paired void urine after incubation for 3-6 hours.

TABLE 4

|  | Median (bp) | $P_{>70\,bp}$ (%) | PI |
|---|---|---|---|
| Renal Pelvis | 99 | 75.8 | 2.0 |
| Renal Pelvis + 3 h | 81 | 64.2 | 3.4 |
| Renal Pelvis + 6 h | 65 | 42.3 | 4.7 |
| Voided Urine | 72 | 53.8 | 6.0 |

Table 4 shows the summary size statistics in the form of the median in base pairs (bp), the proportion of fragments more than 70 bp ($P_{>70}$), and the Periodicity Index (PI) for urinary cfDNA from the renal pelvis, during 37° C. in vitro incubation and paired voided urine. Comparison between the kidney pelvis urine, void urine and kidney pelvis urine incubated in vitro at 37° C. for 3 and 6 hours shows that kidney pelvis urine has a higher median, P>70 and lower FI compared with void urine. Kidney pelvis urine is degraded if it is kept at 37° C. such that the proportion of shorter fragments increases and a more pronounced periodicity seen as a larger difference between the peaks and troughs at 50-75 bp. As urine from the renal pelvis was fragmented during the in vitro incubation, there was a progressive reduction in the median P>70 and an increase in the PI.

The in vitro incubation results explain the size profile commonly observed in void urine and provides evidence that fragmentation of cfDNA fragments occurs in the urinary tract. This informs us that the size and concentration of urinary cfDNA can be affected by i) the site of urine collection, and ii) the duration that the urine was in vivo.

3. Methylation and Composition Over Time

Interestingly, the global CpG site methylation density is higher in kidney pelvis urine compared with void urine, and there is a gradual decrease in global CpG site methylation density as the kidney pelvis is incubated at 37° C. Given the changes in absolute concentration, fragment size, and global CpG site methylation density of urinary cfDNA during in vitro incubation, we assessed if these factors would affect methylation deconvolution. The overall methylation density and proportional contribution by different tissues by methylation deconvolution of urinary cfDNA in the renal pelvis fluctuates during in vitro incubation at 37° C., but the proportional contribution from the blood cells, kidney and urothelium remain constant in terms of the ranking (Table 5).

TABLE 5

Methylation deconvolution results for the proportional contribution of neutrophils, T-cells, B-cells, kidney and urothelium in kidney pelvis urine, kidney pelvis urine during 37° C. in vitro incubation incubation and paired void urine.

|  | Neutrophils | T-cells | B-cells | Kidney | Urothelium | Global CpG Methylation Density (%) |
|---|---|---|---|---|---|---|
| Renal Pelvis | 77.9 | 2.2 | 2.3 | 5.4 | 12.3 | 74.1 |
| Renal Pelvis + 3 h | 61.4 | 9.9 | 5.0 | 8.1 | 15.6 | 72.2 |
| Renal Pelvis + 6 h | 74.1 | 4.3 | 3.5 | 6.4 | 11.8 | 68.9 |
| Voided Urine | 52.0 | 0.0 | 3.9 | 16.9 | 27.2 | 64.3 |

Table 5 displays the proportional contribution from each tissue by methylation deconvolution and the global methylation density at CpG sites for cfDNA during the in vitro incubation at 37° C. The global methylation density was reduced from 74.1 to 68.9% over 6 hours, and there was a fluctuation in the methylation deconvolution contributions. However, the proportional contribution from the blood cells (neutrophils, T-cells, and B-cells), kidney, and urothelium remain constant in terms of the ranking.

The methylation deconvolution results for kidney pelvis urine during in vitro incubation showed that blood cells (neutrophils) were the predominant contributor at 0, 3, and 6 hours, with slight fluctuation in contribution percentages from the different tissues. Methylation deconvolution results for the paired voided urine also showed predominant neutrophil contribution with a slightly higher contribution from urothelium compared with the kidney pelvis urine samples. The higher urothelium contribution may reflect the urine acquiring urothelial cfDNA from a longer stretch of the urinary tract.

D. Change in Concentration of Urinary cfDNA Over Time

Since the size profile of urinary cfDNA fragments in the kidney pelvis had a higher proportion of longer fragments, we investigated the effects of in vitro incubation of kidney pelvis urine at 37° C. Kidney pelvis urine was collected via PCN and kept at 37° C., with aliquots taken at different time points to ascertain the absolute cfDNA concentration by qPCR, and also the size profile from each time point.

The concentration of kidney pelvis urine cfDNA was quantified using qPCR for a 62 bp LEP gene region, and quantification was done at time zero, and for each incubation time point. There is a decrease in total DNA concentration over time, with a larger decrease during the initial time period (FIG. 12A). If an exponential decay curve is fit, then urinary cfDNA is estimated to have a half-life of 4.9 hours and a mean lifetime of 7.0 hours.

We then assessed if the degradation and fragmentation patterns observed in kidney pelvis urine could also be seen in control void urine if it is kept at 37° C. We collected about 200 ml urine from the second urine void of the day, and incubated the urine in vitro at 37° C. for up to 12 hours. The concentration of cfDNA in normal controls is variable. Here, we display the results of the urine incubation for the control urine sample with the highest cfDNA concentration. The concentration of cfDNA in void urine decreases over time in a similar manner to kidney pelvis urine, and an exponential decay curve can be fitted for an $R^2$ of 0.92, with an estimated half-life of 3.5 hours and mean lifetime of 5.1 hours (FIG. 12B).

Thus, the shortening of cfDNA fragments during in vitro incubation is also reflected in the reduction of cfDNA concentration over time as quantified by qPCR (FIG. 12A). A similar pattern of exponential reduction is observed in the in vitro incubation of the voided urine of a normal subject (FIG. 12B), suggesting that cfDNA is fragmented in a time dependent manner with a half-life of 3.5-4.9 hours.

Figure 12B:
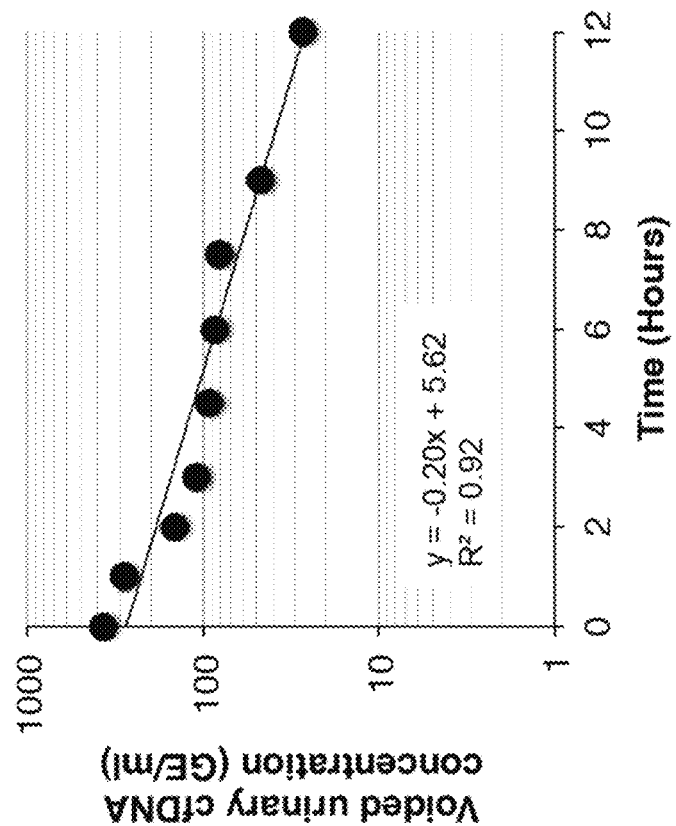
FIGS. 12A and 12B show the concentration of urinary cfDNA during the 37° C. in vitro incubation experiments for urine from the renal pelvis (FIG. 12A) and voided urine (FIG. 12B) according to embodiments of the present invention.
Figure 12A:
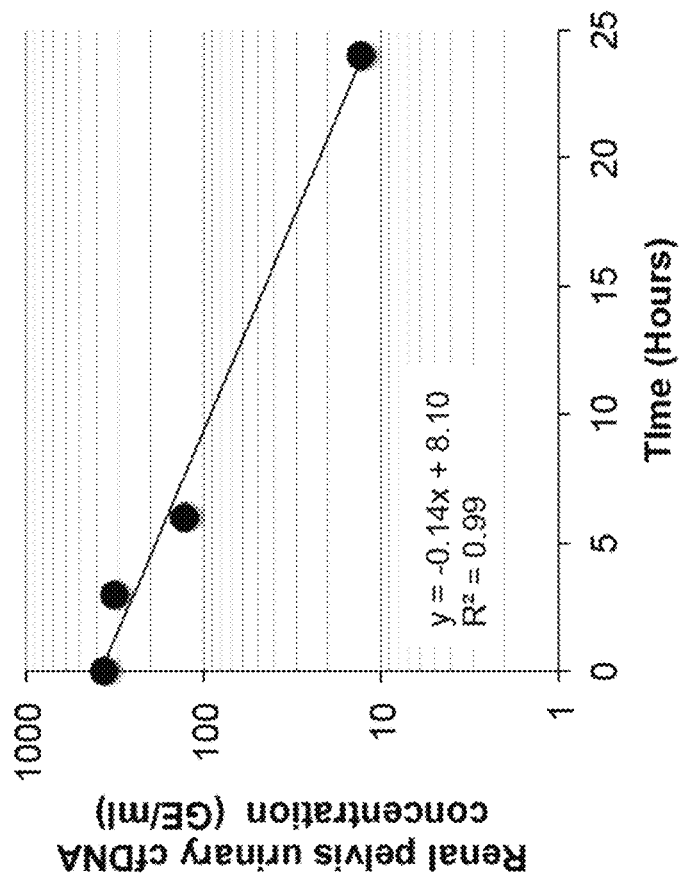

FIGS. 12A and 12B show the concentration of urinary cfDNA during the 37° C. in vitro incubation experiments for urine from the renal pelvis (FIG. 12A) and voided urine (FIG. 12B). The x-axis is the concentration of cfDNA in GE/ml urine displayed in a log scale, and the y-axis is the incubation time in hours. cfDNA appears to be degraded under first order kinetics in both renal pelvis and void urine with a half-life of 3.5-4.9 hours. The rate of degradation may vary between individuals.

E. Size Change in Voided Urinary cfDNA Over Time

The change in size of voided urine over time was investigated. Adequate DNA was collected at 3 hour intervals for non-bisulphite sequencing. Surprisingly, the sequential size profiles of cfDNA from 0 to 12 hours remains static and typical of that of voided urine. The fact that the size profile of voided cfDNA from the control subject remains constant for up to 12 hours of incubation at 37° C. suggests that a stable size profile is maintained after a certain point. This stable size profile is the pattern that is most commonly observed in voided urine samples.

Figure 13A:
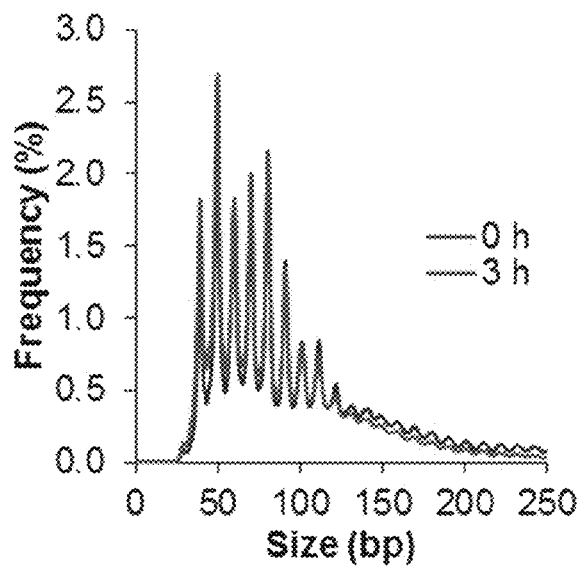
FIGS. 13A-13D. The size profiles of voided urine cfDNA with in vitro incubation at 37° C. from 0 to 12 hours according to embodiments of the present invention.
Figure 13B:
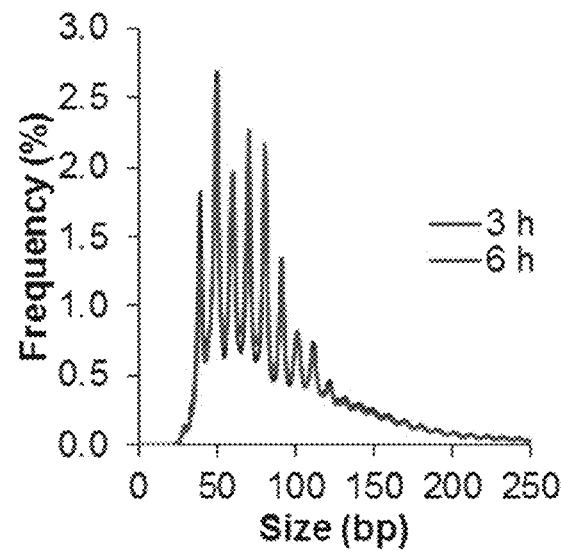
Figure 13C:
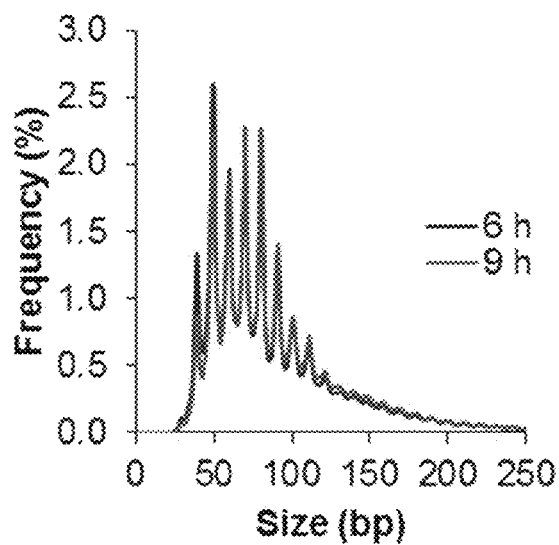
Figure 13D:
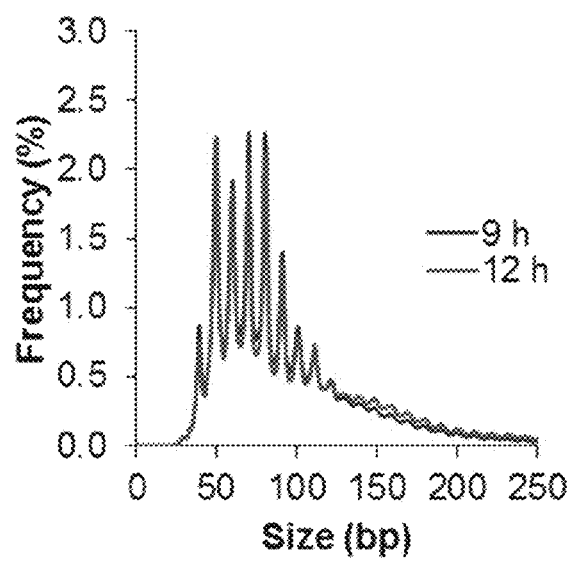

FIGS. 13A-13D. The size profiles of voided urine cfDNA with in vitro incubation at 37° C. from 0 to 12 hours. Urine was aliquoted from the incubation container and processed at 3 hours intervals. FIGS. 13A-13D show the concurrent reduction in cfDNA concentration as measured by qPCR. FIG. 13A shows the size profiles at 0 and 3 hours. FIG. 13B shows the size profiles at 3 and 6 hours. FIG. 13C shows the size profiles at 6 and 9 hours. FIG. 13D shows the size profiles at 9 and 12 hours. Despite the exponential decay seen in cfDNA concentration in FIG. 12B, the size profiles of these urine samples remain constant over the 12 hour incubation.

Accordingly, the parallel size profiles in the incubation of kidney pelvis urine show a reduction in the proportion of long fragments and accentuation of the 10 bp periodicity (FIG. 9A). However, parallel size profiles of the incubation of void urine shows that the typical void urine size profile (FIGS. 13A-13D) appears to represent a stable end point. After this point, cfDNA fragments of different lengths are degraded at a similar rate and the size profile remains constant despite the continual reduction in total cfDNA.

F. Method of Determining Inflammation from Long Fragments

Imaging may be able to identify a kidney stone, but it is difficult to determine a level of inflammation in a kidney from imaging, e.g., MRI or CT scans.

Figure 14:
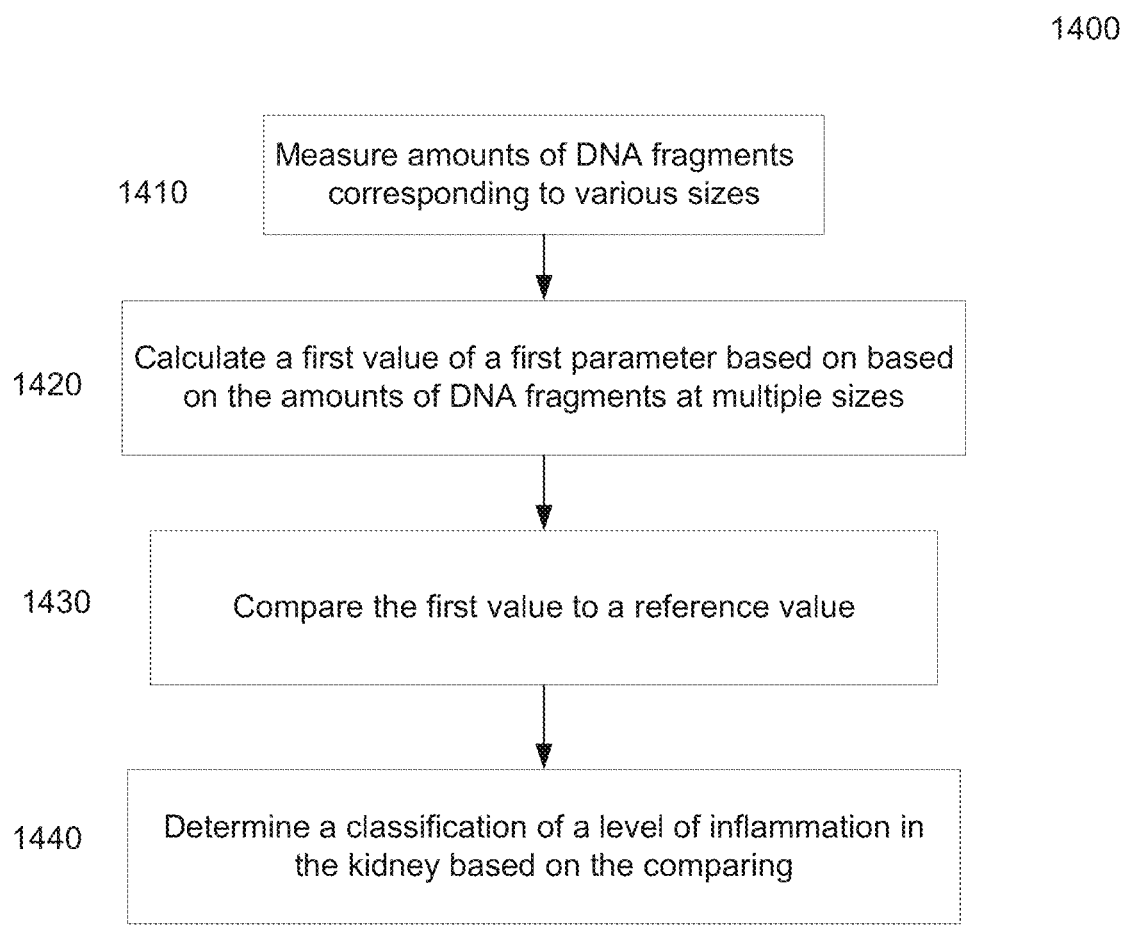
FIG. 14 is a flowchart of a method 1400 of analyzing a urine sample from a renal pelvis of a kidney of an organism to determine an extent of organ damage (e.g., a level of inflammation) according to embodiments of the present invention.

FIG. 14 is a flowchart of a method 1400 of analyzing a urine sample from a renal pelvis of a kidney of an organism to determine an extent of organ damage (e.g., a level of inflammation) according to embodiments of the present invention. At least some of the DNA are cell-free in the urine sample. Method 1400 may be performed wholly or partially with a computer system, as can certain other methods described herein.

Method 1400 can use a size distribution to determine a level of inflammation (an example of a level of a condition). The size distribution of plasma DNA can be determined, for example, but not limited to, using real-time PCR, electrophoresis and mass spectrometry analysis. In various embodiments, the measured size is a length, a molecular mass, or a measured parameter that is proportional to the length or mass, such as the mobility in a electrophoretogram and the time required to travel a fixed distance in electrophoresis or mass spectrometer. In another example, one can stain the DNA with an intercalating fluorescence dye, e.g. ethidium bromide or SYBR Green, where the amount of dye bound will be proportional to the length of the DNA molecule. One can determine the amount of dye bound by the intensity of the emitted fluorescence when UV light is shone on the sample.

At block 1410, amounts of DNA fragments corresponding to various sizes are measured. For each size of a plurality of sizes, an amount of a plurality of DNA fragments from the urine sample corresponding to the size can be measured. For instance, the number of DNA fragments having a length of 140 bases may be measured. The amounts may be saved as a histogram. In one embodiment, a size of each of the plurality of nucleic acids from the biological sample is measured, which may be done on an individual basis (e.g., by single molecule sequencing or paired-end sequencing and alignment to a reference) or on a group basis (e.g., via electrophoresis). The sizes may correspond to a range. Thus, an amount can be for DNA fragments that have a size within a particular range.

The plurality of DNA fragments may be chosen at random. For example, DNA fragments may be randomly sequenced. In some embodiments, a pair of sequence reads resulting from a DNA fragment can be aligned to a genome corresponding to the subject (e.g., a reference human genome) to determine a length of the DNA fragment. In various embodiments, the size can be mass, length, or other suitable size measures. The measurement can be performed in various ways, as described herein. For example, paired-end sequencing and alignment of DNA fragments may be performed, or electrophoresis may be used. A statistically significant number of DNA fragments can be measured to provide an accurate size profile of the biological sample. Examples of a statistically significant number of DNA fragments include greater than 100,000; 1,000,000; 2,000,000, or other suitable values, which may depend on the precision required.

In one embodiment, the data obtained from a physical measurement, such as paired-end sequencing or electrophoresis, can be received at a computer and analyzed to accomplish the measurement of the sizes of the DNA fragments. For instance, the sequence reads from the paired-end sequencing can be analyzed (e.g., by alignment) to determine the sizes. As another example, the electropherogram resulting from electrophoresis can be analyzed to determines the sizes. In one implementation, the analyzing of the DNA fragments does include the actual process of sequencing or subjecting DNA fragments to electrophoresis, while other implementations can just perform an analysis of the resulting data.

At block 1420, a first value of a first parameter is calculated based on the amounts of DNA fragments at multiple sizes. In one aspect, the first parameter provides a statistical measure of a size profile (e.g., a histogram) of DNA fragments in the biological sample. The parameter may be referred to as a size parameter since it is determined from the sizes of the plurality of DNA fragments. In one embodiment, the first parameter increases with increasing size of the DNA fragments.

The first parameter can be of various forms. Such a parameter is a number of DNA fragments at a particular size divided by the total number of fragments, which may be obtained from a histogram (any data structure providing absolute or relative counts of fragments at particular sizes). As another example, a parameter could be a number of fragments at a particular size or within a particular range divided by a number of fragments of another size or range. The division can act as a normalization to account for a different number of DNA fragments being analyzed for different samples. A normalization can be accomplished by analyzing a same number of DNA fragments for each sample, which effectively provides a same result as dividing by a total number fragments analyzed. Other examples of parameters are described in U.S. Patent Publication 2013/0237431, which is incorporated by reference in its entirety.

At block 1430, the first value is compared to a reference value. Examples of a reference value include a normal value and a cutoff value that is a specified distance from a normal value (e.g., in units of standard deviation). The reference value may be determined from a different sample from the same organism (e.g., when the organism was known to be healthy). Thus, the reference value may correspond to a value of the first parameter determined from a sample when the organism is presumed to have no inflammation. In one embodiment, the biological sample is obtained from the organism after treatment and the reference value corresponds to a value of the first parameter determined from a sample taken before treatment. The reference value may also be determined from samples of other healthy organisms.

At block 1440, a classification of a level of inflammation in the kidney is determined based on the comparison. In various embodiments, the classification may be numerical, textual, or any other indicator. The classification can provide a binary result of yes or no as to inflammation, a probability or other score, which may be absolute or a relative value, e.g., relative to a previous classification of the organism at an earlier time. In one implementation, the classification is that the kidney does not have inflammation or that the level of inflammation has decreased. In another implementation, the classification is that the kidney does have inflammation or that a level of inflammation has increased. In one embodiment, it can be determined that the first kidney is inflamed when the first value is greater than the reference value.

As described herein, the level of inflammation can include an existence of inflammation. For example, whether the first value exceeds (e.g., greater than or less than, depending on how the first parameter is define) can be used to determine if inflammation exists, or at least a likelihood (e.g., a percentage likelihood). The extent above the threshold can provide an increasing likelihood, which can lead to the use of multiple thresholds. Additionally, the extent above can correspond to a different level of inflammation. Thus, embodiments can diagnose, stage, prognosticate, or monitor progress of a level of inflammation in the kidney.

Based on the level of inflammation in the kidney, a treatment plan may be devised. The inflammation may be treated by drugs, diet, therapy, or surgery. In some cases the inflammation may be treated earlier than without methods descried herein because the existence of the inflammation may be detected earlier. The risk of complications, including death, may be reduced as a result of the detection methods.

III. DETECTING BLADDER CANCER USING SIZE OF URINARY CFDNA

The cfDNA released from cancers have been demonstrated to be of a different length compared with the cfDNA released from non-cancerous cells (31,32). We selected two cases of muscle invasive bladder cancer, reasoning that the release of a large amount of cfDNA from a lower urinary tract tumor might contribute sufficient cfDNA fragments of a different size to perturb the overall size profile of the voided urine. We collected pre- and post-operative urine samples for these two patients undergoing radical cystectomy for genome-wide bisulphite sequencing to assess the size and methylation patterns in these samples. The results show that bladder cancer cases have urinary cfDNA with larger proportion of long fragments.

A. Analysis

Figure 15A:
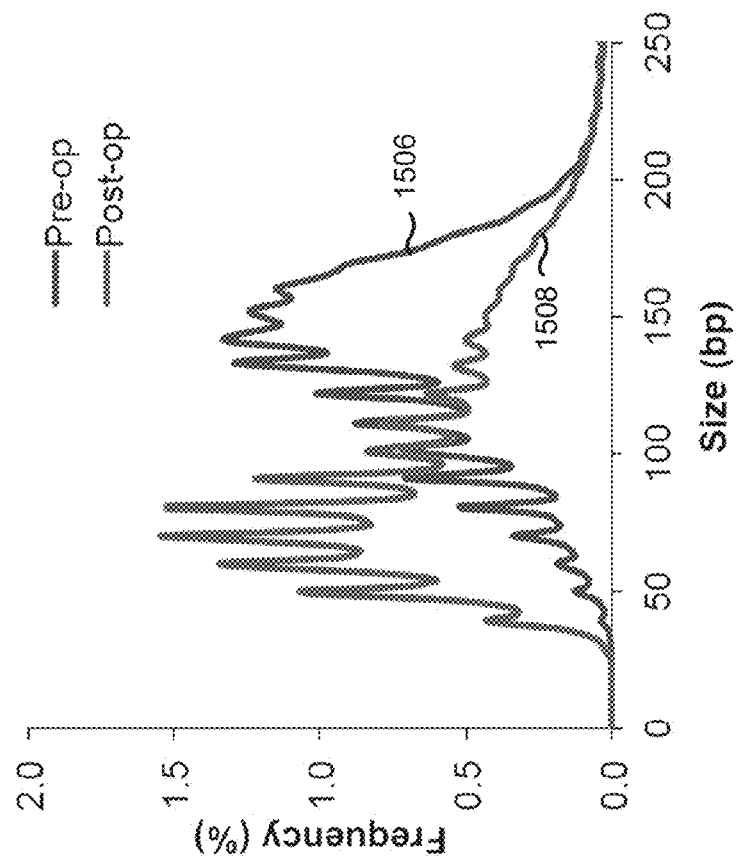
FIGS. 15A and 15B show the size profiles of pre- and post-operative urine samples from two cases of muscle invasive bladder cancer according to embodiments of the present invention.
Figure 15B:
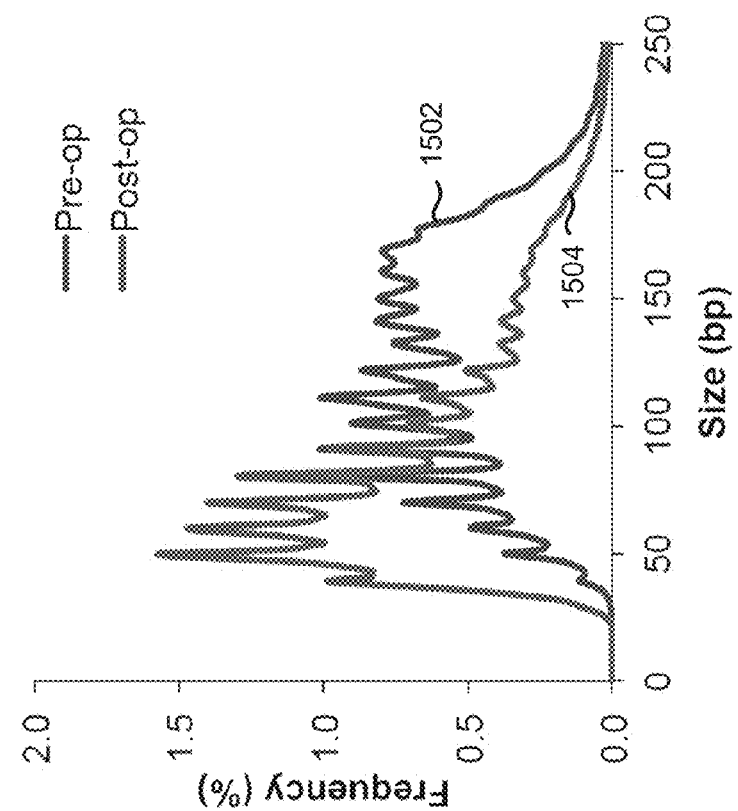

FIGS. 15A and 15B show the size profiles of pre- and post-operative urine samples from two cases of muscle invasive bladder cancer. Pre-operative samples are represented by lines 1502 and 1506. Post-operative samples are represented by lines 1504 and 1508. Both pre-operative samples show an aberrant size profile with a larger proportion of long fragments, and the size profiles are normal in the post-operative samples. This is also reflected in the summary size statistics with the preoperative sample of FIG. 15A: median 131 bp, P>70 90.1%, PI 0.10; the preoperative sample of FIG. 15B: median 143 bp, P>70 96.2%, PI 0.04; the post-operative sample in FIG. 15A: median 80 bp, P>70 60.0%, PI 1.6; and the post-operative sample in FIG. 15B: median 93 bp, P>70 72.7%, PI 1.61.

Besides P>70, a proportion of long cfDNA fragments>100 bp or other length could be used. FIGS. 15A and 15B show that a size parameter can be used to discriminate between samples having cancer (pre-op) and those not having cancer (post-op).

The normalization of size profiles in post-operative urine suggested that the large proportion of long fragments observed pre-operatively had originated from the excised tumor. This suggests that the larger fragments seen is pre-operative samples are from the bladder cancer samples. Further suggestion can be seen from the methylation deconvolution showing that 56.2% and 78.8% of the cfDNA fragments originate from the bladder tumor in the pre-operative samples. Accordingly, the proportion of long DNA fragments can be used to screen for bladder cancer or monitor for recurrence. The post-op bladder tumor contributions were 4.9% and 3.1% for FIGS. 15A and 15B respectively, which confirms the relationship between the long DNA fragments and the tumor contribution.

FIGS. 16A-16C show the size profile for three void urine samples from patients with bladder cancer. All three patients had muscle-invasive bladder cancer. There is an increased proportion of long fragments for all three samples, and this is also reflected in size summary statistics (FIG. 16A) median 131, P>70 90.1%, FI 0.10; (FIG. 16B) median 143, P>70 96.2%, FI 0.04; and (FIG. 16C) median 114, P>70 83.7%, FI 0.16. The urine size profile of patients with bladder cancer have a median of 114-143 bp, F>70 of 83-96% and a FI of less than 0.2. This reflects that urine from bladder cancer patients have a larger proportion of long cfDNA fragments and the size profile lacks the periodicity usually seen in the 50-75 bp range.

We also sequenced the pre-operative urine of a further three bladder cancer cases that were treated for non-muscle invasive disease undergoing transurethral resection of bladder tumor (TURBT). One case showed a grossly aberrant size profile with longer fragments, while the other two displayed normal size profiles.

Figure 17A:
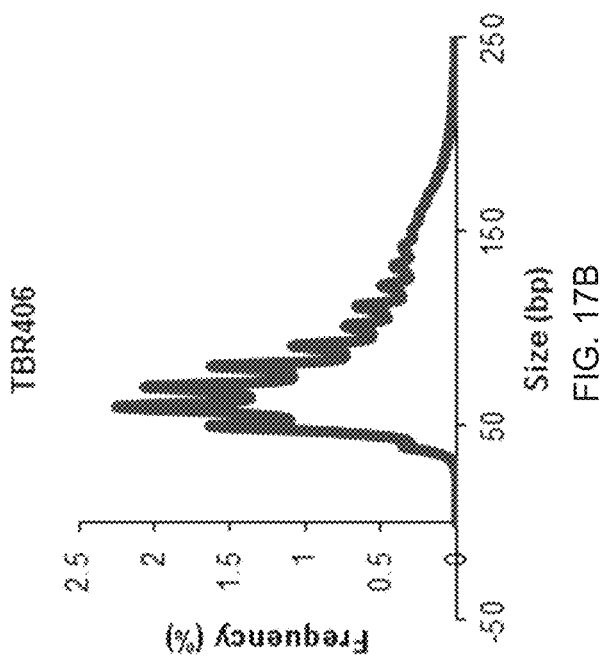
FIGS. 17A-17C show the size profiles of three pre-operative urine samples from three patients with non-muscle invasive bladder cancer undergoing TURBT according to embodiments of the present invention.
Figure 17B:
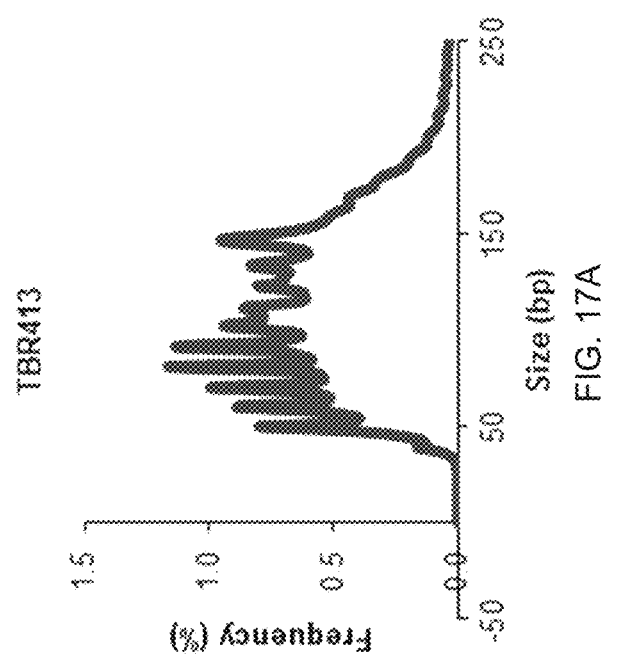
Figure 17C:
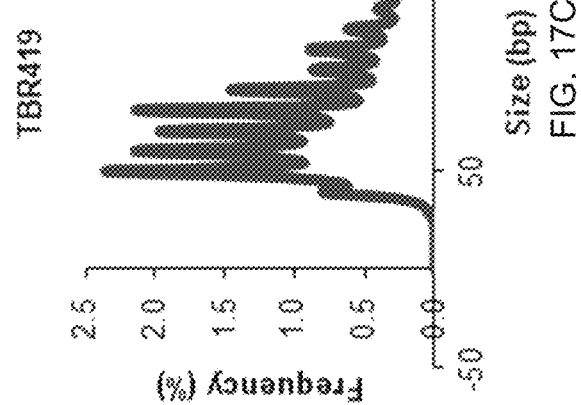

FIGS. 17A-17C show the size profiles of three pre-operative urine samples from three patients with non-muscle invasive bladder cancer undergoing TURBT. There is an increased proportion of long fragments in TBR413. The summary size statistics are: median 114 bp, P>70 83.7%, PI 0.16. The other two urinary size profiles (TBR406 and TBR 419) display size profiles that are typical of voided urine. TBR413 was thought to have non-muscle invasive pre-operatively, but was found to have muscle-invasive disease after TURBT, and subsequently required radical cystectomy. Thus, a type of cancer can be differentiated, and an aberrant size profile (e.g., statistical value for long fragments is above a threshold) may suggest more advanced disease. FIG. 17A corresponds to the same sample as FIG. 16C.

The case with aberrant size profile (TBR413) was found to have an extensive bladder tumor 14 cm in size that was high grade with muscle invasion, subsequently requiring radical cystectomy. The two other cases (TBR406 and 409) were histologically confirmed to have non-muscle invasive disease with no disease recurrence after TURBT. These results suggested that muscle invasive bladder cancers with large tumor loads might more likely release sufficient tumor DNA to give rise to aberrant urinary size profiles.

B. Method of Detecting Bladder Cancer Using Long Urinary cfDNA

Figure 18:
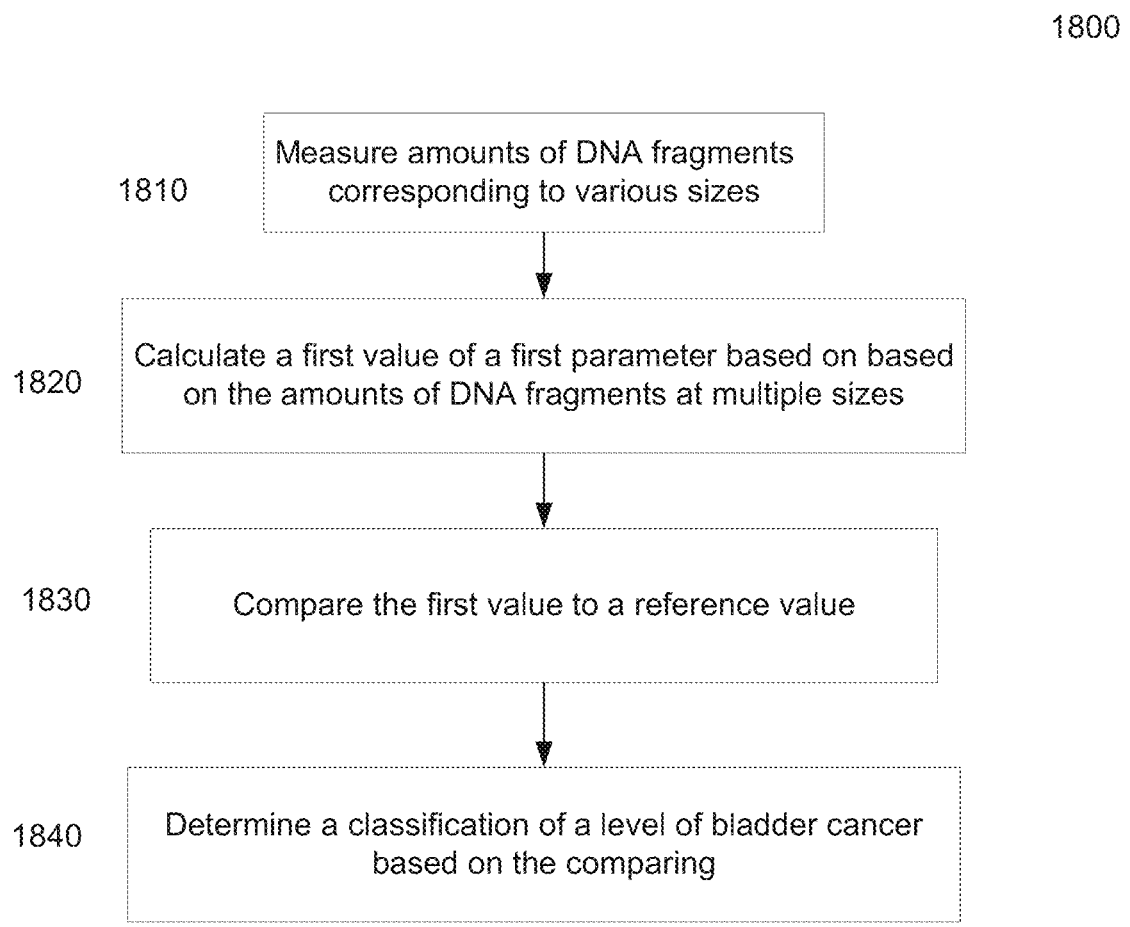
FIG. 18 shows a flowchart of a method 1800 of analyzing a urine sample of an organism to detect bladder cancer using sizes of urinary cfDNA according to embodiments of the present invention.

FIG. 18 shows a flowchart of a method 1800 of analyzing a urine sample of an organism to detect bladder cancer using sizes of urinary cfDNA according to embodiments of the present invention. The urine sample includes DNA originating from normal cells and potentially from cells associated with cancer. At least some of the DNA is cell-free in the urine sample.

At block 1810, amounts of DNA fragments corresponding to various sizes are measured. For each size of a plurality of sizes, an amount of a plurality of DNA fragments from the urine sample corresponding to the size can be measured. Block 1810 may be performed in a similar manner as block 1410 of FIG. 14.

At block 1820, a first value of a first parameter is calculated based on the amounts of DNA fragments at multiple sizes. In one aspect, the first parameter provides a statistical measure of a size profile (e.g., a histogram) of DNA fragments in the biological sample. In one embodiment, the first parameter increases with increasing size of the DNA fragments. The sizes may include fragments larger than 50, 55, 60, 65, 70, 75, 80, 85, 90, 95, 100, 105, 110, 115, or 120 bp. Block 1820 may be performed in a similar manner as block 1420 of FIG. 14.

At block 1830, the first value is compared to a reference value. Block 1830 may be performed in a similar manner as block 1430 of FIG. 14.

At block 1840, a classification of a level of bladder cancer is determined based on the comparison. For example, the organism may be determined to have bladder cancer when the first value is greater than the reference value. The determination can be of a particular level of cancer, e.g., whether the cancer is muscle invasive.

As shown in the results above, size profile analysis of urinary cfDNA can identify urine samples with an unexpectedly large proportion of long fragments, and methylation deconvolution is able to identify the origin of cfDNA fragments. In cases of urothelial cancer, we are able to identify large cfDNA fragments, and methylation deconvolution was used to ascertain that there is an increase in fragments of urothelial tumor origin for such cases of urothelial cancer.

Based on the level of cancer, a treatment plan may be devised. The cancer may be treated by chemotherapy, drugs, diet, therapy, and/or surgery. In some cases the cancer may be treated earlier than without methods descried herein because the existence of the cancer may be detected earlier. The risk of complications, including death, may be reduced as a result of the detection methods. Bladder cancer has a recurrence rate of up to 70% after surgical resection of the primary tumor. If a noninvasive urine test is done at regular intervals, the test can detect recurrence earlier and also may reduce the need or frequency of surveillance cystoscopy, which is associated with discomfort and risk of urinary tract infection.

C. Using cfDNA Fragment Size to Identify Advanced Invasive Tumors

In addition to detecting bladder cancer, the size of cfDNA fragments can be analyzed to indicate tumor stage. Invasive high grade urothelial cancers are associated with a larger proportion of long fragments.

Figure 19A:
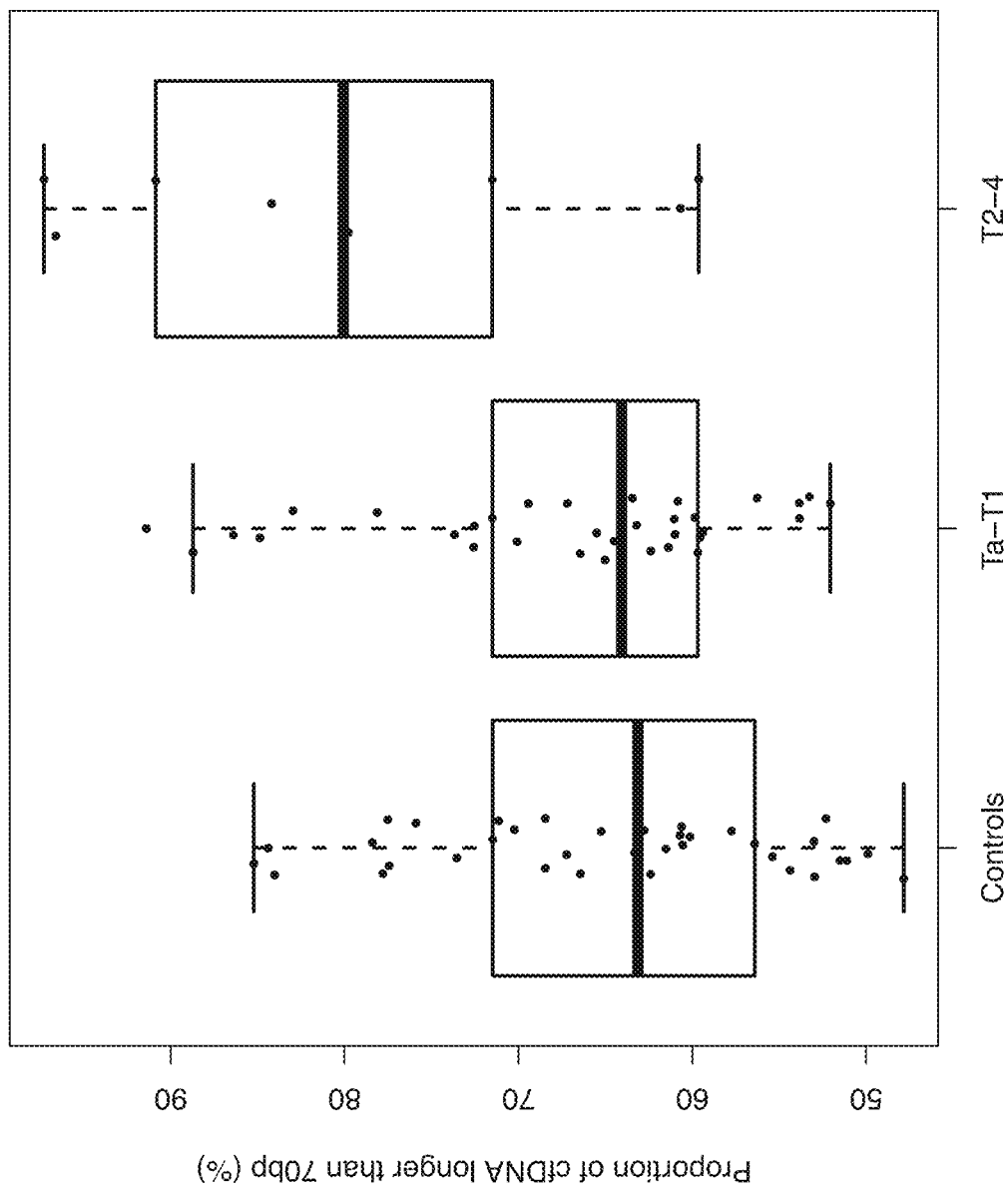

FIG. 19A is a boxplot showing the proportion of urinary cfDNA fragments longer than 70 bp (P>70 bp) in controls, and bladder cancer patients with non-muscle invasive Ta-T1 disease, and bladder cancer patients with muscle invasive T2-T4 disease. There was no significant difference between the P>70 bp in controls and bladder cancer patients with Ta-T1 disease. Bladder cancer patients with T2-T4 disease showed a larger proportion of long urinary cfDNA fragments (Mann Whitney U test P=0.03). Hence, the proportion of fragments longer than 70 bp may be used to distinguish between those with T2-T4 disease and those without the disease.

FIG. 19B is a boxplot showing the proportion of urinary cfDNA fragments longer than 105 bp (P>105 bp) in controls, and bladder cancer patients with Ta-T1 disease, and bladder cancer patients with T2-T4 disease. There was no significant difference between the P>105 bp in controls and bladder cancer patients with non-muscle invasive (Ta-T1) disease. Muscle invasive bladder (T2-T4) disease showed a larger proportion of long urinary cfDNA fragments (Mann Whitney U test P=0.005). Thus, the proportion of fragments longer than 105 bp may be used to distinguish those with T2-T4 disease and those without the disease.

IV. COMPARISON OF ABERRATIONS IN PLASMA AND URINE

Cancers may be characterized by global hypomethylation (33) and copy number aberrations (34), and these changes have been detected in the plasma of cancer patients (7). Whole genome bisulphite sequencing can determine the methylation density across the genome by 1 MB bins (or other sized regions that can have predetermined length and/or position) and determine if there are copy number changes based on the number of fragments mapped to loci across the genome. The methylation density and copy number in normal controls can be determined based on sequencing the cfDNA from cancer free samples. CNA and methylation changes can be deemed significant if there is a Z-score difference of more than 3 (or other value, e.g., chosen based on a desired sensitivity and specificity) compared with controls. Specific thresholds may be determined for urine samples that different from thresholds for other samples, e.g., plasma.

A. Aberrations in Urine Reflect the Methylation and CNA Changes in Tumor

Figure 20:
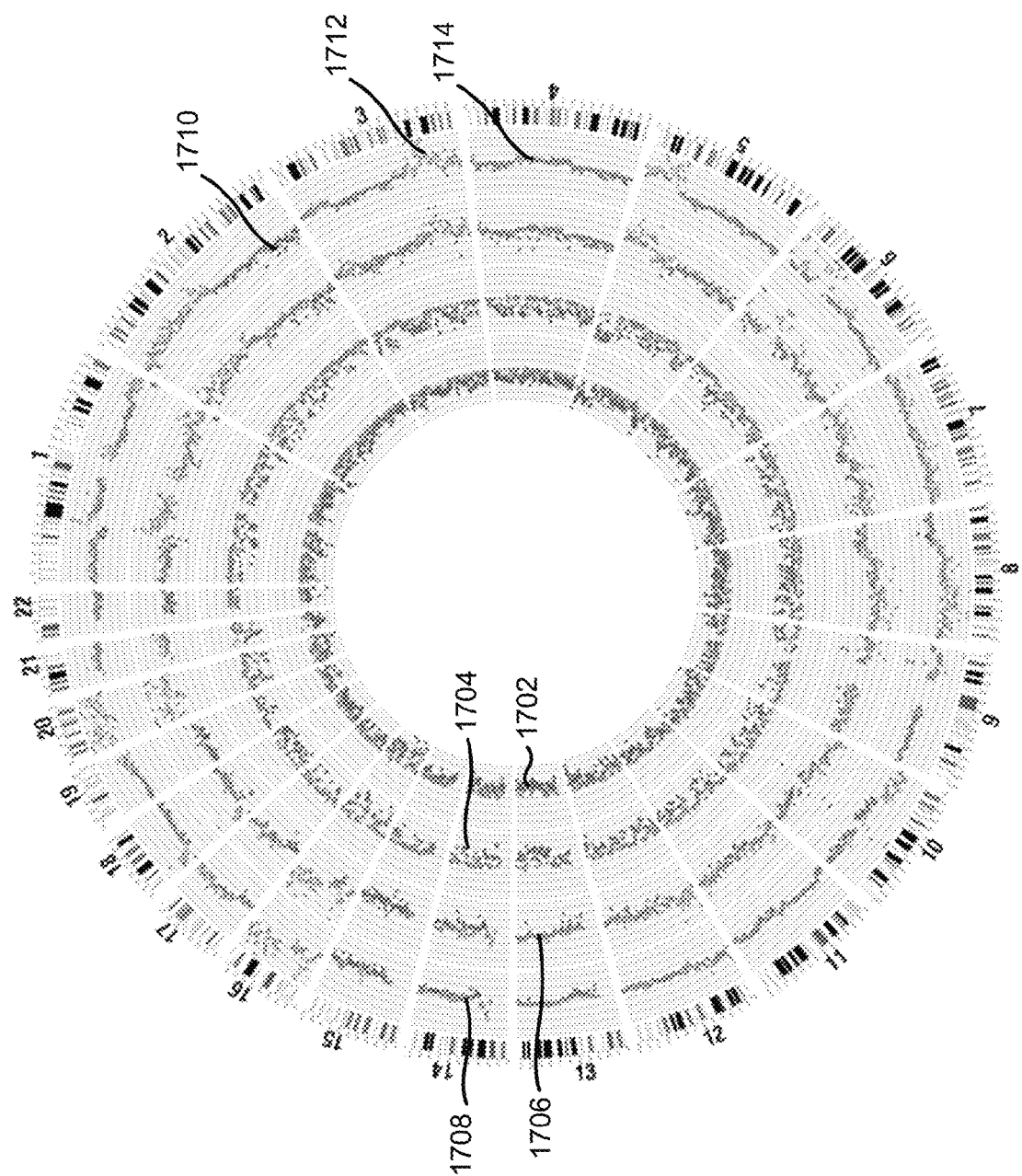
FIG. 20 shows a Circos plot displaying the concordance in global methylation and copy number aberrations between the urinary cfDNA and bladder cancer tissue according to embodiments of the present invention.

We obtained paired tumor tissue and voided urine from a bladder cancer patient with muscle invasive disease. Global hypomethylation was seen in both the urinary cfDNA and the primary bladder tumor. The bladder tumor also displayed copy number aberrations across the genome. The location of the gains and losses in urinary cfDNA mirrored those seen in the tumor (FIG. 20). These results suggested that hypomethylation and copy number aberrations observable in the urinary cfDNA was representative of the aberrations seen in the primary bladder cancer.

FIG. 20 shows a Circos plot displaying the concordance in global methylation and copy number aberrations between the urinary cfDNA and bladder cancer tissue according to embodiments of the present invention. Chromosomal position is represented in ascending order in a clockwise direction. The four rings, from the center to the periphery represent: 1) bladder tumor methylation (ring 2002), 2) urinary cfDNA methylation (ring 2004), 3) bladder tumor copy number (ring 2006), and 4) urinary cfDNA copy number (ring 2008). Global methylation density in 1 Mb bins is represented in ring 2002 and ring 2004, with significant hypomethylation and hypermethylation represented by red and green dots, respectively. Hypermethylation is absent in these samples. Copy number changes are represented in the two outer rings. Copy number losses are represented by red dots (e.g., dot 2010) and lie toward the center of the ring. Copy number gains are represented by green dots (e.g., dot 2012) and lie away from the center of the ring. Grey dots (e.g., dot 2014) represent no significant deviation from controls.

FIGS. 21A-21E show Circos plots of global methylation and copy number aberrations the urinary cfDNA from five bladder cancer patients (A-E) according to embodiments of the present invention. The inner ring (e.g., ring 2102) represents methylation density, and the outer ring (e.g., ring 2104) represents copy number changes. Hypomethylation and copy number losses are colored red (e.g., dot 2106) and lie toward the center of the ring, while hypermethylation and copy number gains are colored green (e.g., dot 2108) and lie away from the center of the ring. Grey dots (e.g., dot 2110) represent no significant deviation from controls. The data in FIG. 21A corresponds to the data in the urinary cfDNA rings in FIG. 20.

Figure 21B:
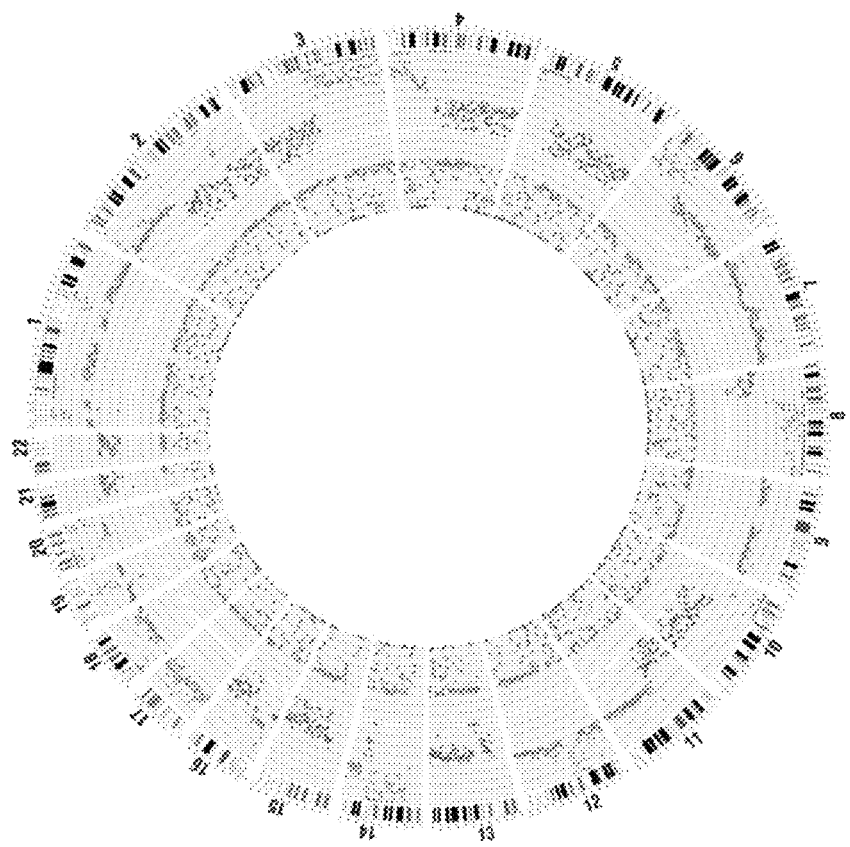
FIGS. 21A-21E show Circos plots of global methylation and copy number aberrations the urinary cfDNA from five bladder cancer patients (A-E) according to embodiments of the present invention.
Figure 21A:
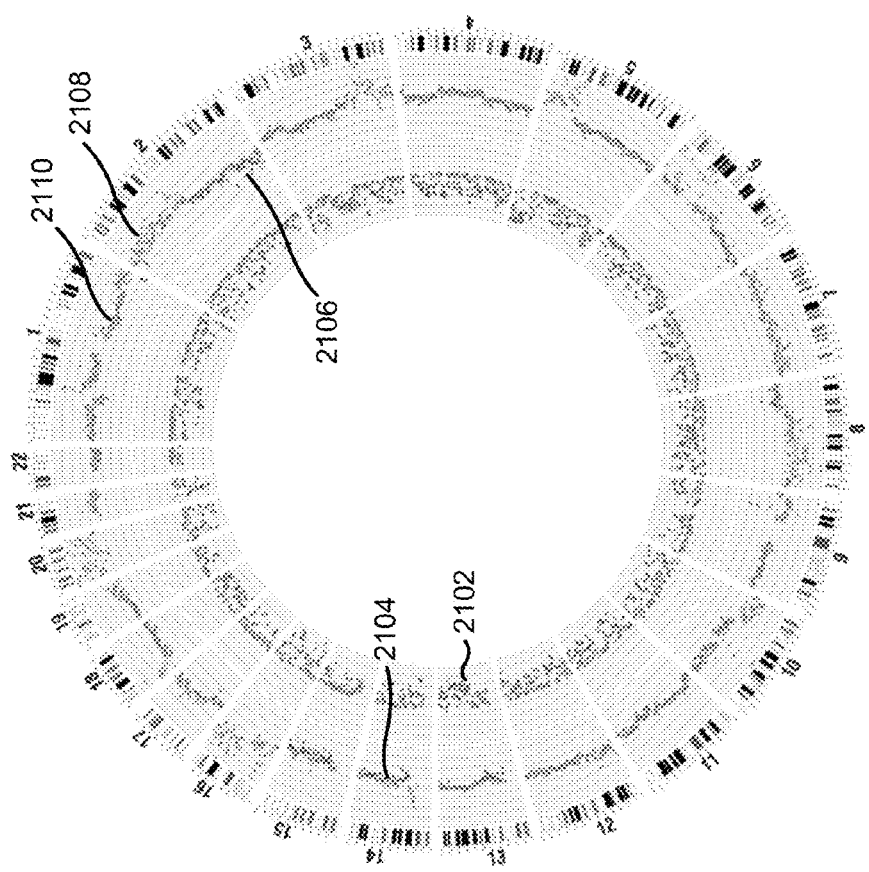
Figure 21D:
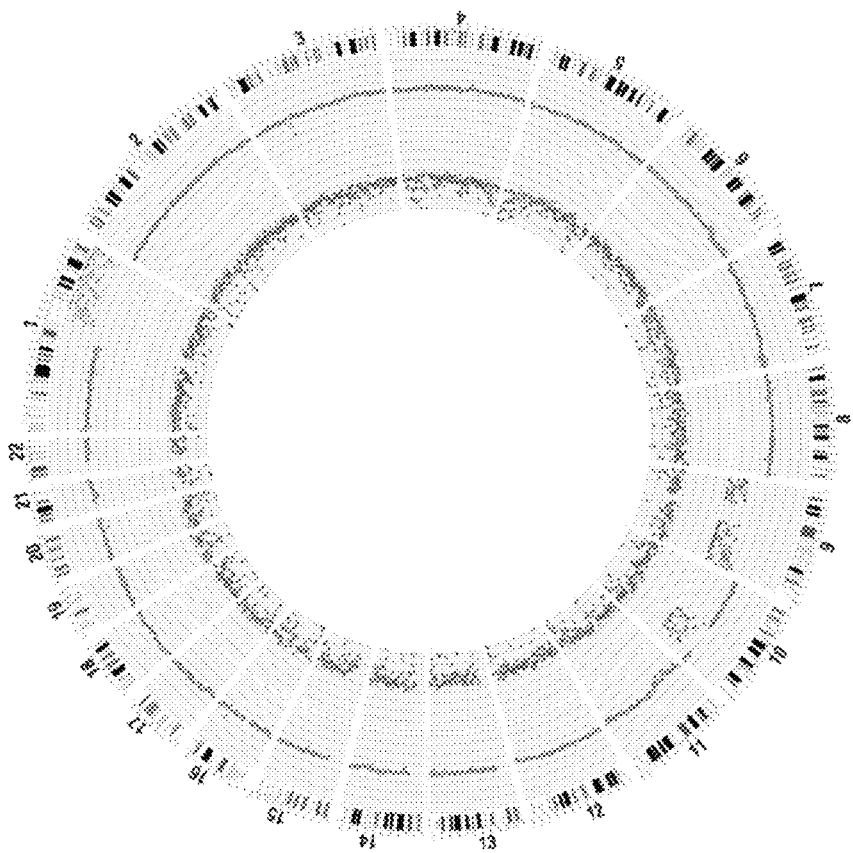
Figure 21C:
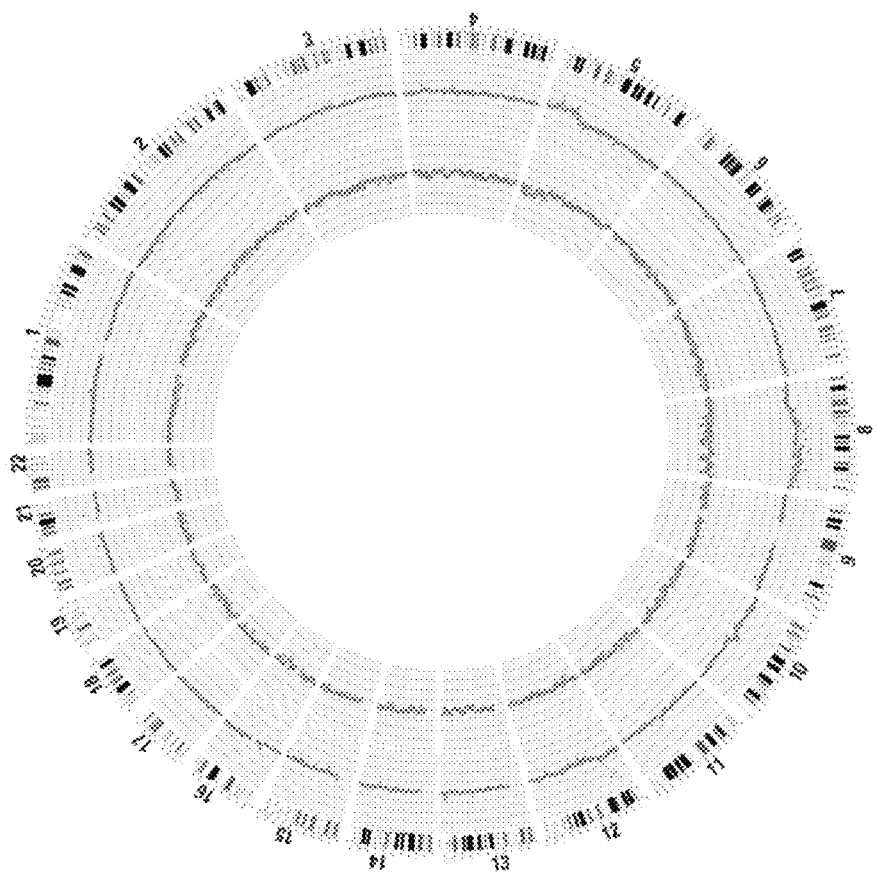
Figure 21E:
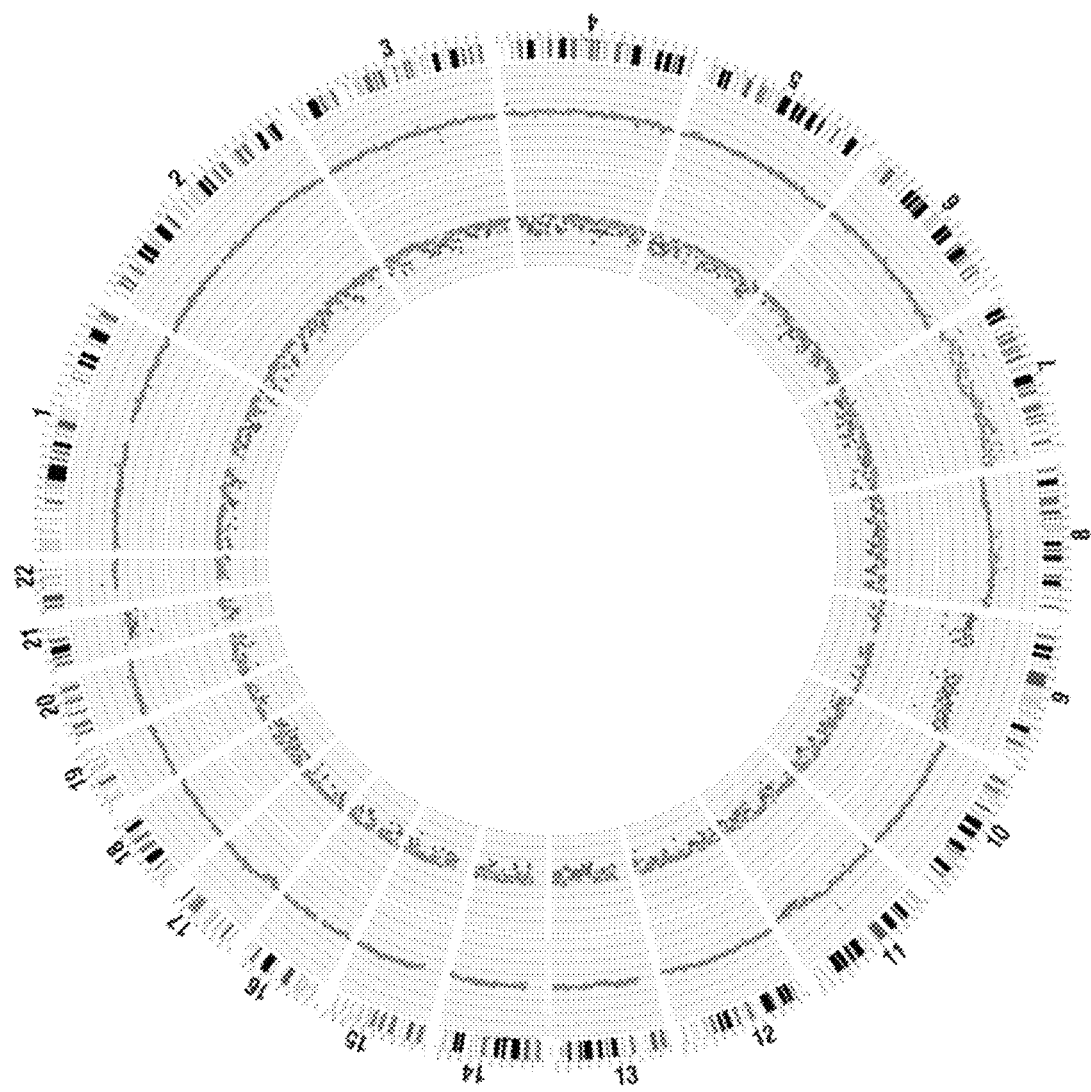

We found evidence of global hypomethylation in the urinary cfDNA in four samples (FIGS. 21A, 21B, 21D, and 21E) and copy number aberrations in all five samples. Of note, the two cases who were pre-operatively confirmed to have muscle invasive disease showed large copy number changes in more than half of the chromosomes (FIGS. 21A and 21B). FIG. 21B also shows hypermethylation in addition to hypomethylation. The case subsequently confirmed to have extensive muscle invasive disease after TURBT (FIG. 21D) also showed clear global hypomethylation and large copy number gains and losses in chromosomes 1q, 9, and 10q. FIG. 21A shows results from the patient T22 that corresponds to the pre-operative size profile in FIG. 15A. FIG. 21B shows results from the patient T23 that corresponds to the pre-operative size profile in FIG. 15B. FIG. 21C shows results from the patient with TBR406 in FIG. 17B. FIG. 21D shows results from the patient with TBR413 in FIG. 17A. FIG. 21E shows results from the patient with TBR419 in FIG. 17C. FIG. 21C, FIG. 21D, and FIG. 21E, the three cases with non-muscle invasive disease, showed mild hypomethylation and relatively subtle evidence of copy number aberrations in terms of number and amplitude.

Genomewide bisulfite sequencing allows the simultaneous analysis of aberrant cfDNA size profile, copy number, and global methylation changes associated with bladder cancer. Despite the in vivo degradation and cfDNA loss during bisulfite conversion, the global hypomethylation and copy number aberrations detected in the urinary cfDNA correspond closely with the changes seen in the primary tumor tissue. This approach thus provides a noninvasive way for assessing methylation status and copy number variation that is representative of the bladder tumor.

Copy number aberrations are commonly observed in bladder cancers (38). These changes were observable in all five urine samples from bladder cancer patients. Copy number aberrations may also detect a very low grade disease.

Furthermore, cases with muscle invasive disease and a high tumor burden were more likely to display prominent perturbations of size profile, copy number, and global hypomethylation. The enablement of a combination of these analyses from a single bisulfate sequencing run may facilitate the detection of bladder cancer cases and also be able to differentiate cases with more advanced disease. The ability of methylation deconvolution to detect corresponding changes in bladder tumor and small intestines contribution also suggests that this method can be extended for the detection of an increased contribution from cells that release cfDNA with a distinct methylomic pattern for the detection of other urologic, renal, or systemic conditions.

We sequenced the cfDNA from the urine, and also DNA extracted from the bladder tumor (grade 3 urothelial carcinoma, T3) and found that the CNA and global 1 MB hypomethylation observed in the urine are highly comparable with the changes in the bladder tumor.

Figure 22B:
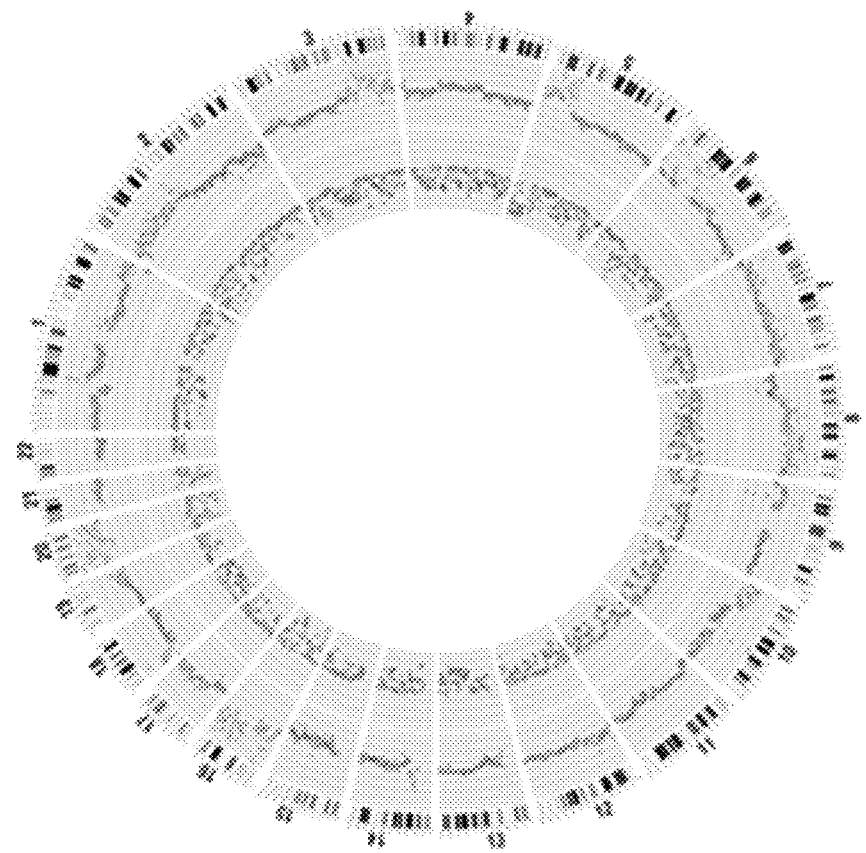
FIGS. 22A and 22B show Circos plots for the bladder cancer tumor (19A) and cf urine (19B) for T22 according to embodiments of the present invention.
Figure 22A:
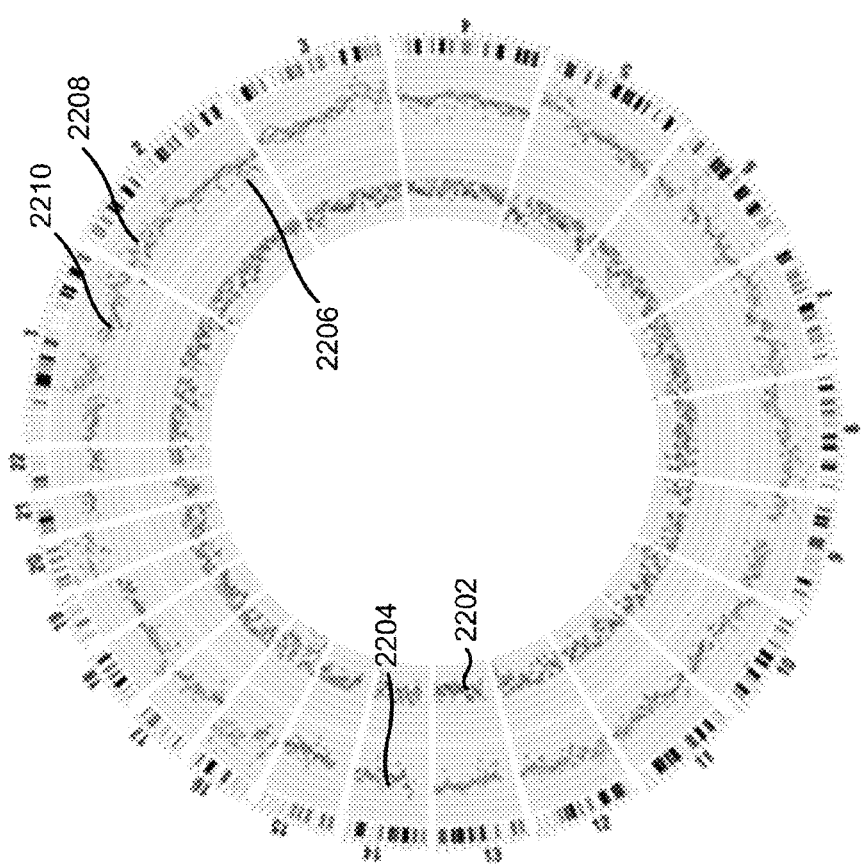

FIGS. 22A and 22B show Circos plots for the bladder cancer tumor (FIG. 22A) and cf urine (FIG. 22B) for T22. The inner ring (e.g., ring 2202) represents methylation density, and the outer ring (e.g., ring 2204) represents copy number changes. Hypomethylation and copy number losses are colored red (e.g., dot 2206) and lie toward the center of the ring, while hypermethylation and copy number gains are colored green (e.g., dot 2208) and lie away from the center of the ring. Grey dots (e.g., dot 2210) represent no significant deviation from controls. Comparing the circos plot of the bladder cancer tumor and the cf urine, there is global hypomethylation in both. There are also numerous CNA in the bladder tumor and urine, and the location of these aberrations are almost identical in both. As a result of the similarities, cf urine aberrations may be used to detect a bladder tumor. FIG. 22B corresponds to the same sample used for FIG. 20.

B. Hypermethylation Elevated with Bladder Cancer

Detecting cancer by analyzing cfDNA for hypermethylation is not conventional, but we found that hypermethylation could also be used to determine a classification of a level of cancer. We identified 1,082,774 CpG sites that are consistently unmethylated (e.g., <2%) in normal tissues (blood cells, kidney, urothelium) contributing to urinary cfDNA. Unmethylated may refer to sites that are methylated at less than 2%, 5%, or 10%. These sites are more commonly methylated in tumors and therefore are hypermethylated compared to normal tissues. As examples, hypermethylated sites can be methylated at more than 30%, 40%, 50%, 60%, 70%, 80%, or 90%. We calculated the overall methylation density in these CpG sites in the urine samples from bladder cancer cases and controls.

Figure 23A:
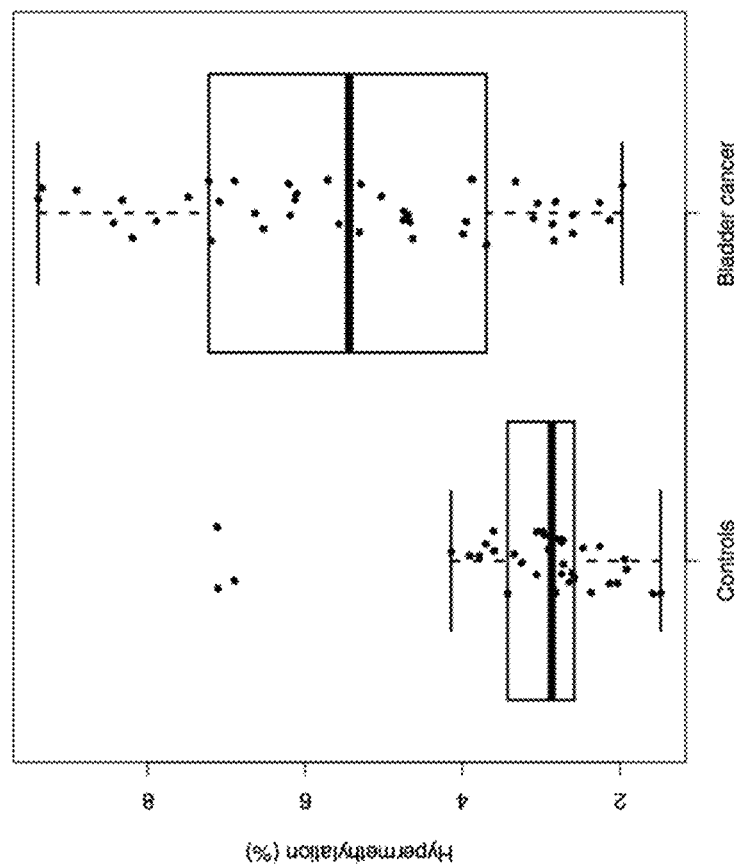
FIG. 23A shows a boxplot of the overall hypermethylation density in bladder cancer cases and in controls according to embodiments of the present invention.
Figure 23B:
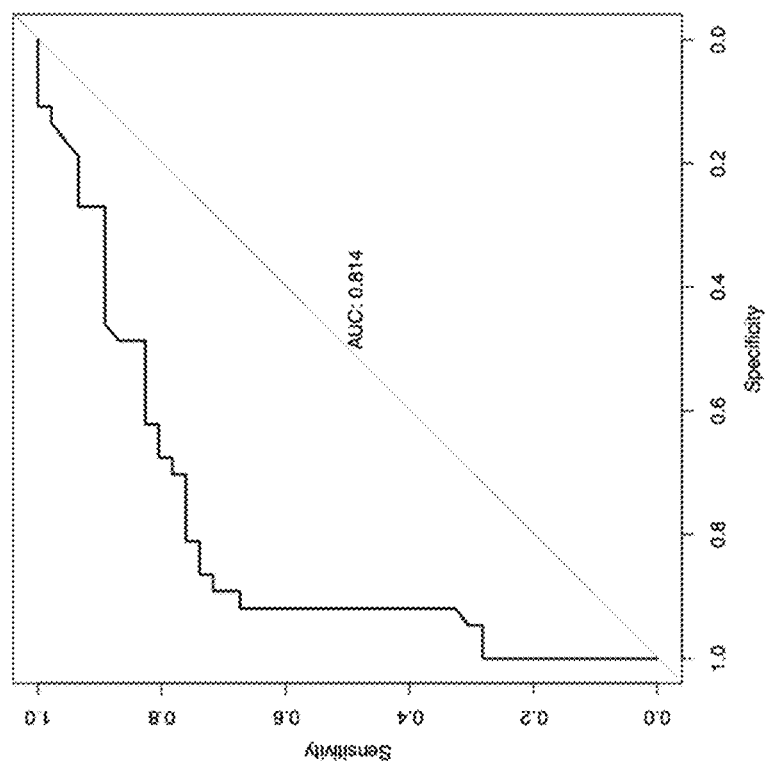
FIG. 23B shows a receiver operating characteristic (ROC) curve for using hypermethylation density to detect cancer according to embodiments of the present invention.
Figure 24B:
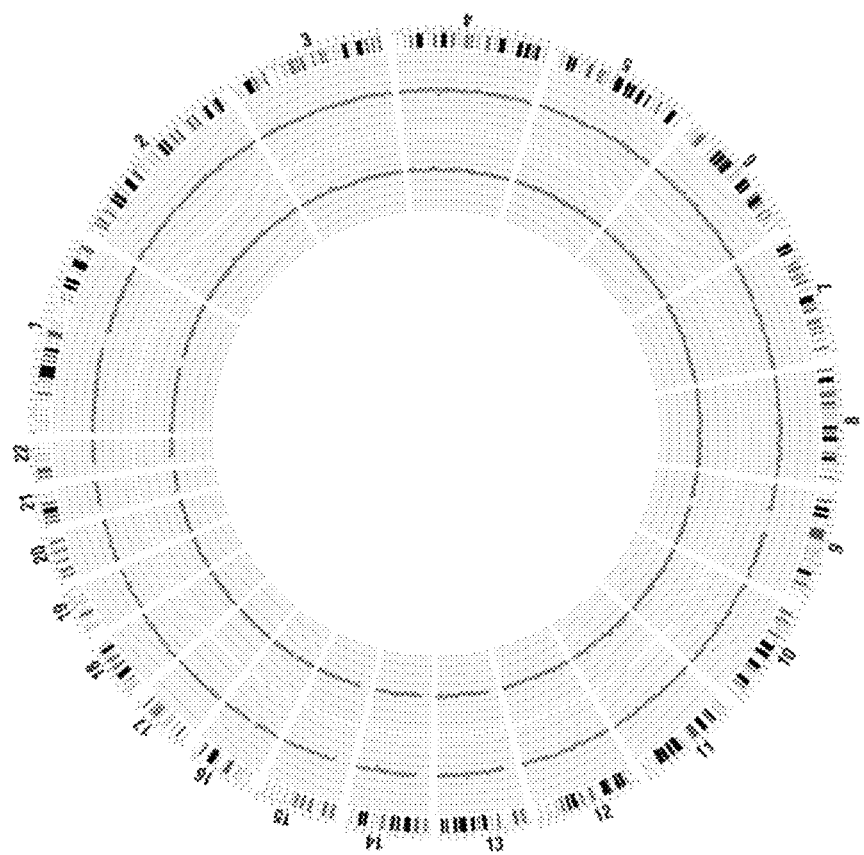
FIGS. 24A-24D show the pre-op (FIG. 24A and FIG. 24C) and post-op (FIG. 24B and FIG. 24D) cf urine of two bladder cancer patients undergoing radical cystectomy (T22 and T23) according to embodiments of the present invention.
Figure 24A:
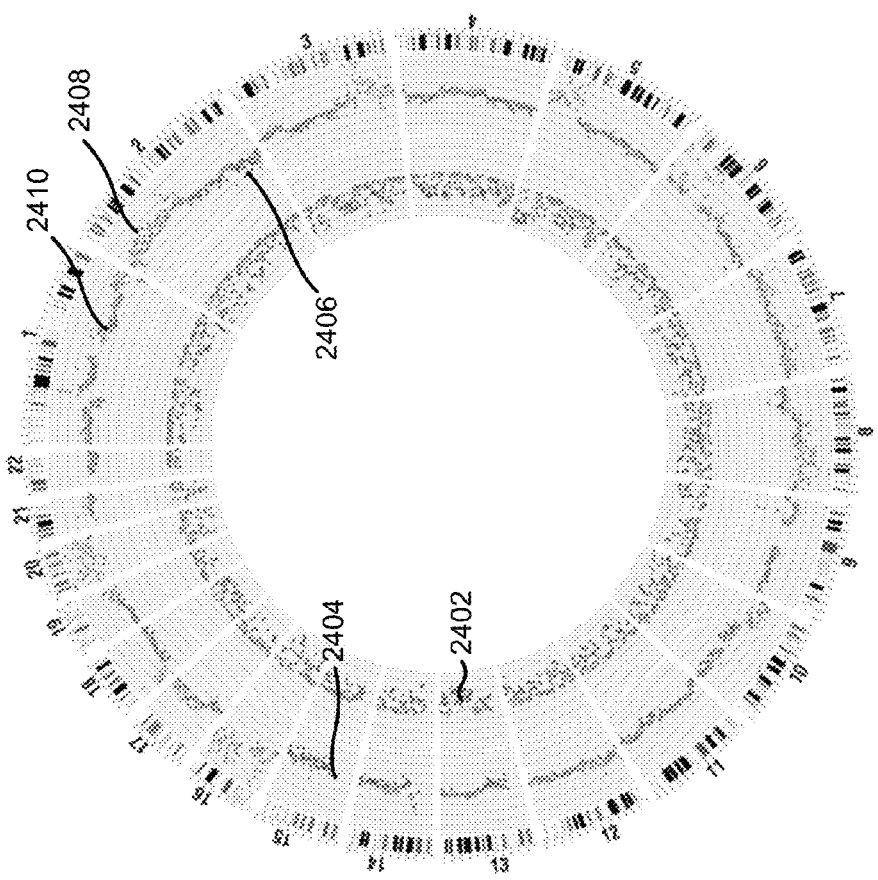
Figure 24D:
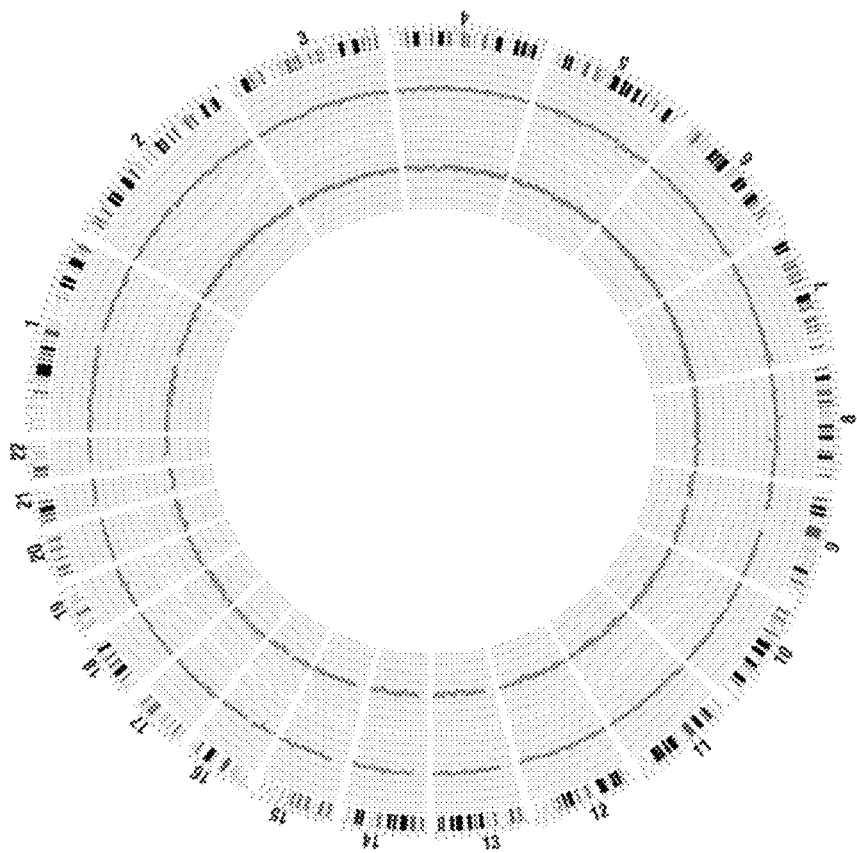
Figure 24C:
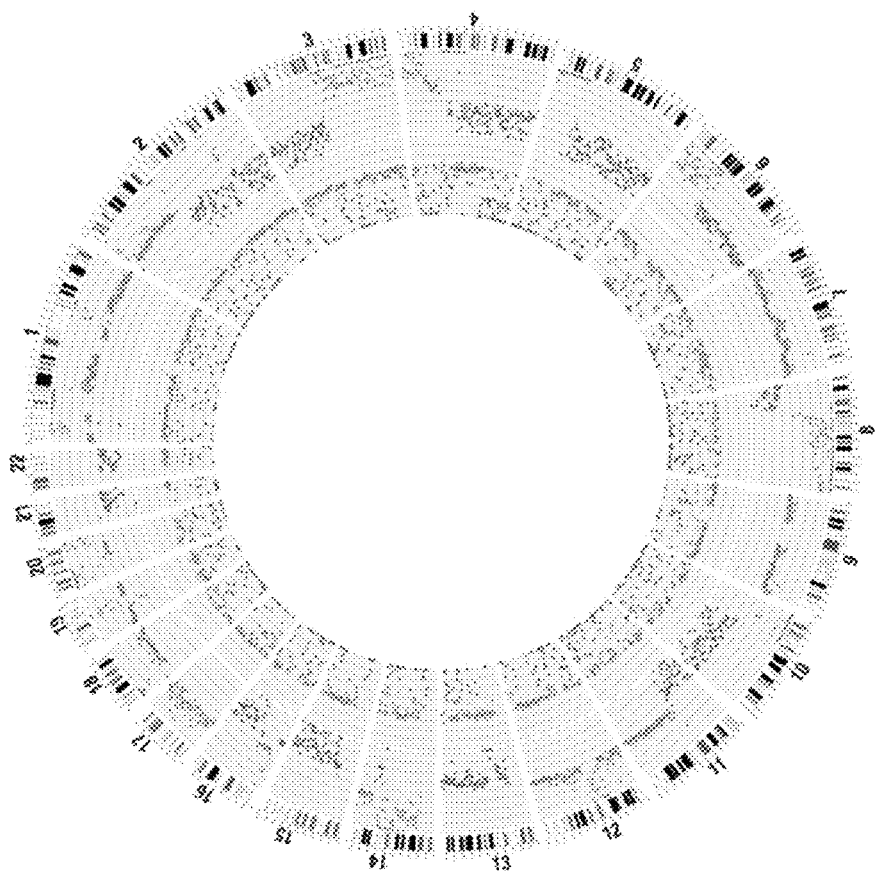

FIG. 23A shows a boxplot of the overall hypermethylation density in bladder cancer cases and in controls at these 1,082,774 CpG sites. Bladder cancer cases showed a higher overall methylation density compared with controls. FIG. 23B shows an ROC curve for using hypermethylation density to detect cancer. The AUC was 0.814.

C. CNA and Hypomethylation in Pre-Op Urine are Absent in Post-Op Urine

FIGS. 24A-24D shows the pre-op (FIGS. 24A and 24C) and post-op (FIGS. 24B and 24D) cf urine of two bladder cancer patients undergoing radical cystectomy (T22 and T23). The inner ring (e.g., ring 2402) represents methylation density, and the outer ring (e.g., ring 2404) represents copy number changes. Hypomethylation and copy number losses are colored red (e.g., dot 2406) and lie toward the center of the ring, while hypermethylation and copy number gains are colored green (e.g., dot 2408) and lie away from the center of the ring. Grey dots (e.g., dot 2410) represent no significant deviation from controls. CNA and hypomethylation associated with bladder cancer are clearly observable in pre-op urine (FIGS. 24A and 24C) while cf urine in post-op samples (FIGS. 24B and 24D) normalizes with copy number and methylation levels comparable with cancer-free controls.

Figure 25A:
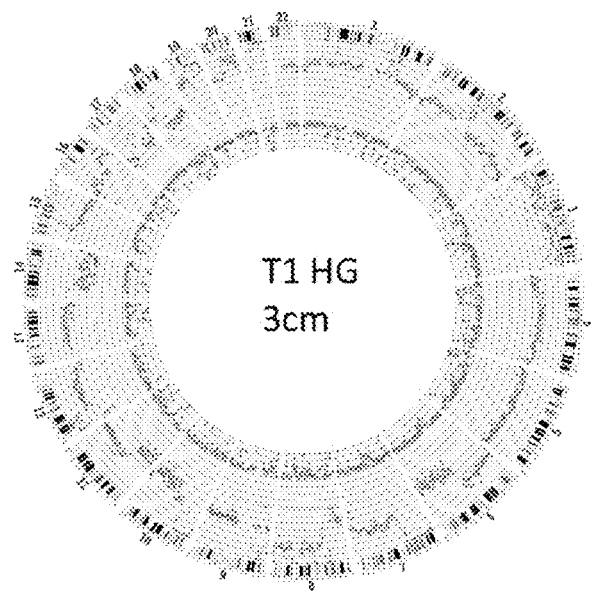
FIGS. 25A-25D show pre- and post-operative Circos plots of global methylation and CNA for two patients according to embodiments of the present invention.
Figure 25B:
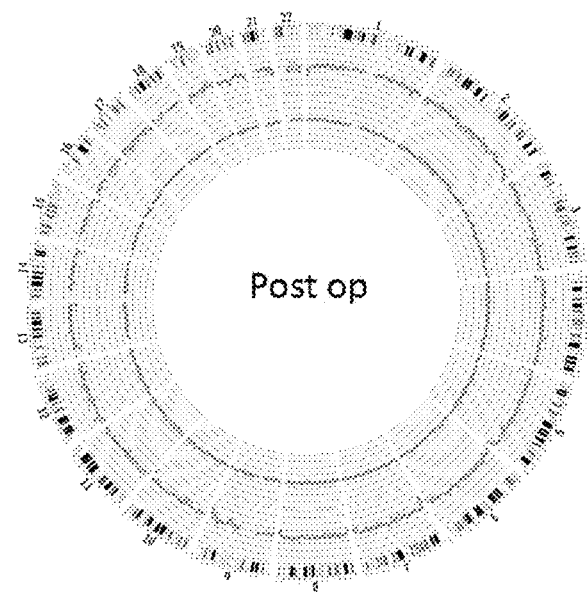

FIGS. 25A-25D show pre- and post-operative Circos plots of global methylation and CNA for two patients. FIG. 25A and FIG. 25B are the pre- and post-operative circos plots for a patient with 3 cm T1HG disease. The post-operative Circos plots show clearance of the global hypomethylation and CNAs seen in the pre-operative sample. Pathology confirmed clear margins for the urothelial tumor, and the patient has not developed recurrence the post-operative sample was obtained.

Figure 25C:
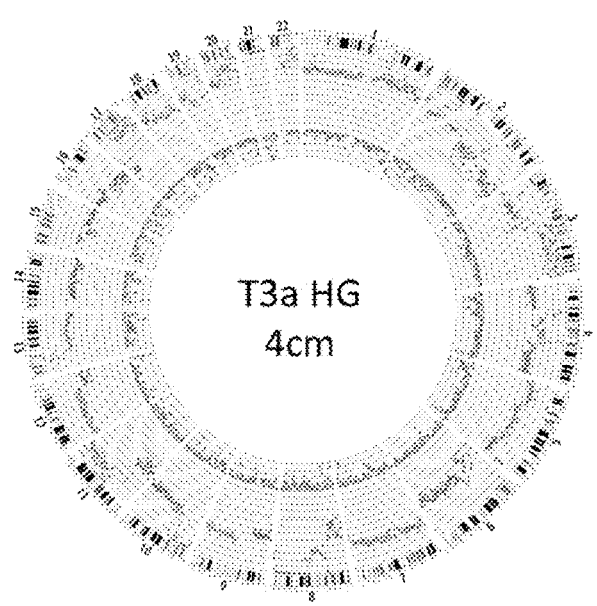
Figure 25D:
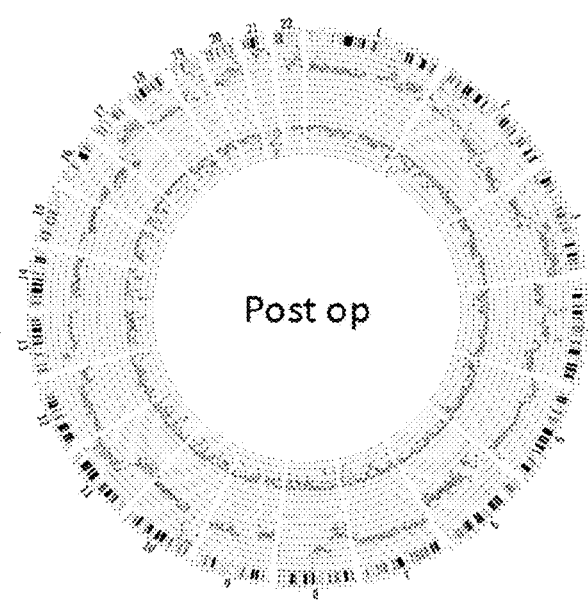

FIG. 25C and FIG. 25D are the pre- and post-operative circos plots for a patient with T3a HG disease. The post-operative circos plots shows the persistence of global hypomethylation and CNA. Pathology reports confirmed the presence of muscle invasive disease with tumor present at the resection margin and the presence of residual disease. Thus, genomewide bisulfite sequencing can be employed to look for the presence of residual disease and can be used for the longitudinal monitoring for tumor derived cfDNA in patients undergoing treatment for bladder cancer.

Analysis of methylation level and copy number aberrations may help evaluate the success of a cancer treatment (including an operation). In addition, analysis may monitor the remission, progression, or severity of cancer.

Figure 26:
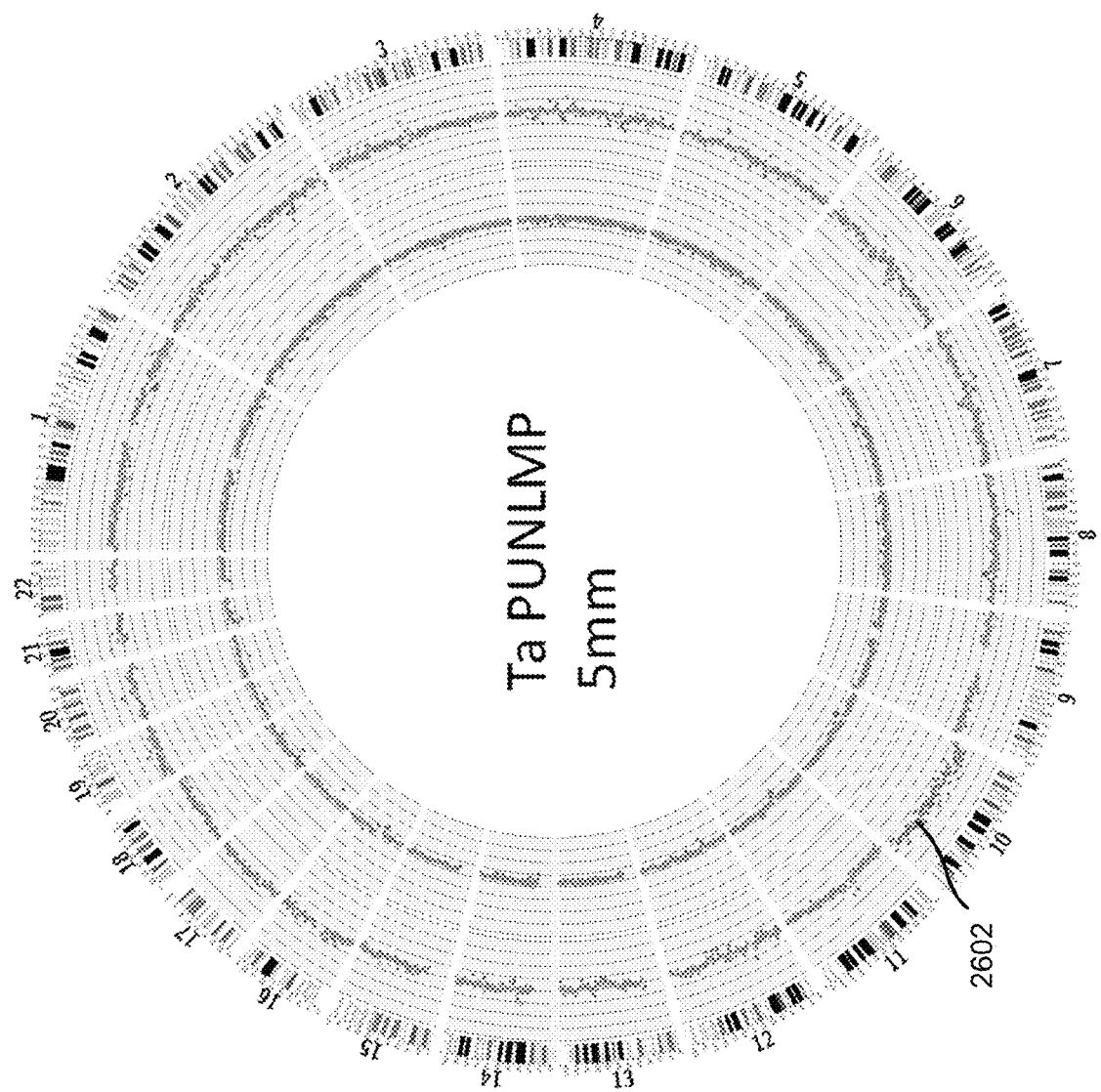
FIG. 26 is a Circos plot showing the methylation and copy number aberration in a bladder cancer patient with noninvasive (Ta) papillary urothelial neoplasm with low malignant potential (PUNLMP) according to embodiments of the present invention.

D. CNA and Hypomethylation can be Detected in the Cell-Free Urine and Urine Pellet FIG. 26 is a Circos plot showing the methylation and copy number aberration in a bladder cancer patient with noninvasive (Ta) papillary urothelial neoplasm with low malignant potential (PUNLMP). The inner ring represents methylation density, and the outer ring represents copy number changes. Hypomethylation and copy number losses are colored red and lie toward the center of the ring, while hypermethylation and copy number gains are colored green and lie away from the center of the ring. Grey dots represent no significant deviation from controls. The data in the figure were obtained from sequencing the urine of the patient. A copy number gain (section 2602) in chromosome 10 can be seen in this patient with very low grade disease with low grade histology. Hence, low grade diseases or early cancers may be identified using the copy number aberration.

Urine samples can be separated into the cellular and cell-free portion by centrifugation, with the cell free portion further undergoing filtering. Most urine samples have a small but visible urine pellet, from which DNA can be extracted. The urine pellet may be the content at the bottom of the tube after centrifugation at 3000×g and may include cellular material. We extracted DNA from a bladder cancer urine sample to perform whole genome bisulphite sequencing.

Figure 27B:
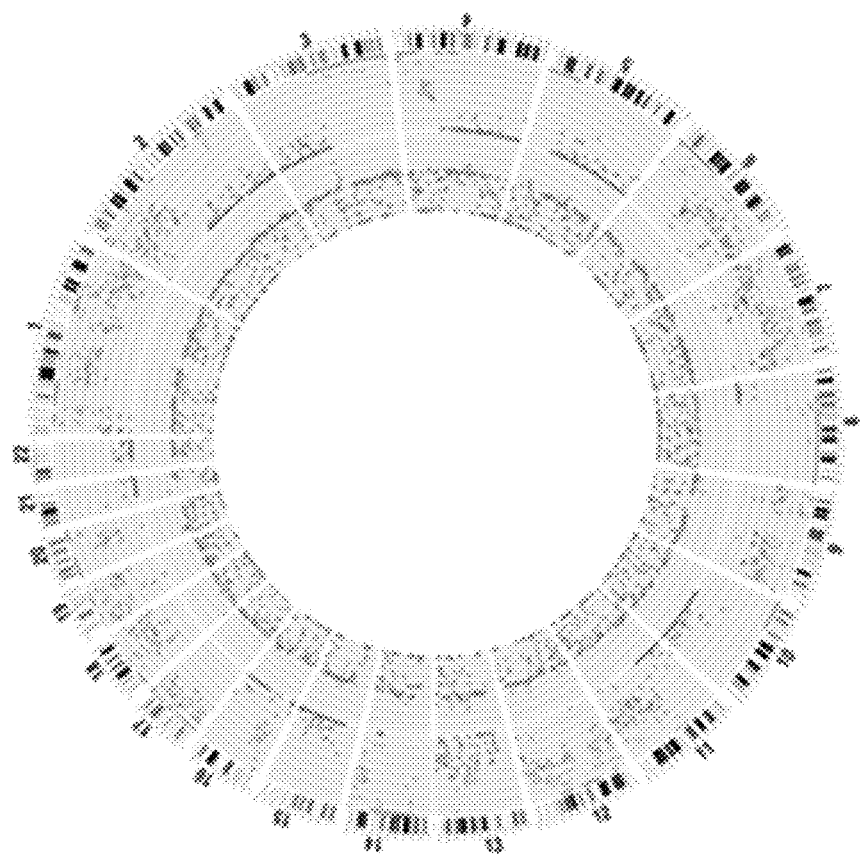
FIGS. 27A and 27B show the Circos plot for the cf urine (FIG. 27A) and the urine pellet (FIG. 27B) from a bladder cancer patient (T23) obtained from the same urine void according to embodiments of the present invention.
Figure 27A:
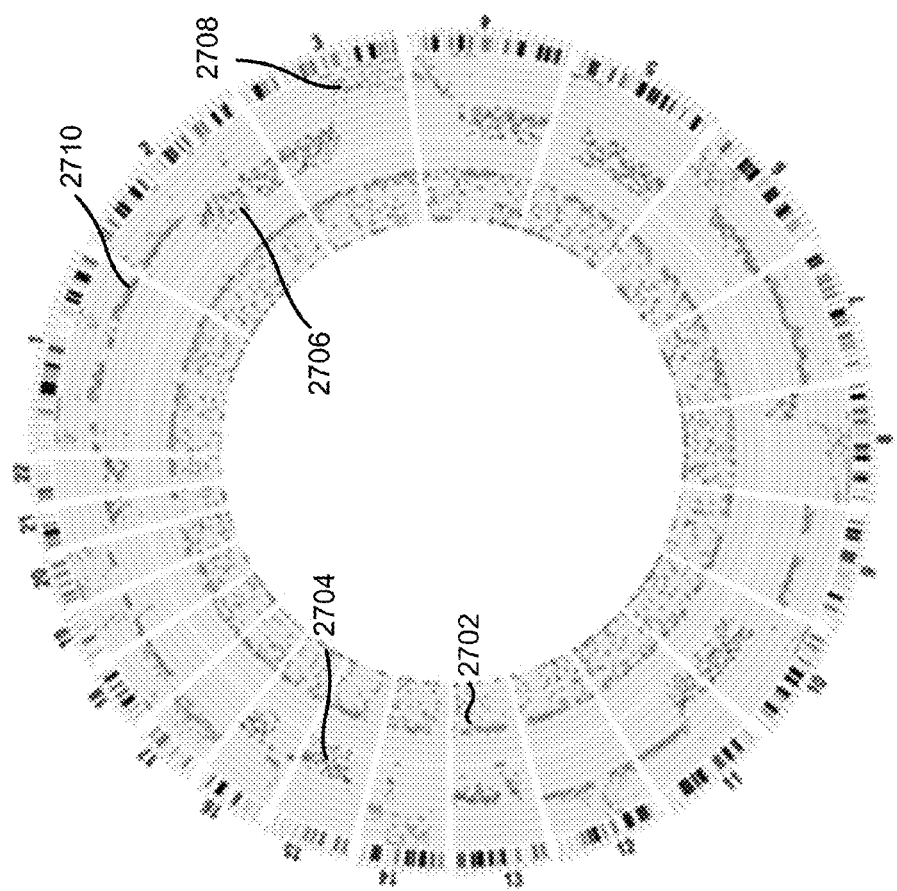
Figure 28B:
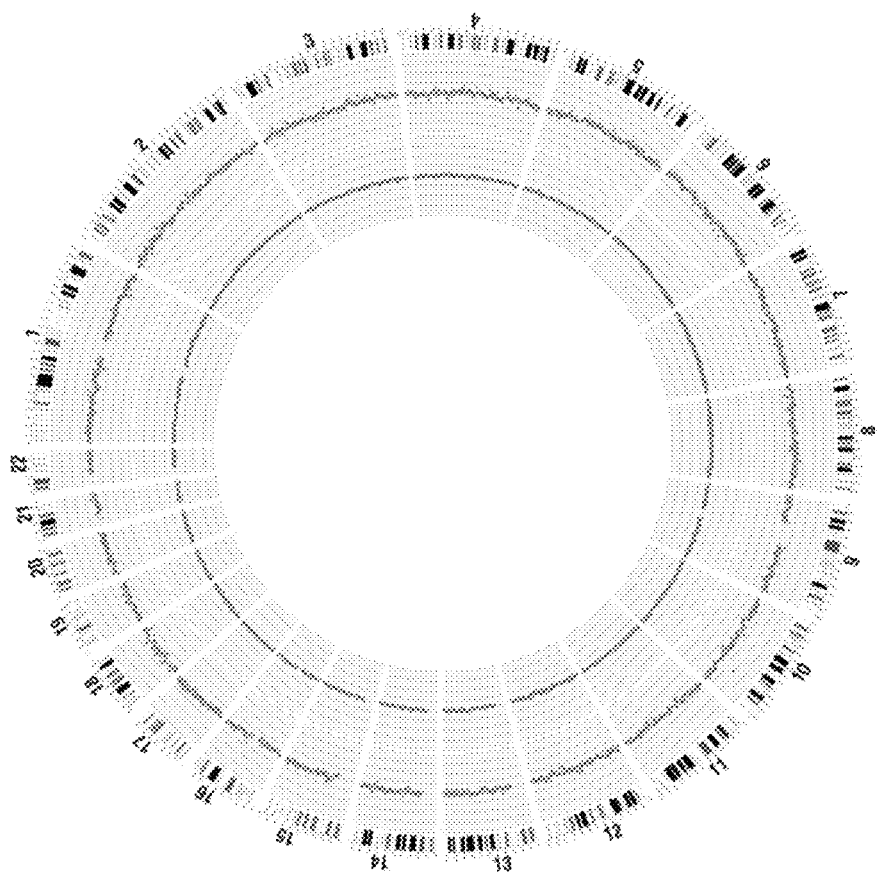
FIGS. 28A-28D show Circos plot for the cf urine (FIG. 28A and FIG. 28C) and the plasma (FIG. 28B and FIG. 28D) from two bladder cancer patients (T22 and T23) according to embodiments of the present invention.
Figure 28A:
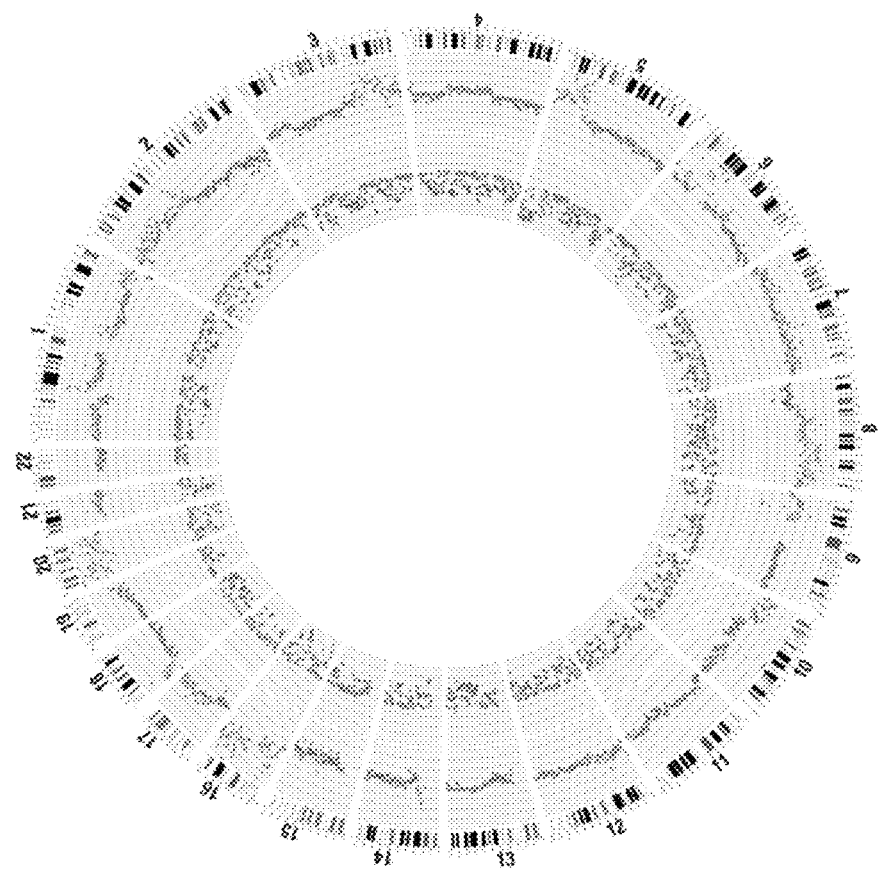
Figure 28D:
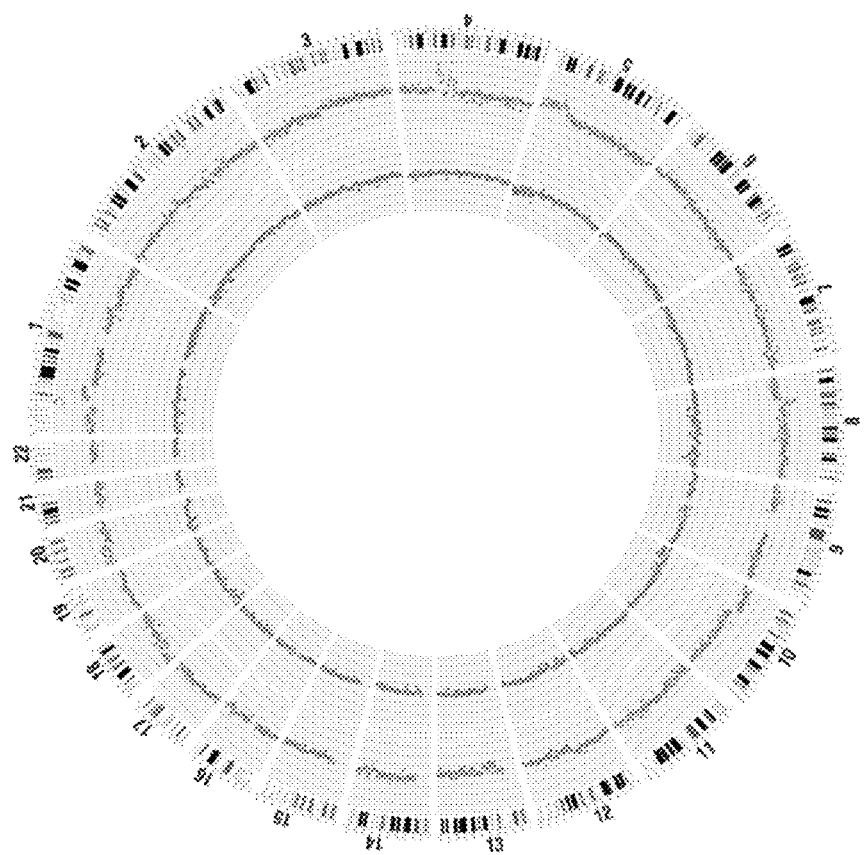
Figure 28C:
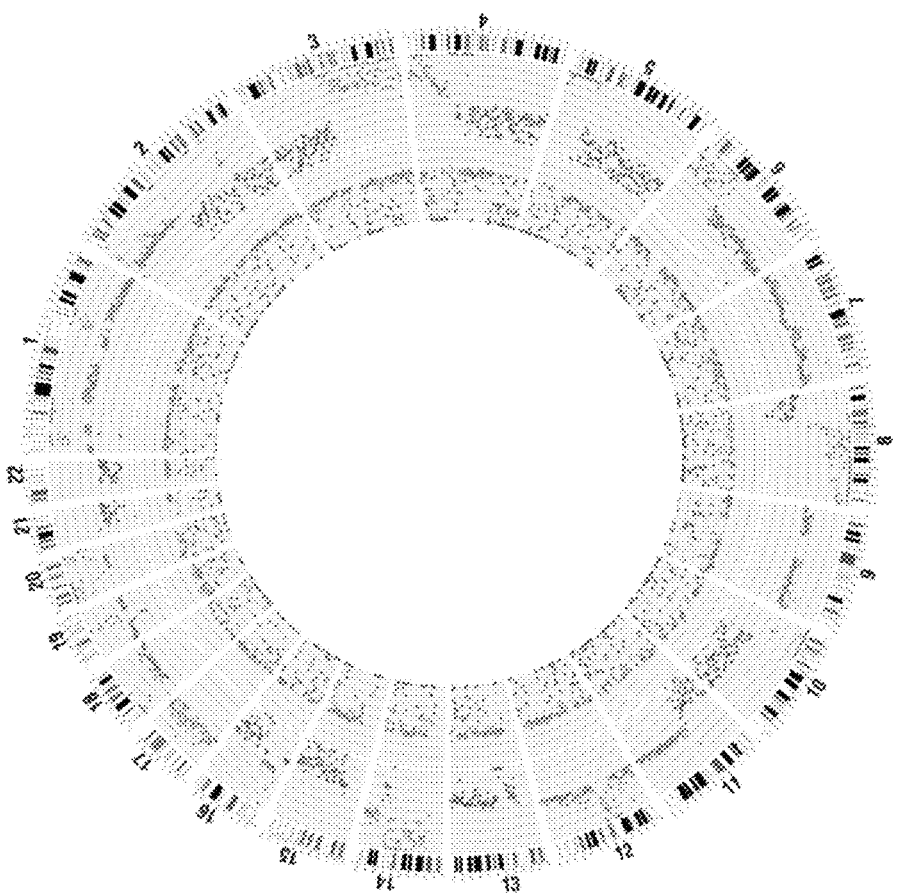

FIGS. 27A and 27B show the Circos plot for the cf urine (FIG. 27A) and the urine pellet (FIG. 27B) from a bladder cancer patient (T23) obtained from the same urine void. The inner ring (e.g., ring 2702) represents methylation density, and the outer ring (e.g., ring 2704) represents copy number changes. Hypomethylation and copy number losses are colored red (e.g., dot 2706) and lie toward the center of the ring, while hypermethylation and copy number gains are colored green (e.g., dot 2708) and lie away from the center of the ring. Grey dots (e.g., dot 2710) represent no significant deviation from controls. When present and with substantial DNA extracted, the urine pellet can be sequenced to show global hypomethylation and CNA that reflects bladder cancer. The hypomethylation and location of CNA in the urine pellet is comparable with the changes seen in the cf urine.

Urine pellet size varies between different samples. Some urine samples have no visible urine pellet after centrifugation (i.e., low cellular content). In FIGS. 27A and 27B, the amplitude of CNA and hypomethylation in urine pellet were higher compared to cell free DNA, which suggests that the pellet based CNA may be more sensitive in certain instances. When the urine pellet is present, the proportional contribution from tumor cells may be higher in some instances.

Urine pellet analysis is normally analyzed by cytology. In embodiments, the urine pellet may be sequenced. The urine pellet may be sequenced similar to the cfDNA. In some instances, the urine pellet DNA may be fragmented (e.g., sonicated) to form DNA of smaller sizes to be sequenced by the same or similar techniques as cfDNA. Thus, analysis of the urine pellet may be used in the same or similar manner to detect a disease as with cf urine. Analysis of the urine pellet may increase specificity and/or sensitivity when combined with analysis of cf urine.

E. CNA and Global Hypomethylation can be Detected in the Urine but not the Plasma In two patients with bladder cancer with no evidence of metastasis, CNAs and hypomethylation was detected in the cfDNA of urine, but not the cfDNA of plasma.

FIGS. 28A-28D show Circos plot for the cf urine (FIGS. 28A and 28C) and the plasma (FIGS. 28B and 28D) from two bladder cancer patients (T22 and T23). The inner ring represents methylation density, and the outer ring represents copy number changes. Hypomethylation and copy number losses are colored red and lie toward the center of the ring, while hypermethylation and copy number gains are colored green and lie away from the center of the ring. Grey dots represent no significant deviation from controls. Urine and plasma samples were obtained at the same time. These figures show that detecting bladder cancer based on methylation level or copy number would be easier in cfDNA of urine compared to in cfDNA of plasma because methylation level and copy number aberrations do not show up or do not show up clearly in the plasma.

Figure 29A:
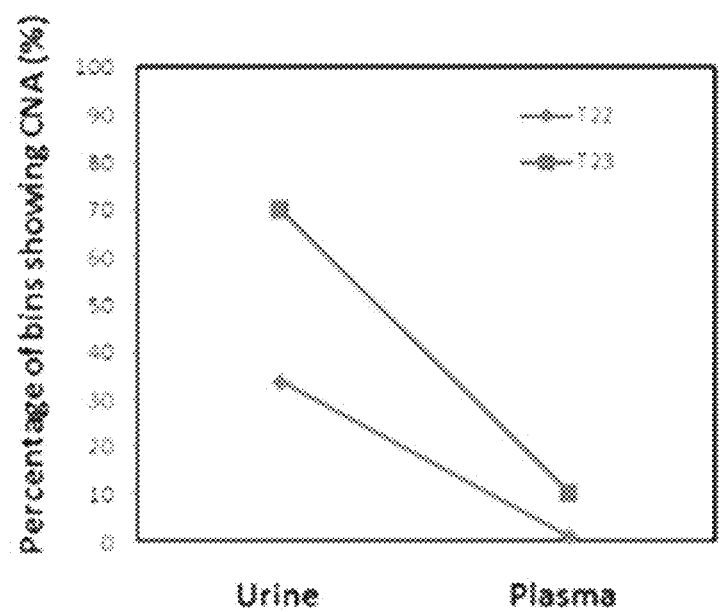
FIGS. 29A and 29B show the percentage of 1 MB bins across the genome that show evidence of CNAs or hypomethylation for the two bladder cancer cases, T22 and T23 according to embodiments of the present invention.
Figure 29B:
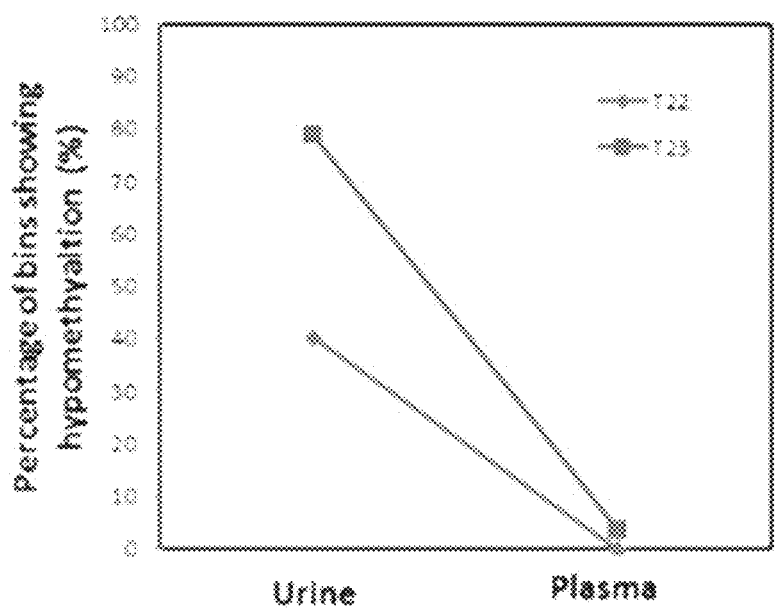

FIGS. 29A and 29B show the percentage of 1 MB bins across the genome that show evidence of CNAs or hypomethylation for the two bladder cancer cases, T22 and T23. For T23, there is evidence of CNAs in the plasma, for example at chromosome 5p. This copy number gain also visible in the cfDNA of urine, but other CNAs and the global hypomethylation is much more apparent in urine compared with plasma. T23 completed a course of neo-adjuvant chemotherapy but subsequently developed brain metastasis, ~6 months after radical cystectomy. These graphs also show that detecting bladder cancer based on methylation level or copy number would be easier in cfDNA of urine compared to in cfDNA of plasma because more bins show CNA or hypomethylation in urine than plasma.

F. Method of Identifying Cancer in a Particular Organ

Figure 30:
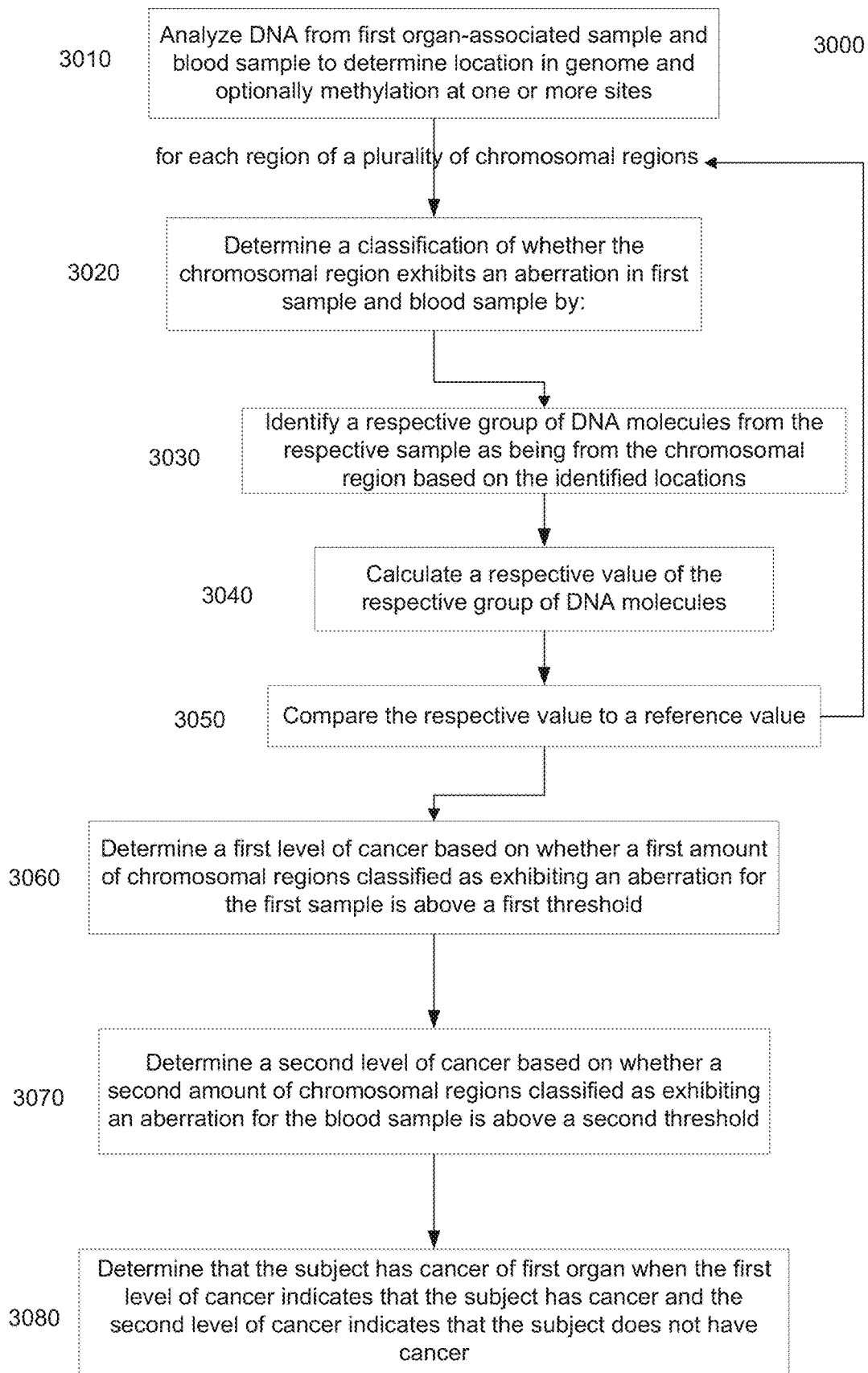
FIG. 30 is a flowchart illustrating a method of identifying bladder cancer in a subject by analyzing a urine sample and a blood sample of the subject according to embodiments of the present invention.

FIG. 30 is a flowchart illustrating a method 3000 of identifying cancer in a first organ of a subject by analyzing a first sample and a blood sample of the subject according to embodiments of the present invention. The first sample is from a first organ or passes through the first organ as the first sample exits the organism and is different from the blood sample. The first sample and the blood sample both include DNA originating from normal cells and potentially from cells associated with cancer. At least some of the DNA is cell-free in both the first sample and the blood sample. Examples of the first sample are urine, saliva, or stool.

At block 3010, a plurality of DNA molecules from the biological sample are analyzed. The analysis of a DNA molecule can include identifying a location of the DNA molecule in a genome of the organism and optionally (e.g., when a methylation analysis is performed) determining whether the DNA molecule is methylated at one or more sites. The methylation status can include whether a particular cytosine residue is 5-methylcytosine or 5-hydroxymethylcytosine.

The analysis can be performed by receiving sequence reads from a methylation-aware sequencing, and thus the analysis can be performed just on data previously obtained from the DNA. In other embodiments, the analysis can include the actual sequencing or other active steps of obtaining the data. The sequence reads can be obtained from various sequencing techniques, PCR-techniques, arrays, and other suitable techniques for identifying sequences of fragments. The methylation status of sites of the sequence read can be obtained as described herein.

One example of methylation-aware sequencing includes treating DNA with sodium bisulfite and then performing DNA sequencing. In another example, the methylation-aware sequencing can be performed without using sodium bisulfite, using a single molecule sequencing platform that would allow the methylation status of DNA molecules (including N6-methyladenine, 5-methylcytosine and 5-hydroxymethylcytosine) to be elucidated directly without bisulfite conversion (AB Flusberg et al. 2010 Nat Methods; 7: 461-465; J Shim et al. 2013 Sci Rep; 3:1389. doi: 10.1038/srep01389); or through the immunoprecipitation of methylated cytosine (e.g. by using an antibody against methylcytosine or by using a methylated DNA binding protein or peptide (LG Acevedo et al. 2011 Epigenomics; 3: 93-101) followed by sequencing; or through the use of methylation-sensitive restriction enzymes followed by sequencing. In another embodiment, non-sequencing techniques are used, such as arrays, digital PCR and mass spectrometry.

Blocks 3020-3050 are repeated for each chromosomal region of a plurality of chromosomal regions of the subject. The plurality of chromosomal regions can be non-overlapping. The genome could be separated into regions that are one megabase (Mb) in length, or other segment lengths such as 500 Kb or 2 Mb. A region can be 1 Mb in size, or some other equal-size. The entire genome can then include about 3,000 regions, each of which may be of predetermined size and location. Also, as mentioned above, such predetermined regions can vary to accommodate a length of a particular chromosome or a specified number of regions to be used, and any other criteria mentioned herein. If regions have different lengths, such lengths can be used to normalize results, e.g., as described herein.

At block 3020, a classification of whether the chromosomal region exhibits an aberration of a copy number aberration or hypomethylation is determined for each of the first sample and the blood sample. Block 3020 may be implemented by performing blocks 3030-3050. Further details about detection of copy number aberration or hypomethylation can be found in U.S. Pat. Nos. 8,741,811 and 9,121,069, and PCT publication WO2014/043763, which is incorporated by reference in its entirety.

At block 3030, a respective group of DNA molecules from the respective sample is identified as being from the chromosomal region based on the identified locations. The respective group including at least one DNA molecule located at each of a plurality of loci of the chromosomal region. In one embodiment, the group can be fragments that align to a particular haplotype of the chromosomal region, e.g., as described in U.S. Pat. No. 9,121,069, which is incorporated by reference in its entirety. In another embodiment, the group can be of any fragment that aligns to the chromosomal region, e.g., as also described in U.S. Pat. No. 9,121,069.

At block 3040, a computer system calculates a respective value of the respective group of DNA molecules. The respective value defines a property of the DNA molecules of the respective group. The property can be a methylation level, an amount of DNA molecules of the first respective group, or a statistical value of a size profile of the DNA molecules of the first respective group. As an example of an amount, the respective value can also be a normalized value, e.g., a tag count of the region divided the total number of tag counts for the sample or the number of tag counts for a reference region. The respective value can also be a difference or ratio from another value (e.g., for another haplotype), thereby providing the property of a difference for the region.

At block 3050, the respective value is compared to a reference value to determine a classification of whether the first chromosomal region exhibits an aberration, e.g., a copy number aberration of a deletion or an amplification, a methylation aberration of hypomethylation or hypermethylation, or a mismatch. This reference value can be any threshold or reference value described herein. For example, the reference value could be a threshold value determined for normal samples. When a difference between haplotypes is used, the respective value could be the difference or ratio of tag counts for the two haplotypes, and the reference value can be a threshold for determining that a statistically significant deviation exists. As another example, the reference value could be the tag count or size value for another haplotype or region, and the comparison can include taking a difference or ratio (or function of such) and then determining if the difference or ratio is greater than a threshold value.

The reference value can vary based on the results of other regions. For example, if neighboring regions also show a deviation (although small compared to one threshold, e.g., a z-score of 3), then a lower threshold can be used. For example, if three consecutive regions are all above a first threshold, then cancer may be more likely. Thus, this first threshold may be lower than another threshold that is required to identify cancer from non-consecutive regions. Having three regions (or more than three) having even a small deviation can have a low enough probability of a chance effect that the sensitivity and specificity can be preserved.

At block 3060, a first level of cancer is determined based on whether the first amount of chromosomal regions classified as exhibiting an aberration for the first sample is above a first threshold. As examples, a classification corresponding to the first level of cancer can be whether the organism has cancer, a stage of the cancer, and a prognosis of the cancer. In one embodiment, all aberrant regions are counted and a single threshold value is used regardless of where the regions appear. In another embodiment, a threshold value can vary based on the locations and size of the regions that are counted. For example, the amount of regions on a particular chromosome or arm of a chromosome may be compared to a threshold for that particular chromosome (or arm). Multiple thresholds may be used. For instance, the amount of aberrant regions on a particular chromosome (or arm) must be greater than a first threshold value, and the total amount of aberrant regions in the genome must be greater than a second threshold value.

At block 3070, a second level of cancer is determined based on whether a second amount of chromosomal regions classified as exhibiting an aberration for the blood sample is above a second threshold. Block 3070 may be performed in a similar manner as block 3060.

At block 3080, it is determined that the subject has cancer of the first organ when the first level of cancer indicates that the subject has cancer and the second level of cancer indicates that the subject does not have cancer. Such a scenario is exemplified in FIGS. 28A-28D. Accordingly, whole genome bisulphite sequencing is also able to identify global hypomethylation and copy number aberrations (CNA) in the cell-free urine and urine pellet of urothelial cancer patients. These changes correspond to those seen in the bladder tumor, and are not detectable in the systemic circulation.

After the determination of cancer, a treatment plan may be devised. The cancer may be treated by chemotherapy, drugs, diet, therapy, and/or surgery. In some cases the cancer may be treated earlier than without methods descried herein because the existence of the cancer may be detected earlier. The risk of complications, including death, may be reduced as a result of the detection methods.

G. Determining a Level of Cancer for CNA

The threshold value for the amount of regions in blocks 3060 and 3070 can depend on how strong the imbalance is for the regions counted. For example, the amount of regions that are used as the threshold for determining a classification of cancer can depend on the specificity and sensitivity (aberrant threshold) used to detect an aberration in each region. For example, if the aberrant threshold is low (e.g. z-score of 2), then the amount threshold may be selected to be high (e.g., 150). But, if the aberrant threshold is high (e.g., a z-score of 3), then the amount threshold may be lower (e.g., 50). The amount of regions showing an aberration can also be a weighted value, e.g., one region that shows a high imbalance can be weighted higher than a region that just shows a little imbalance (i.e. there are more classifications than just positive and negative for the aberration).

Accordingly, the amount (which may include number and/or size) of chromosomal regions showing significant over- or under-representation of a normalized tag count (or other respective value for the property of the group) can be used for reflecting the severity of disease. The amount of chromosomal regions with an aberrant normalized tag count can be determined by two factors, namely the number (or size) of chromosomal aberrations in the tumor tissues and the fractional concentration of tumor-derived DNA in the biological sample (e.g. plasma). More advanced cancers tend to exhibit more (and larger) chromosomal aberrations. Hence, more cancer-associated chromosomal aberrations would potentially be detectable in the sample (e.g. plasma). In patients with more advanced cancer, the higher tumor load would lead to a higher fractional concentration of tumor-derived DNA in the plasma. As a result, the tumor-associated chromosomal aberrations would be more easily detected in the plasma sample.

In the context of cancer screening or detection, the amount of chromosomal regions exhibiting over- or under-representation of normalized tag count (or other value) can be used to determine the possibility of the tested subject of having cancer. Using a cutoff of ±2 (i.e. z-score>2 or <−2), approximately 5% of the tested regions would be expected to give a z-score significantly deviating from the mean of the control subjects due to chance alone. When the whole genome is divided into 1 Mb segments, there would be approximately 3,000 segments for the whole genome. Thus, approximately 150 segments would be expected to have a z-score of >2 or <−2.

Thus, a cutoff (threshold) value of 150 for the number of segments with z-score >2 or <−2 can be used to determine if a cancer is present. Other cutoff values for the number of segments with aberration z-score (e.g., 100, 125, 175, 200, 250, and 300) can be chosen to fit the diagnostic purpose. A lower cutoff value, e.g. 100, would result in a more sensitive test but lower specificity and a higher cutoff value would be more specific but less sensitive. The number of false-positive classifications can be reduced by increasing the cutoff values of the z-score. For example, if the cutoff value is increased to 3, then only 0.3% of the segments would be falsely positive. In this situation, more than 3 segments with aberrant z-score can be used to indicate the presence of cancer. Other cutoff values can also be chosen, e.g. 1, 2, 4, 5, 10, 20, and 30, to fit different diagnostic purposes. However, the sensitivity of detecting the cancer-associated chromosomal aberrations would decrease with increasing the number of aberrant segments required for making a diagnosis.

One possible approach for improving the sensitivity without sacrificing the specificity is to take into account the result of the adjacent chromosomal segment. In one embodiment, the cutoff for the z-score remains to be >2 and <−2. However, a chromosomal region would be classified as potentially aberrant only when two consecutive segments would show the same type of aberrations, e.g. both segments have a z-score of >2. If the deviation of normalized tag count is a random error, the probability of having two consecutive segments being falsely positive in the same direction would be 0.125% (5%×5%/2). On the other hand, if a chromosomal aberration encompasses two consecutive segments, the lower cutoff value would make the detection of the over- or under-representation of the segments in the plasma sample more sensitive. As the deviation of the normalized tag count (or other value) from the mean of the control subjects is not due to random error, the consecutive classification requirement would not have significant adverse effect on the sensitivity. In other embodiments, the z-score of neighboring segments can be added together using a higher cutoff value. For example, the z-scores of three consecutive segments can be summed and a cutoff value of 5 can be used. This concept can be extended to more than three consecutive segments.

The combination of amount and aberrant thresholds can also depend on the purpose of the analysis, and any prior knowledge of the organism (or lack thereof). For example, if screening a normal healthy population for cancer, then one would typically use high specificity, potentially in both the amount of regions (i.e. high threshold for the number of regions) and an aberrant threshold for when a region is identified as having an aberration. But, in a patient with higher risk (e.g. a patient complaining of a lump or family history, smoker, HPV virus, hepatitis virus, or other viruses) then the thresholds could be lower in order to have more sensitivity (less false negatives).

In one embodiment, if one uses a 1-Mb resolution and a lower detection limit of 6.3% of tumor-derived DNA for detecting a chromosomal aberration, the number of molecules in each 1-Mb segment would need to be 60,000. This would be translated to approximately 180 million (60,000 reads/Mb×3,000 Mb) alignable reads for the whole genome.

H. Determining a Level of Cancer for Methylation

For methylation, aspects can be the same as for CNA. In one embodiment, a methylation level for all regions can be determined and compared to a threshold value.

In some embodiments, the first methylation level can correspond to a number of regions whose methylation levels exceed the reference value. For example, a plurality of regions of a genome of the organism can be identified. The regions can be identified using criteria mentioned herein, e.g., of certain lengths or certain number of sites. One or more sites (e.g., CpG sites) can be identified within each of the regions. A region methylation level can be calculated for each region. The first methylation level is for a first region. Each of the region methylation levels is compared to a respective region cutoff value, which may be the same or vary among regions. The region cutoff value for the first region is the first cutoff value. The respective region cutoff values can be a specified amount (e.g., 0.5) from a reference methylation level, thereby counting only regions that have a significant difference from a reference, which may be determined from non-cancer subjects.

A first number of regions whose region methylation level exceeds the respective region cutoff value can be determined, and compared to a threshold value to determine the classification. In one implementation, the threshold value is a percentage. Comparing the first number to a threshold value can include dividing the first number of regions by a second number of regions (e.g., all of the regions) before comparing to the threshold value, e.g., as part of a normalization process.

As described above, a fractional concentration of tumor DNA in the biological sample can be used to calculate the first cutoff value. The fractional concentration can simply be estimated to be greater than a minimum value, whereas a sample with a fractional concentration lower than the minimum value can be flagged, e.g., as not being suitable for analysis. The minimum value can be determined based on an expected difference in methylation levels for a tumor relative to a reference methylation level. For example, if a difference is 0.5 (e.g., as used as a cutoff value), then a certain tumor concentration would be required to be high enough to see this difference.

V. COMBINATION OF CNA, GLOBAL METHYLATION, AND TUMOR CONTRIBUTION

Genomewide bisulfite sequencing allows the simultaneous assessment of global methylation status, copy number aberrations (CNA), and bladder tumor contribution by methylation deconvolution. We assessed the ability for these analytical methods to detect bladder cancer in 46 bladder cancer patients and 39 controls. We established the upper limit of normal based on the mean value of controls, plus three standard deviations. No controls tested positive using these criteria, giving a specificity of 100%.

A. Sensitivity and Specificity Results for Parameter Combinations

Figures 31A, 31B, 31C:
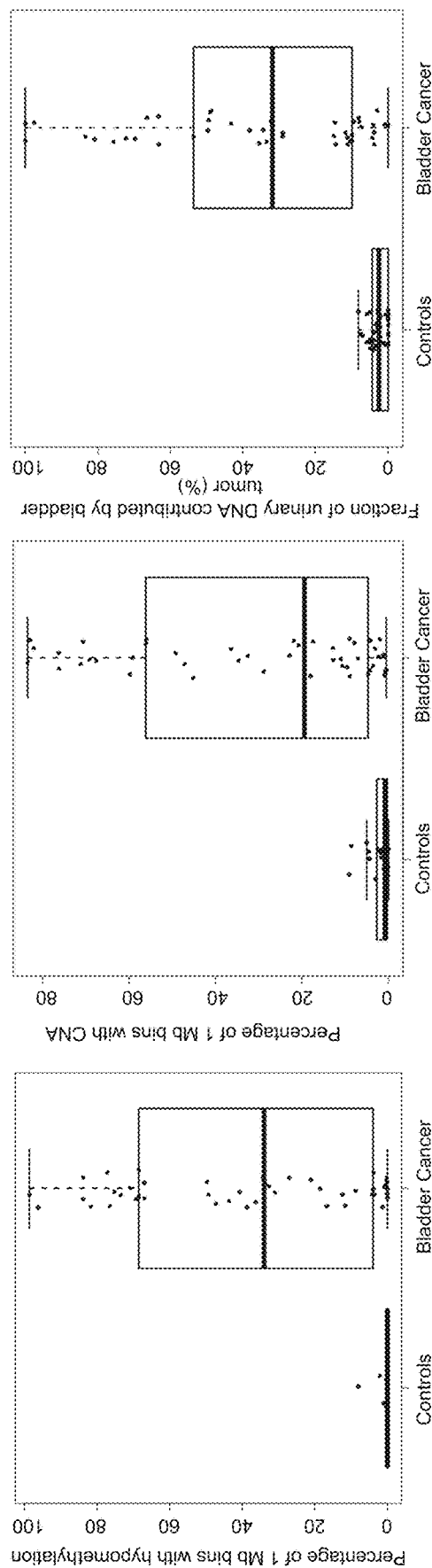
FIGS. 31A-31C show boxplots for the percentage of 1 mb bins with hypomethylation, percentage of 1 mb bins with copy number aberrations, and bladder tumor contribution from methylation deconvolution for 46 bladder cancer patients and 39 controls according to embodiments of the present invention.
Figure 31F:
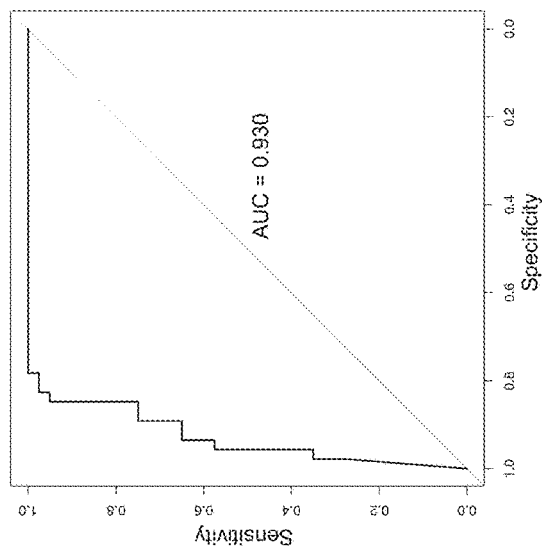
FIGS. 31D-31F show receiver operating characteristic (ROC) curves for hypomethylation, CNA, and bladder tumor contribution according to embodiments of the present invention.
Figure 31E:
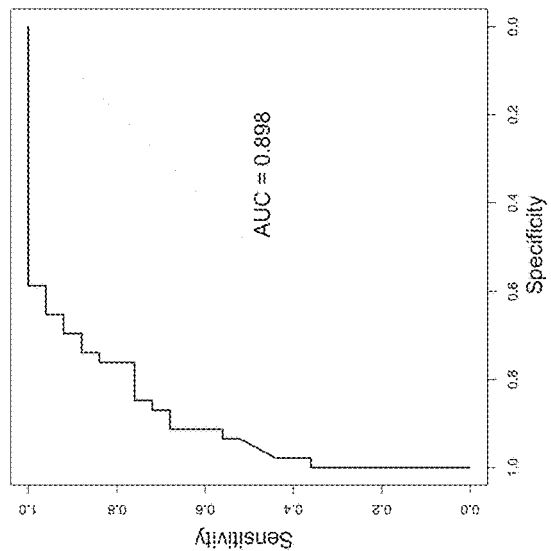
Figure 31D:
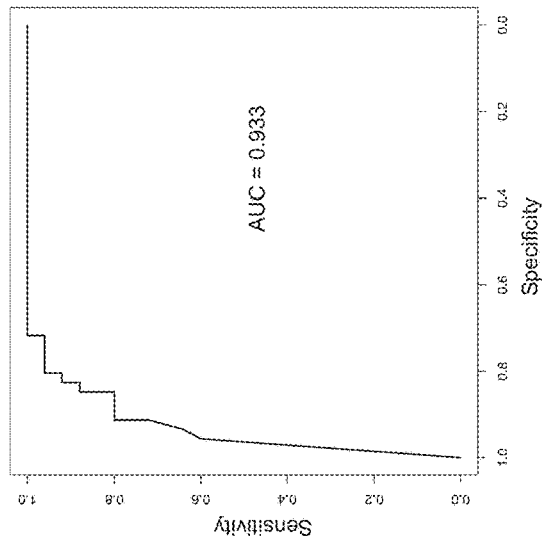

FIG. 31A-31C show the boxplots for the percentage of 1 mb bins with hypomethylation, percentage of 1 mb bins with copy number aberrations and bladder tumor contribution from methylation deconvolution, respectively for 46 bladder cancer patients and 39 controls. FIG. 31D-31F show the corresponding ROC curve for hypomethylation, where FIG. 31D shows the ROC curve corresponding to FIG. 31A, FIG. 31E shows the ROC curve corresponding to FIG. 31B, and FIG. 31F shows the ROC curve corresponding to FIG. 31C. Bladder tumor contribution was derived using tissue-specific methylation signatures and also non-tissue-specific methylation signatures that varied across different tissues.

The proportion of 1 mb bins with hypomethylation (FIG. 31A), CNA (FIG. 31B), and the bladder tumor contribution (FIG. 31C) was significantly higher in bladder cancer cases compared with controls (Mann Whitney U test P<0.001). Using the mean plus three standard deviations of the controls as the upper limit of normal, no controls tested positive. Using the same cutoffs, 43 of 46 bladder cancer cases could be identified with at least one of the three parameters.

Using the percentage of 1 mb bins with significant hypomethylation, we were able to detect of bladder cancer with a sensitivity of 71.7% (ROC AUC=0.93) (FIG. 31D). Using percentage of 1 mb bins with significant CNA, we were able to detect bladder cancer with a 63.0% (ROC AUC=0.90) (FIG. 31E). Using the bladder tumor contribution from methylation deconvolution, we were able to detect bladder cancer with a sensitivity of 78.3% (ROC AUC=0.93) (FIG. 31F). The three parameters may be combined by considering cancer detected if any one of the three parameters indicates cancer. By combining all three parameters, the sensitivity was increased to 93.4% for bladder cancer cases testing positive for at least one of the three parameters. The specificity was 100%. By combining all three parameters, all 29 cases with high grade or invasive disease (T1 or above) could be detected.

The parameters may be combined by considering cancer detected if any combination of the parameters indicates cancer. In some embodiments, a minimum number of parameters may be required for the detection of cancer. For example, two, three, or more parameters may be required. Some embodiments may require a certain parameter (e.g., CNA, hypomethylation, or deconvolution) to indicate cancer in order for cancer to be detected. Table 6 shows detection results when combining parameters:

TABLE 6

Sensitivity results using different combinations of parameters.

|  | Hypo-methlation | CNA | Decon-volution | Hypo-methylation OR CNA | Hypo-methylation OR Deconvolution | CNA OR Decon-volution | Hypo-methylation OR CNA OR Deconvolution |
|---|---|---|---|---|---|---|---|
| Detected | 35 | 31 | 37 | 38 | 42 | 39 | 43 |
| Missed | 11 | 15 | 9 | 8 | 4 | 7 | 3 |
| Sensitivity | 0.74 | 0.63 | 0.80 | 0.80 | 0.91 | 0.85 | 0.93 |

These results can be compared with urine cytology, the current standard of care. Forty-two of the 46 bladder cancer patients had one to three urine samples sent for urine cytology within the six months before urologic surgery as part of routine care. Only four of the 42 bladder cancer patients (9.5%) had positive urine cytology. The four cases with positive urine cytology had invasive (T2b-4) high grade disease. Urine cytology was less accurate in detecting bladder cancer than using hypomethylation, CNA, and/or bladder tumor contribution.

As an example, we sequenced 17 bladder cancer cases with noninvasive low grade disease (Ta LG). We assessed the ability for analytical methods to detect low grade disease.

Figures 32A, 32B, 32C:
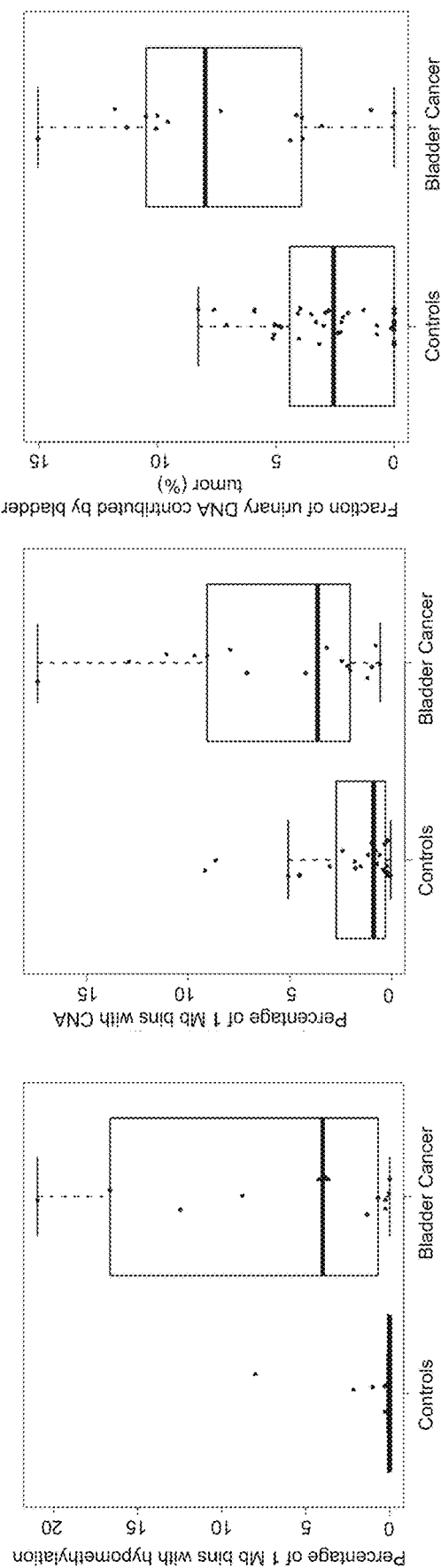
FIGS. 32A-32C show boxplots for the percentage of 1 mb bins with hypomethylation, percentage of 1 mb bins with copy number aberrations, and bladder tumor contribution from methylation deconvolution for 17 bladder cancer patients with noninvasive (Ta) low grade disease and 39 controls according to embodiments of the present invention.
Figure 32F:
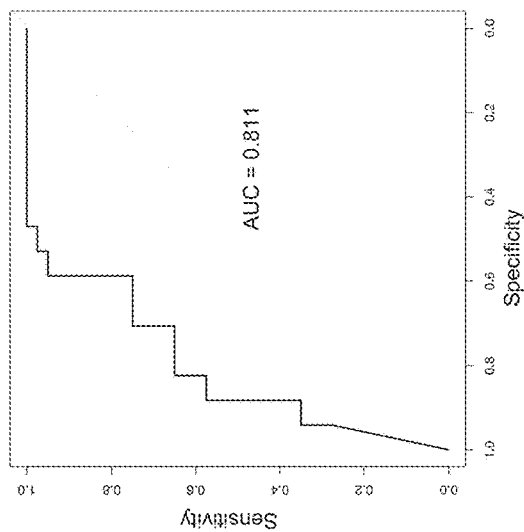
FIGS. 32D-32F show receiver operating characteristic (ROC) curves for hypomethylation, CNA, and bladder tumor contribution according to embodiments of the present invention.
Figure 32E:
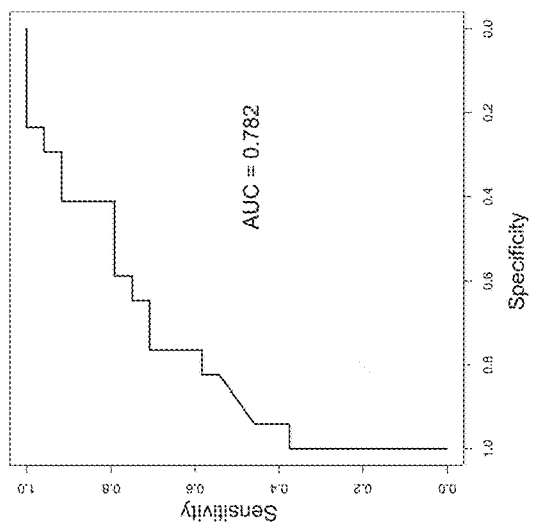
Figure 32D:
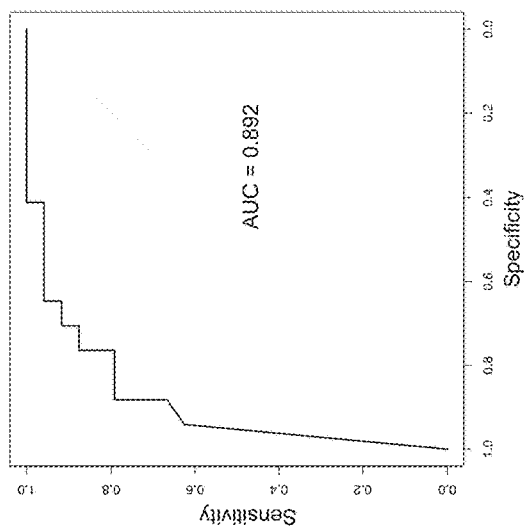

FIGS. 32A, 32B, and 32C show the boxplots for the percentage of 1 mb bins with hypomethylation, percentage of 1 mb bins with copy number aberrations, and bladder tumor contribution from methylation deconvolution, respectively for 17 bladder cancer patients with noninvasive (Ta) low grade disease, and 39 controls. FIG. 32D shows the corresponding ROC curve for FIG. 32A. FIG. 32E shows the corresponding ROC curve for FIG. 32B. FIG. 32F shows the corresponding ROC curve for FIG. 32C. Using at least one of the three parameters, 14 of the 17 patients with noninvasive low grade disease could be identified.

Using the percentage of 1 mb bins with significant hypomethylation, we were able to detect of bladder cancer with a sensitivity of 41.1% (ROC AUC=0.89) (FIG. 32D). Using percentage of 1 mb bins with significant CNA, we were able to detect bladder cancer with a 17.6% (ROC AUC=0.78) (FIG. 32E). Using the bladder tumor contribution from methylation deconvolution, we were able to detect bladder cancer with a sensitivity of 47.0% (ROC AUC=0.81) (FIG. 32F). By combining all three parameters, the sensitivity was increased to 82.4% for bladder cancer cases testing positive for at least one of the three parameters. The specificity was 100%.

More than three parameters may also be used. Table 7 shows the sensitivity and specificity of up to five parameters: hypomethylation, CNA, deconvolution, hypermethylation, mutational load using 1 mismatch using different cutoffs and in combination. The cutoffs demonstrated are the mean of controls plus 3 standard deviations (SD) and the mean of controls plus 2 SD. The parameters can be combined using 'OR' (test positive if positive in at least one of the parameters) or using 'AND' (test positive if positive in all 5 parameters).

A leave one out analysis can be used to test the performance of the logistic regression model. In such an analysis, one sample is used as the testing sample. All other samples are used as a training set to fit the logistic regression model, thereby obtaining the parameters (e.g., coefficients and threshold) of the model. A second sample is then used as the testing sample and all other samples are used as the training set to determine the coefficients. This procedure is then repeated for each sample in turn.

In some embodiments, using logistic regression based on a probability of 0.5 as the cutoff for having cancer, the probability of having a cancer=$1-1/(1+\exp[-(-0.4413124*\text{Hypomethylation} - 0.68652846*\text{CNA} - 0.44981374*\text{Tumor fractional contribution} + 1.02332221*\text{hypermethylation} + 0.07711755*\text{mismatch loading} + 1.35436873)])$.

By adjusting the cutoff to the mean plus 3 SD, a sensitivity of 95.7% and specificity of 100% can be achieved. In other embodiments, other classification algorithms can be used, for example, but not limited to decision tree, supporter vector machine, naïve Bayes classifier, K-nearest neighbor, random forest tree and all other machine learning algorithms. Thus, analytical methods described herein may be used to detect low grade disease.

Figure 33:
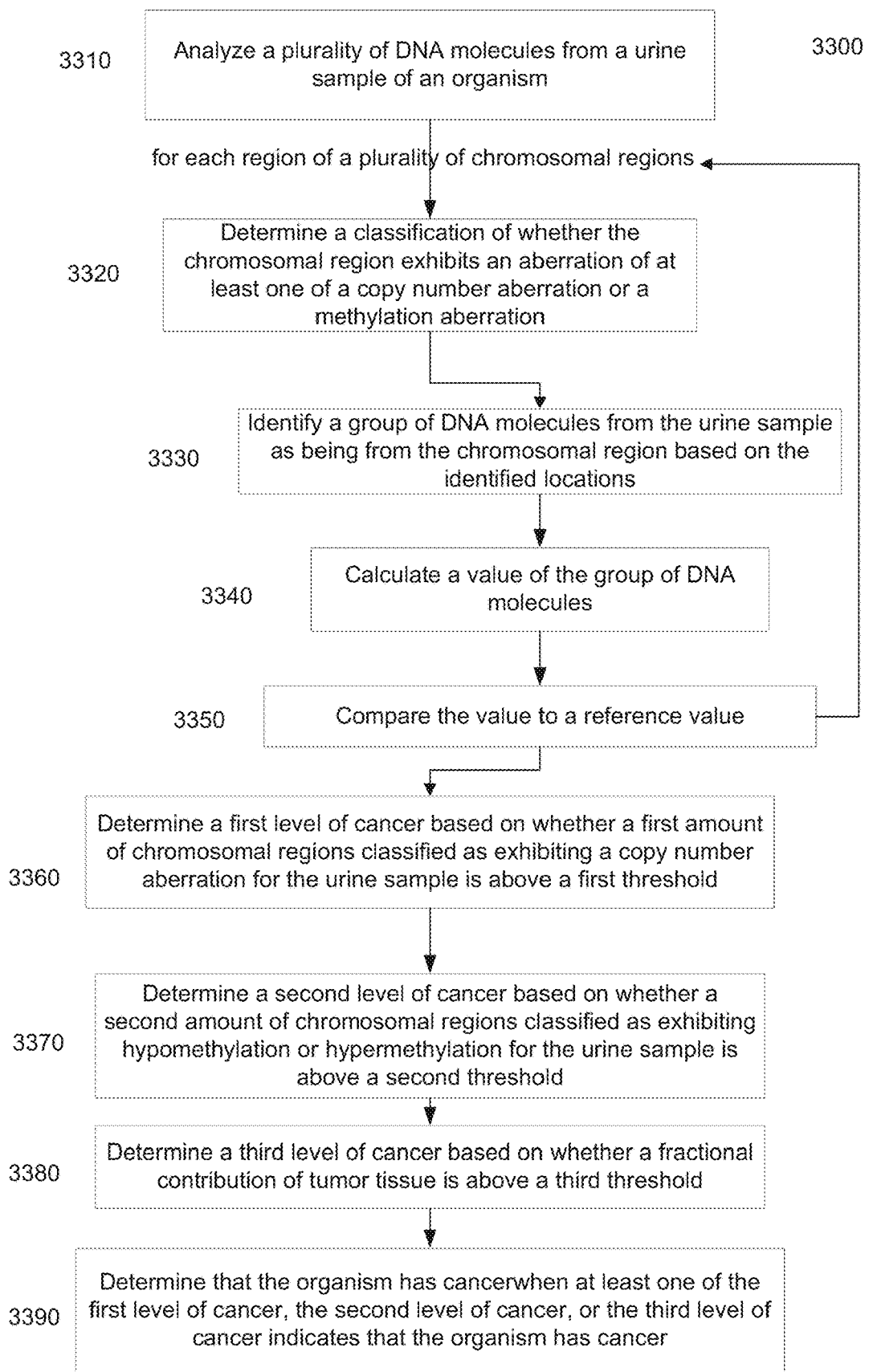
FIG. 33 shows a method of analyzing a urine sample of an organism according to embodiments of the present invention.

B. Method of Analyzing Urine Sample Using CNA, Global Methylation, and Tumor Contribution FIG. 33 shows a method 3300 of analyzing a urine sample of an organism. The organism may be any organism described herein. The urine sample may include DNA originating from normal cells and potentially from cells associated with cancer. At least some of the DNA may be cell-free in the urine sample.

At block 3310, a plurality of DNA molecules from the urine sample are analyzed. Analyzing the DNA molecule may include identifying a location of the DNA molecule in a genome of the organism. Identifying the location may be by a computer system.

At block 3320, a classification of whether the chromosomal region exhibits an aberration of at least one of a copy number aberration or a methylation aberration for each chromosomal region of a plurality of chromosomal regions of the organism is determined. The methylation aberration may be hypomethylation or hypermethylation. In some

TABLE 7

Sensitivity results using different combinations of five parameters.

|  | Hypo-methylation | CNA | Decon-volution | Hyper-methylation | 1 mismatch mutational load | 5 parameters using 'OR' | 5 parameters using 'AND' |
|---|---|---|---|---|---|---|---|
| Mean + 3SD Sensitivity | 76.1% | 67.4% | 80.4% | 19.6% | 17.4% | 95.7% | 4.3% |
| Mean + 3SD Specificity | 100.0% | 100.0% | 100.0% | 100.0% | 100.0% | 100.0% | 100.0% |
| Mean + 2SD Sensitivity | 80.4% | 71.7% | 84.8% | 37.0% | 34.8% | 95.7% | 13.0% |
| Mean + 2SD Specificity | 94.9% | 94.9% | 92.3% | 92.3% | 92.3% | 82.1% | 100.0% |

Using the mean of the controls plus 2 SD as a cutoff and combining the five parameters using 'OR,' a sensitivity of 95.7% and specificity of 82.1% can be achieved. Alternatively, using a logistic regression model, a sensitivity of 91.3% and a specificity of 89.7% can be achieved, based on the leave one out analysis.

embodiments, the aberration may include only one of hypomethylation or hypermethylation. For example, the aberration may be at least one of a copy number aberration or hypomethylation. In some embodiments, a classification is determined of whether the chromosomal region exhibits an aberration of a mismatch.

At block 3330, the classification may be determined by identifying a group of DNA molecules from the urine sample as being from the chromosomal region based on the identified locations. The group may include at least one DNA molecule located at each of a plurality of loci of the chromosomal region.

At block 3340, the classification may also be determined by calculating, with a computer system, a value of the group of DNA molecules. The respective value may define a property of the DNA molecules of the respective group. The property may be at least one of a copy number or a methylation level. Optionally, the property may be a mismatch mutational load, as described herein.

At block 3350, the classification may further be determined by comparing the value to a reference value. The reference value may determine a cutoff between a normal value from an aberration. The reference value may be based on a z-score of 3. For example, the reference value may be a value of copy number beyond which would be considered a copy number aberration. In some examples, the reference value may be a value of methylation level beyond which the region would be considered hypermethylated or hypomethylated.

At block 3360, a first level of cancer may be determined based on whether a first amount of chromosomal regions classified as exhibiting a copy number aberration for the urine sample is above a first threshold. The first threshold may divide organisms known to have cancer from organisms that may or may not have cancer. In other embodiments, the first threshold may divide organisms known not to have cancer from organisms that may or may not have cancer.

At block 3370, a second level of cancer may be determined based on whether a second amount of chromosomal regions classified as exhibiting hypomethylation or hypermethylation for the urine sample is above a second threshold. The second threshold may be similar to the first threshold, except the second threshold may apply to methylation level instead of a copy number.

At block 3380, a third level of cancer may be determined based on whether a fractional contribution of tumor tissue is above a third threshold. Method 3300 may further include determining the fractional contribution of the tumor tissue. In various embodiments, the fractional contribution may be determined by using tumor-specific somatic mutations, tumor-specific methylation signature, tumor-specific fragment end patterns, or fragment size analysis (e.g., tumor DNA is statistically longer than non-tumor DNA). Further details on determining fractional contribution using tumor-specific somatic mutations is described in U.S. Patent Publication No. 2014/0100121. Further details on using a tumor-specific methylation signature is described in U.S. Patent Publication No. 2014/0080715 and 2016/0017319 and PCT Patent Publication No. WO2014/043763. Further details on using tumor-specific fragment end patterns is described in U.S. Patent Publication No. 2017/0024513. Further details on using fragment size analysis is described in U.S. Patent Publication No. 2016/0201142. The contents of all of these patent applications are incorporated herein by reference for all purposes. The fractional contribution of tumor tissue may also be determined by a deconvolution method described herein. The third threshold may be similar to either the first threshold or the second threshold, except the third threshold may apply to fractional contribution instead of copy number or methylation level.

Additional thresholds may be additional levels of cancer. For example, a level of cancer may be determined based on whether an amount of chromosomal regions classified as exhibiting a mismatch is above a threshold.

At block 3390, the organism may be determined to have cancer when at least one of the first level of cancer, the second level of cancer, or the third level of cancer indicates that the organism has cancer. The organism may be determined to have cancer when at least two of the levels or three of the levels indicate the organism has cancer. Additional levels of cancer may be used. The organism may be determined to have cancer when at least one of the levels indicates the organism has cancer. In some embodiments, the organism may be determined to have cancer when all the levels indicate the organism has cancer. In other embodiments, the organism may be determined to have cancer when over 50%, 60%, 70%, 80%, or 90% of the levels indicate the organism has cancer.

Method 3300 may include treating the organism in any manner described herein.

VI. ESTIMATING TUMOR LOAD USING MISMATCHES AND SHALLOW DEPTH SEQUENCING

We utilized the proportion of reads with one mismatch to estimate the tumor load using shallow depth sequencing. This can be used to differentiate bladder cancer cases from normal controls. Urothelial carcinomas are characterized by the accumulation of somatic mutations. Bladder cancers may have a high rate of somatic mutation (about 8 mutations per megabase) (Glaser et al., Nat. Rev. Urol., 2017). Urinary cfDNA originating from the bladder tumor in bladder cancer patient may have an increased proportion of fragments that show mismatch compared to the reference genome. Mismatches compared with the reference genome can arise due to germline variation, somatic mutation, or sequencing error. Genomewide bisulfite sequencing at less than 1× coverage of the human genome is insufficient to accurately identify somatic mutations, though the number of reads with mismatches compared to the reference genome can be assessed. Urinary cfDNA from bladder cancer cases and controls will harbor common germline variation, which can be detected as mismatches to the reference genome. On top of this, the higher incidence of somatic mutations in bladder cancer cases can contribute to a larger proportion of reads with a single mismatch compared with the human reference genome.

Figure 34B:
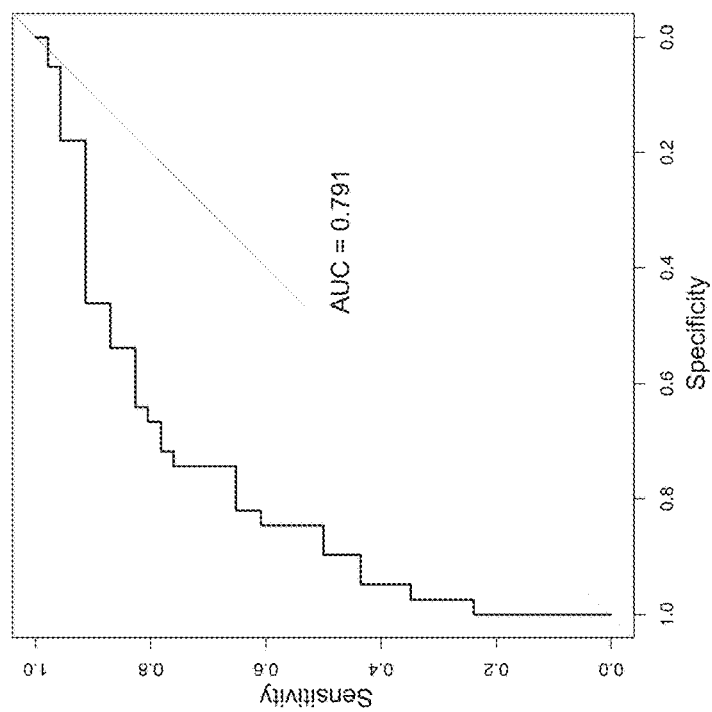
FIG. 34B is the corresponding ROC curve analysis for FIG. 34A according to embodiments of the present invention.
Figure 34A:
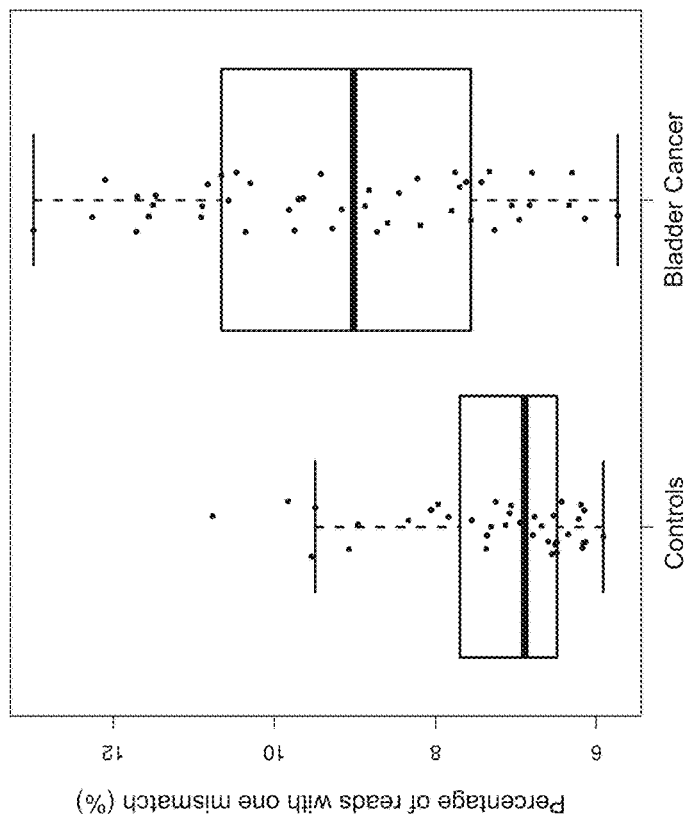
FIG. 34A is a boxplot for the percentage of reads with one mismatch in 49 bladder cancer cases and 39 controls according to embodiments of the present invention.

FIG. 34A is a boxplot for the percentage of reads with one mismatch in 49 bladder cancer cases and 39 controls. The boxplot shows that bladder cancer cases have a higher percentage of reads with one mismatch compared with controls (Mann Whitney U test P<0.001). FIG. 34B shows the ROC curve has an AUC of 0.79. Proportion of reads with a mismatch may be used to detect bladder cancer.

Figure 35:
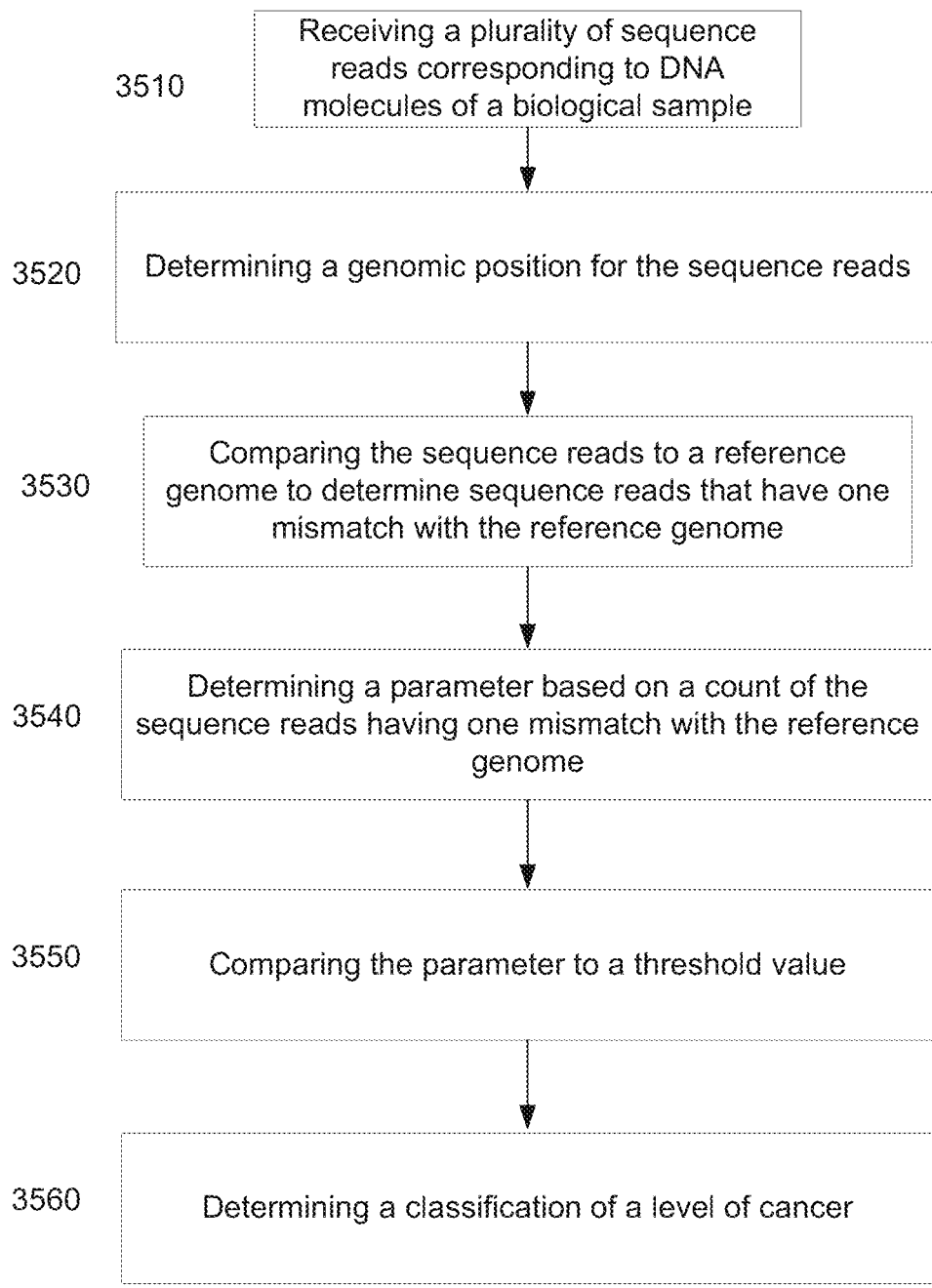
FIG. 35 shows a method of analyzing a biological sample of an organism according to embodiments of the present invention.

FIG. 35 shows a method 3500 of analyzing a biological sample of an organism. The biological sample may include DNA originating from normal cells and potentially from cells associated with cancer. At least some of the DNA may be cell-free in the biological sample. The biological sample may be a urine sample.

At block 3510, a plurality of sequence reads corresponding to DNA molecules of the biological sample are received. The sequence reads may be from genomewide bisulfate sequencing. The sequence reads may be at a depth coverage below 1×, from 1× to 2×, from 2× to 3×, from 3× to 5×, or from 5× to 10×. The plurality of sequence reads may be less than 80 million uniquely mappable reads, including less than 50 million uniquely mappable reads, less than 40 million uniquely mappable reads, less than 30 million uniquely mappable reads, or less than 20 million uniquely mappable reads.

At block 3520, a genomic position for the sequence reads is determined, e.g., as described herein. For instance, the genomic position can be determined using a computer based on a reference genome. The reference genome may be a reference genome for a population or a representative corresponding to the organism (e.g., a human). In another embodiment, the reference genome may be specific to the subject by including the germline (constitutional) genome for the organism.

At block 3530, the sequence reads are compared to a reference genome to determine a sequence reads that have one mismatch with the reference genome. As examples, the mismatch may be the result of a somatic mutation, a sequencing error, or a natural mismatch (e.g., a polymorphism resulting from a difference in the germline genome of the subject and a reference genome). Multiple mismatches per sequence read may be used, but the performance may be worse than using only one mismatch. Each DNA molecule is generally less than 100 bp and the probability of observing two or more true somatic mutations in a short stretch of DNA is low.

At block 3540, a parameter is determined based on a count of the sequence reads having one mismatch with the reference genome. In some embodiments, the count of sequence reads may be of sequence reads with no more than one mismatch. In other embodiments, the count of sequence reads may include sequence reads with one or more mismatches, e.g., two, three, or more mismatches. The parameter may be a normalized count of the sequence reads having one mismatch. For example, the parameter may be a density, concentration, or percentage of sequence reads having one mismatch. In some instances, the parameter may equal count of sequence reads having one mismatch.

At block 3550, the parameter is compared to a threshold value. The threshold value may be determined using data on mismatches for a healthy organism and/or data on mismatches for an organism with cancer. For example, the threshold value may be set at 1, 2, or 3 standard deviations above an average parameter for a population of healthy organisms.

At block 3560, a classification of a level of cancer is determined using the comparison of the parameter to the threshold value. If the parameter is above the threshold value, the classification of a level of cancer may be that the organism has cancer. Additional classification can be used, as described herein. For example, other classifications of a level of cancer may use a copy number aberration, hypomethylation, hypermethylation, or tumor contribution, which may be determined according to methods described herein. For example, detecting cancer may include a parameter other than one based on mismatches.

Method 3500 may exclude determining whether the mismatch is a sequence error. By not determining the reason for the mismatch, determining the classification of a level of cancer may be more efficient without a substantial decrease in accuracy.

Method 3500 may include treating cancer by any technique described herein.

VII. URINE METAGENOMIC ANALYSIS CAN IDENTIFY BLADDER CANCER CASES AND CONTROLS

Studies of urinary microbiota have proposed that microorganisms in the urinary tract are associated with urologic diseases besides urinary tract infections. We conducted metagenomic analysis of sequenced cfDNA reads that were not mapped to the human genome. Unmapped reads were mapped to a reference of 1M marker genes present in pathogens. Pathogens may include ~13,500 bacterial and archaeal genomes and ~3,500 viral genomes and may be mapped using BSMap. An average of 25,000 reads could be mapped to the marker gene reference, per sample. Metaphlan2 was used to identify the proportional contribution from different microorganisms in an abundance species table.

Figure 36:
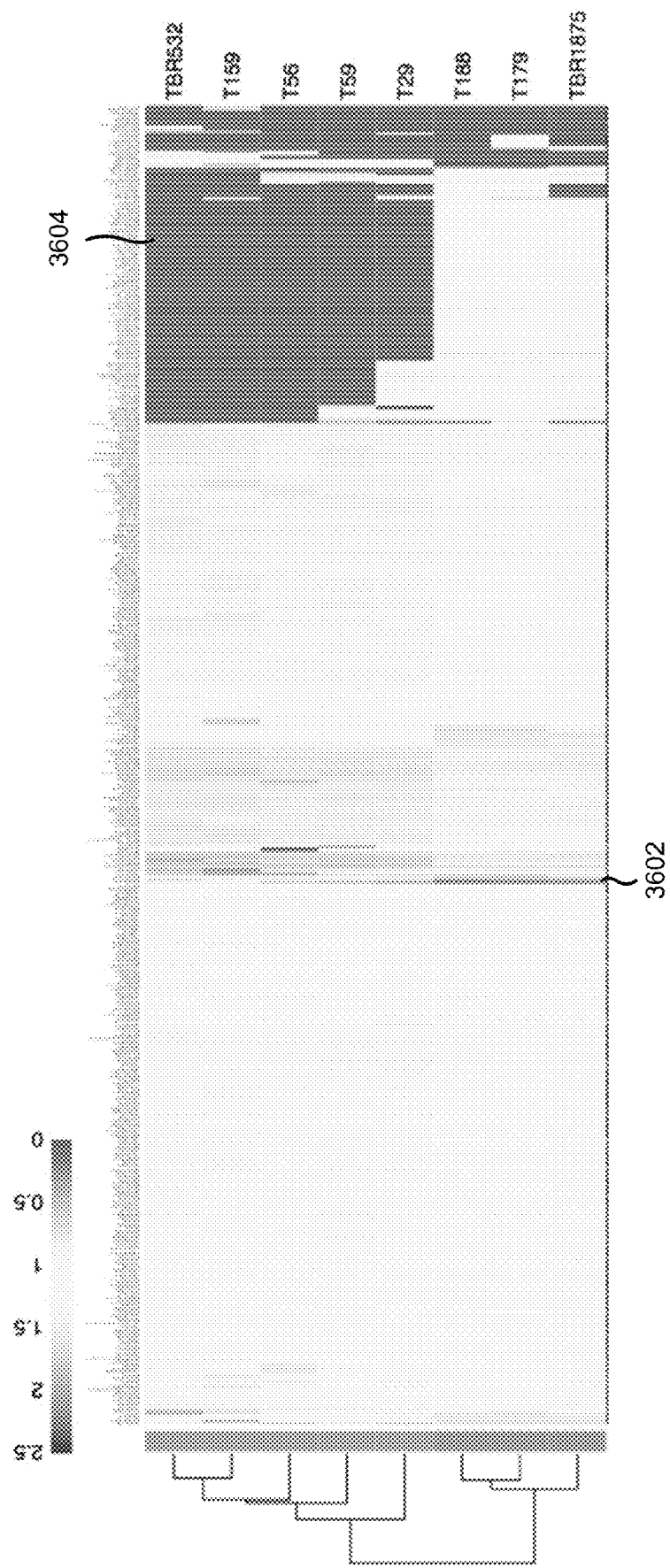
FIG. 36 is a heat map displaying the relative abundance of different microorganism species for three bladder cancer cases and five controls according to embodiments of the present invention.

FIG. 36 shows a heat map displaying the relative abundance of different microorganism species for three bladder cancer cases and five controls. Relative abundance can be defined as reads mapped to a particular species/total number of reads mapped to the metagenomic database divided by size of a particular microbex1e9 (RPKM). The three bladder cancer cases were T188, T179, and TBR1875. The five controls were TBR532, T159, T56, T59, and T29. Each vertical line represents a single species. The color represents the log percentage abundance for each species such that red (e.g., section 3602) represents high, and blue (e.g., section 3604) represents low proportional contribution. FIG. 36 shows that bladder cancer cases and controls could be separated. Species that were more abundant in bladder cancer cases than in controls include: *Halonotius, Thermococcus, Nitrosopumilus* and *Actinomyces*. Species that were more abundant in control than in bladder cancer cases include: *Brevibacterium* and *Nocardioides*. As a result, cfDNA reads that do not map to the human genome may be used to detect bladder cancer.

The top microbes showing differential relative abundance in bladder cancer cases compared with controls include the following bacteria: *Granulicella, Actinobaculum schaalii, Mycobacterium tuberculosis/bovis/africanum/canetti, actinobacterium, Ilumatobacter coccineus, Candidatus Koribacter, Mobiluncus curtisii, Acidimicrobium ferrooxidans, Candidatus Chloracidobacterium thermophilum, Candidatus Korarchaeum cryptofilum, Methanobacterium, Salinispora pacifica, Methanocella conradii, Brevibacterium,* and *Mycobacterium*.

The top microbes also include the following archaea: *Methanoculleus, Methanocaldococcus, Methanolinea tarda, Thermoplasma volcanium, Methanosphaerula palustris, Sulfolobus acidocaldarius, Methanosphaera stadtmanae, Methanoplanus petrolearius, Methanocella arvoryzae, Methanofollis liminatans,* and *Methanococcus aeolicus*.

Figure 37:
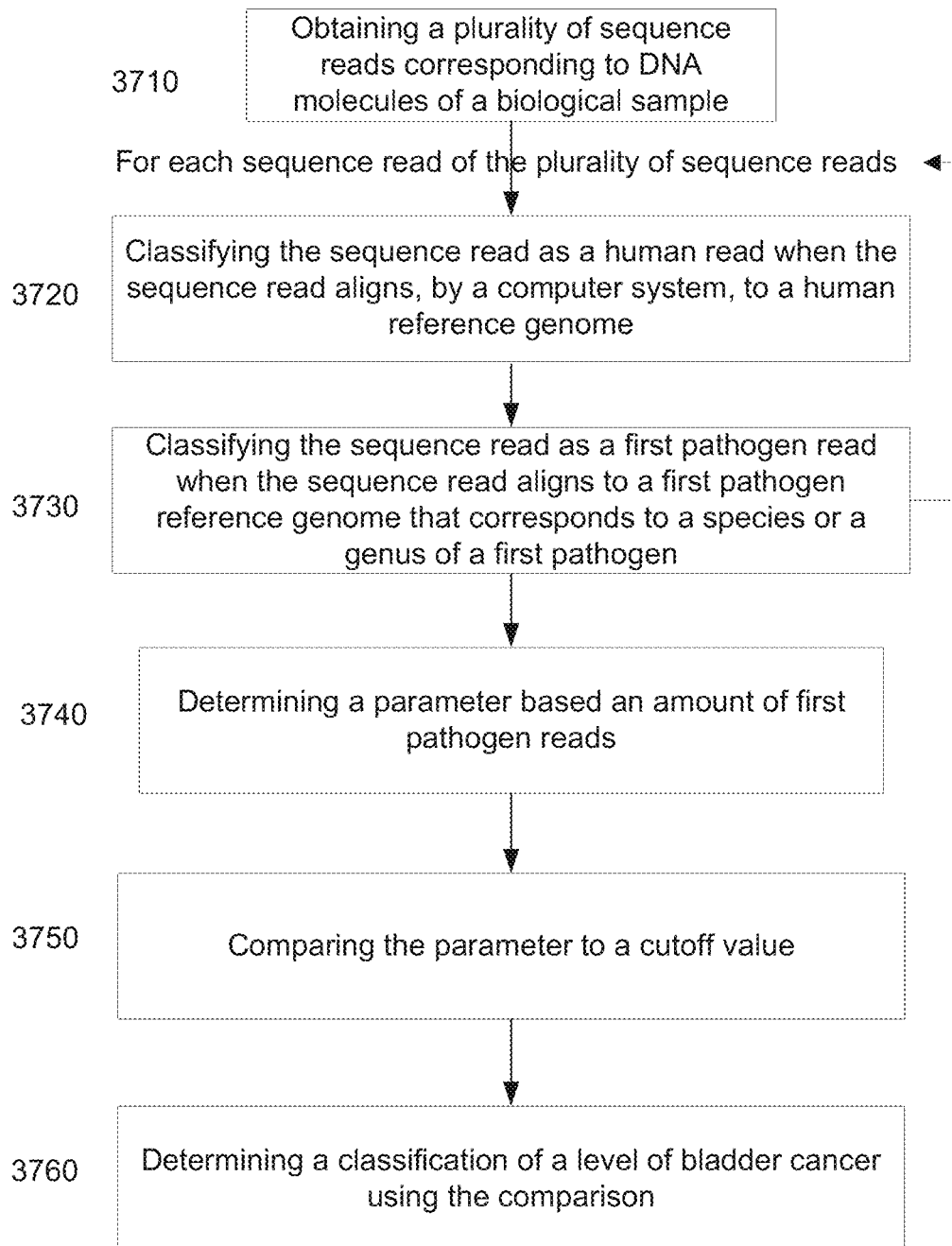
FIG. 37 shows a method of analyzing a urine sample of a human according to embodiments of the present invention.

FIG. 37 shows a method 3700 of analyzing a urine sample of a human. The urine sample may include DNA originating from normal cells and potentially from cells associated with cancer. At least some of the DNA may be cell-free in the urine sample.

At block 3710, a plurality of sequence reads corresponding to DNA molecules of the urine sample is obtained. Block 3710 can be performed in a similar manner as other sample measurement steps described herein.

At block 3720, for each sequence read of the plurality of sequence reads, the sequence read may be aligned to a human reference genome by a computer system. When the sequence read aligns to the human reference genome, the sequence read is classified as a human read. The sequence read may be considered aligned when there are less than or equal to two mismatches per read. In some instances, a higher number of mismatches may be allowed. The human reference genome may be from the same ethnic or racial group (e.g., east Asian, European) of the human that provided the urine sample. The reference genome may be from a public database (e.g., NCBI or UCSC). The reference genome may also be a de novo assembly for the human from which the urine sample was obtained. In other words, a personal reference genome when the human is known to be free of cancer may be used.

At block 3730, for each sequence read of the plurality of sequence reads, the sequence read may be aligned, by the computer system, to a first pathogen reference genome that corresponds to a species or a genus of a first pathogen. When the sequence read aligns to the first pathogen reference genome, the sequence read is classified as a first pathogen read. A plurality of pathogen reference genomes may be tested, including bacterial, viral, and archaeal reference genomes. The specific pathogen reference genome to use can depend on a prevalence of a particular species or genus, and whether different species indicate different classifications of bladder cancer. For example, if the species all indicate bladder cancer and the prevalence is relatively low, then a genus reference can be constructed from homologous parts of the genomes from the species of the genus.

Method 3700 may include classifying a sequence read as corresponding to two or more different types of pathogen reads. For example, a sequence read can align to a first bacterial reference genome and can also align to a second bacterial reference genome. Such alignment to more than one pathogen reference genome can result from a gene being homologous among different pathogens. The alignment and classification may be for different types of bacterial, archaeal, or viral reference genomes. In various embodiments, if the sequence read aligns to multiple pathogens, then the pathogen with the best alignment may be selected. If the sequence read aligns equally to multiple pathogens, then the sequence read may be discarded, apportioned to each pathogen, or assigned to a genus including the pathogens.

Method 3700 may include classifying the plurality of sequence reads to a plurality of types of pathogen reads. For example, a first sequence read of the plurality of sequence reads may align to a first archaeal reference genome, thereby classifying the sequence read as a first pathogen read, and a second sequence read of the plurality of sequence reads can align to a second archaeal reference genome, thereby classifying the sequence read as a second pathogen read. Any sequence read that aligns to a pathogen reference genome may be classified as a non-human read.

At block 3740, method 3700 may include determining a parameter based an amount of pathogen reads. The amount of pathogen reads may be a total of all reads that align to pathogen reference genomes (e.g., first pathogen reads, second pathogen reads), e.g., without double counting sequence reads that align to multiple pathogen reference genomes. In some embodiments, the amount of first pathogen reads may be the amount of sequence reads aligned to a specific pathogen reference genome. As examples, the parameter may be a raw count, a concentration, a fraction, or a percentage of first pathogen reads.

Method 3700 may include determining a second parameter based on a second amount of second pathogen reads for reads aligned to a different pathogen reference genome. As examples, the second parameter may be a raw count, a concentration, a fraction, or a percentage of second pathogen reads. The second parameter may be a parameter calculated in a corresponding method as the first parameter. Pathogen reference genomes may include genomes from *Halonotius, Thermococcus, Nitrosopumilus, Actinomyces*, or any pathogen described herein. In addition, pathogen reference genomes may exclude any genome from any pathogen described herein. Pathogen reference genomes may include or exclude bacterial genomes, viral genomes, and archaeal genomes.

Pathogen reference genomes may include a reference genome from at least one of *mycobacterium, halobacterium, actinomyces, corynebacterium*, or *candidatus*. The reference genome may include any one, two, three, or four of *mycobacterium, halobacterium, actinomyces, corynebacterium*, or *candidatus*.

At block 3750, method 3700 may include comparing the parameter to a cutoff value. If several types of parameters are determined based on amounts of different types of pathogen reads, each type of amount may be compared to one or more cutoff values. As an example, each parameter of the several types of parameters may be compared to a single cutoff value. In other examples, each type of parameter is compared to a cutoff value specific for the type of parameter. In some examples, a multidimensional point with coordinates specified by the different types of parameters may be compared against a cutoff value, which may be a line, plane, or higher-dimensional plane. The cutoff value or values may be determined from a first set of reference samples that have bladder cancer and a second set of control samples that do not have bladder cancer.

At block 3760, method 3700 may include determining a classification of a level of bladder cancer using the comparison. Method 3700 may include determining that the human has bladder cancer if the amount of first pathogen is above a cutoff value. If several parameters based on different types of amounts of pathogen reads are determined, determining that the human has bladder cancer may be if multiple parameters are greater than one or more cutoff values. In some embodiments, bladder cancer may be determined if a certain percentage (e.g, 50%, 60%, 70%, 80%, 90%, or 100%) of the parameters exceeds the one or more cutoff values. The severity of cancer may be determined by how high the parameters are compared to the cutoff values. In some embodiments, the severity of cancer may be determined by how many parameters are greater than one or more cutoff values.

Method 3700 may include any treatment for cancer described herein. In some instances, method 3700 may apply to a biological sample, not only a urine sample. In some instances, method 3700 may include determining a level of cancer, not just bladder cancer.

VIII. MATERIALS AND METHODS

Certain techniques are described below for certain results provided above. Such techniques used for one example can be used for other examples.

A. Sample Collection and Processing for Transplant Patients

For the transplant data, urine samples were collected from 11 renal transplant and two hematopoietic stem cell transplant (HSCT) patients who were clinically stable. Urine samples were also collected from a patient with a renal stone, and from five bladder cancer patients. Urine samples were collected during the morning clinic, or the morning before surgery, with early morning urine samples being avoided if possible. 30-50 mL of urine was collected in plain sterile bottles, stored at 4° C. and processed within one hour of collection as previously described (12,23). The cell free portion of the urine was isolated by centrifugation and filtering of the supernatant.

B. Library Preparation, Bisulfite Conversion and Massively Parallel DNA Sequencing DNA libraries were prepared with up to 500 ng of urinary cfDNA using the KAPA HTP Library Preparation Kit (Kapa Biosystems) according to the manufacturer's instructions (7). Bisulfite and non-bisulfite DNA sequencing were performed as previously described (24,25), using an Illumina HiSeq 2500 sequencer using the 75 bp paired end mode. After base calling and quality control, the data were then processed by the methylation data analysis pipeline Methy-Pipe (26).

Up to 500 ng of urinary cfDNA were used for library preparation. DNA libraries were prepared using the KAPA HTP Library Preparation Kit (Kapa Biosystems) according to the manufacturer's instructions (7). Bisulfite and non-bisulfite DNA sequencing were performed as previously described (24,25). Non-bisulfite sequencing was used for size profile analysis only when there was insufficient DNA for bisulfite sequencing. DNA libraries were sequenced using an Illumina HiSeq 2500 sequencer using the 75 bp paired end mode. After base calling, adapter sequences and low quality bases (i.e., quality score <5) were removed. The trimmed reads in FASTQ format were then processed by the methylation data analysis pipeline Methy-Pipe (26). Using one lane of sequencing per urine sample, we obtained a median of 80 million unique, non-duplicated reads mapped to the human reference genome.

C. Extraction and Quantification

For extraction and quantification of urinary cfDNA, urinary cfDNA was extracted and quantified as previously described (11, 12, 23). 30-50 mL of urine for most samples and up to 250 mL were required for in vitro incubation experiments. Briefly, fresh urine was collected in plain sterile bottles, and an aliquot was tested using the Siemens Multistix 10SG system and assayed for creatinine concentration using the Roche Cobas 8000. For the remaining urine sample, 0.5 mol/L EDTA at pH 8 (Invitrogen) was added for a final EDTA concentration of 10 mmol/L to inhibit nuclease activity (9). EDTA corresponds to ethylenediaminetetraacetic acid.

Urine was then centrifuged at 4° C. for 10 minutes and the supernatant was filtered through a 0.45-μm filter (Milex-GV; Millipore) to isolate the cell-free component. The cell-free urine was then either stored at −80° C. or extracted immediately. For every 10 mL of processed urine, we added 15 mL of 6 mol/L guanidine thiocyanate (Sigma-Aldrich) and 1 mL of resin (Wizard Plus Minipreps DNA Purification System; Promega) and the mixture was incubated at room temperature for 2 hours. The resin-DNA complex was then isolated, washed, and eluted using the Wizard Plus Minipreps DNA Purification System as per the manufacturer's instructions. Approximately 100 μL was used in the elution of urinary cfDNA for every 10 mL of urine collected.

Extracted cfDNA was quantified using real time qPCR with a 62 bp amplicon targeting the LEP gene (11). The absolute DNA concentration was determined using an 11-point DNA standard which ranged from 1.25 to 4000 GE/uL, and all urinary cfDNA concentrations are expressed in terms of GE/mL of urine.

Extraction and quantification of genomic DNA from peripheral blood leucocytes and tissue can be performed as follows. Buffy coat samples were processed using the Qiagen DNA Blood Mini Kit and tissue samples were processed using the Qiagen DNA Mini Kit as per manufacturers protocol.

D. Determination of Donor and Recipient Specific Genotypes Using SNP Arrays

For all renal transplant and HSCT patients, ~2.5 million donor and recipient SNPs were interrogated using the Illumina Omni 2.5 SNP array, according to manufacturer's protocols. Donor and recipient germline DNA was obtained either from buffy coat, buccal swab or renal tissue. This allowed us to identify donor and recipient specific SNPs for each transplant case. Knowledge of donor and recipient specific alleles was used in conjunction with massively parallel sequencing results which allowed us to accurately ascertain the proportion of donor and recipient specific cfDNA fragments in urine.

E. Identification of Differentially Methylated Regions as Methylation Markers for Urinary DNA Tissue Mapping.

Genomewide bisulfite sequencing data from different human tissues were used to construct a reference methylome for methylation deconvolution. We hypothesized that the major contributors to urinary cfDNA in normal samples would be blood cells (the major constituent of plasma cfDNA, and could also be released in the post renal system), the kidney, and the urothelium which lined the entire urinary tract. Whole genome bisulfite sequencing data for neutrophils, B-cells and T-cells were obtained from publically available resources (Human Epigenome Atlas, genboree-.org/epigenomeatlas/index.rhtml), (28). When we commenced this study, no genomewide methylation data was available for the kidney or urothelium; and thus we constructed our own reference methylome by obtaining tissue from a cadaveric renal transplant case and the adjacent normal tissue from patients undergoing a nephro-uretectomy and radical cystectomy. The kidney reference was compiled using bisulfite sequcing data from cortical and medullary kidney tissues obtained from 6 patients and sequenced to 35× haploid genome coverage. The urothelial reference comprises of urothelium obtained from the ureter and bladder of 6 patients sequenced to 40× haploid genome coverage. The bladder cancer reference was based on bladder tumor obtained during radical cystectomy and sequenced to 8.5× haploid genome coverage.

Methylation markers were selected as previously described (22). Autosomal CpG islands and shores were subdivided into non-overlapping 500 bp units and the methylation density of each unit was determined for each reference tissue. Differentially methylated regions were used to identify type I and type II markers. Type I markers referred to any genomic loci with methylation densities that were 3 SDs higher or lower in one tissue compared with the mean level of all other reference tissues. Type II markers were genomic loci that demonstrated highly variable methylation densities across all tissue types. A locus was considered highly variable when (A) the methylation density of the most hypermethylated tissue was at least 20% higher than that of the most hypomethylated one; and (B) the SD of the methylation densities across all tissue types when divided by the mean methylation density (i.e., the coefficient of variation) of the group was at least 0.25.

F. Methylation Deconvolution for the Determination of the Proportional Contribution of Different Tissues in Urinary cfDNA An aim of methylation deconvolution was to determine the proportional contribution of each tissue in urinary cfDNA. Methylation deconvolution was conducted as described by Sun et al(22). Briefly, the methylation density observed at a particular marker was influenced by the proportional contribution from each tissue, and the methylation density of that marker in each tissue.

Quadratic programming (39) was used to solve the simultaneous equations. A matrix was compiled including the panel of tissues and their corresponding methylation densities for each methylation marker on the combined list of type I and type II markers (a total of 19,418 markers). The reference methylome consisted of the kidney, urothelium, neutrophils, and lymphocytes and the proportional contribution from all tissues would sum to 100%. These tissue types were selected as each of them, apart from the urothelium, could be validated by renal transplant or HSCT. When assessing the pre and post-operative urine samples of bladder cancer patients, methylation markers derived from the bladder cancer and small intestines methylome was added to the reference set.

G. Identification of Hypomethylation and Copy Number Aberrations in Urinary cfDNA The genomewide methylation density and copy number by 1 Mb bins was determined using the urinary cfDNA data from 8 normal controls. A significant increase or decrease in methylation density or copy number was defined as a z-score of more than 3 compared with the average of normal controls. Global methylation density and copy number changes were represented using circos plots(35).

IX. EXAMPLE SYSTEMS

Figure 38:
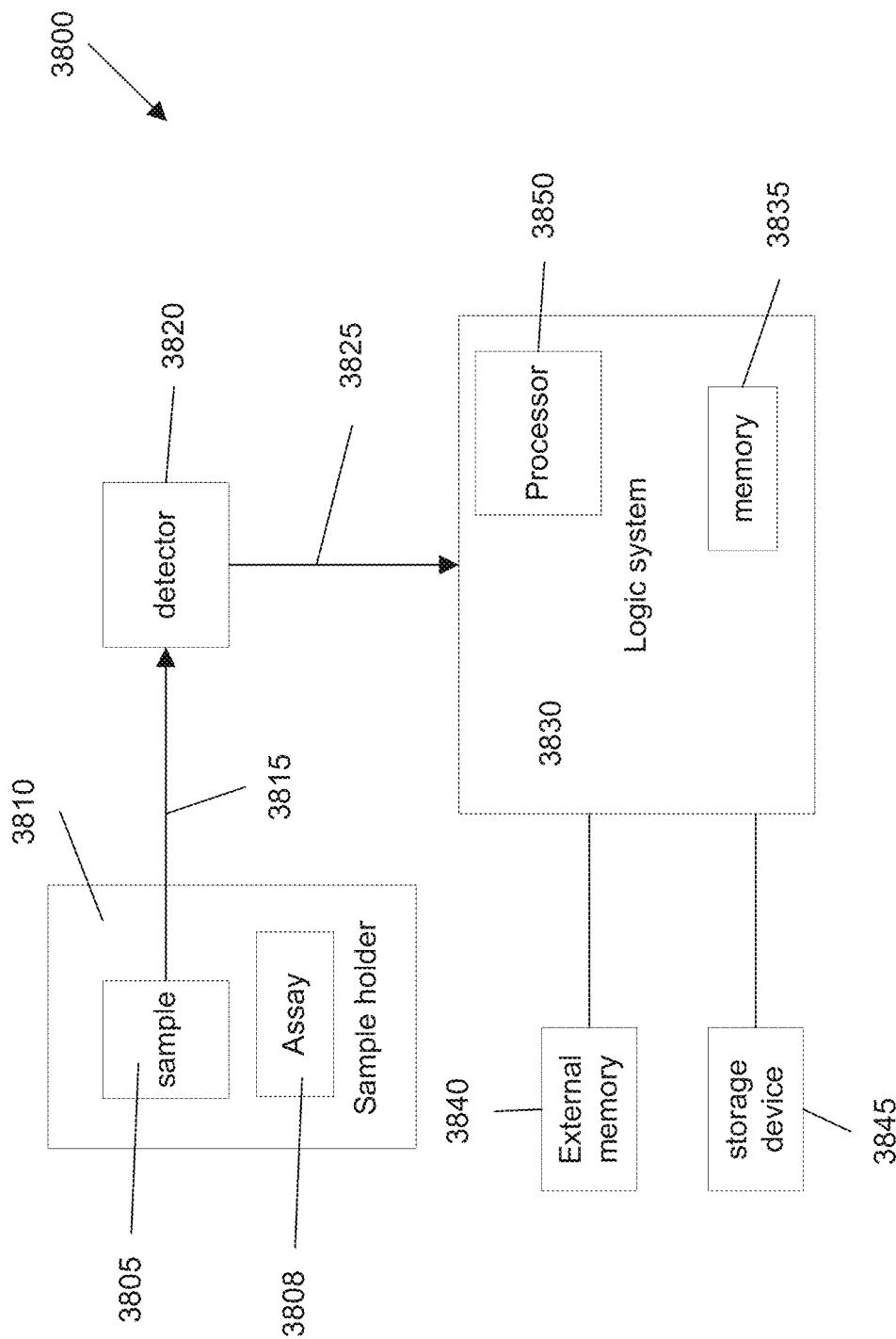
FIG. 38 illustrates a system 3800 according to an embodiment of the present invention.

FIG. 38 illustrates a system 3800 according to an embodiment of the present invention. The system as shown includes a sample 3805, such as cell-free DNA molecules within a sample holder 3810, where sample 3805 can be contacted with an assay 3808 to provide a signal of a physical characteristic 3815. An example of a sample holder can be a flow cell that includes probes and/or primers of an assay or a tube through which a droplet moves (with the droplet including the assay). Physical characteristic 3815, such as a fluorescence intensity value, from the sample is detected by detector 3820. Detector can take a measurement at intervals (e.g., periodic intervals) to obtain data points that make up a data signal. In one embodiment, an analog to digital converter converts an analog signal from the detector into digital form at a plurality of times. A data signal 3825 is sent from detector 3820 to logic system 3830. Data signal 3825 may be stored in a local memory 3835, an external memory 3840, or a storage device 3845.

Logic system 3830 may be, or may include, a computer system, ASIC, microprocessor, etc. It may also include or be coupled with a display (e.g., monitor, LED display, etc.) and a user input device (e.g., mouse, keyboard, buttons, etc.). Logic system 3830 and the other components may be part of a stand-alone or network connected computer system, or they may be directly attached to or incorporated in a thermal cycler device. Logic system 3830 may also include optimization software that executes in a processor 3850.

Figure 39:
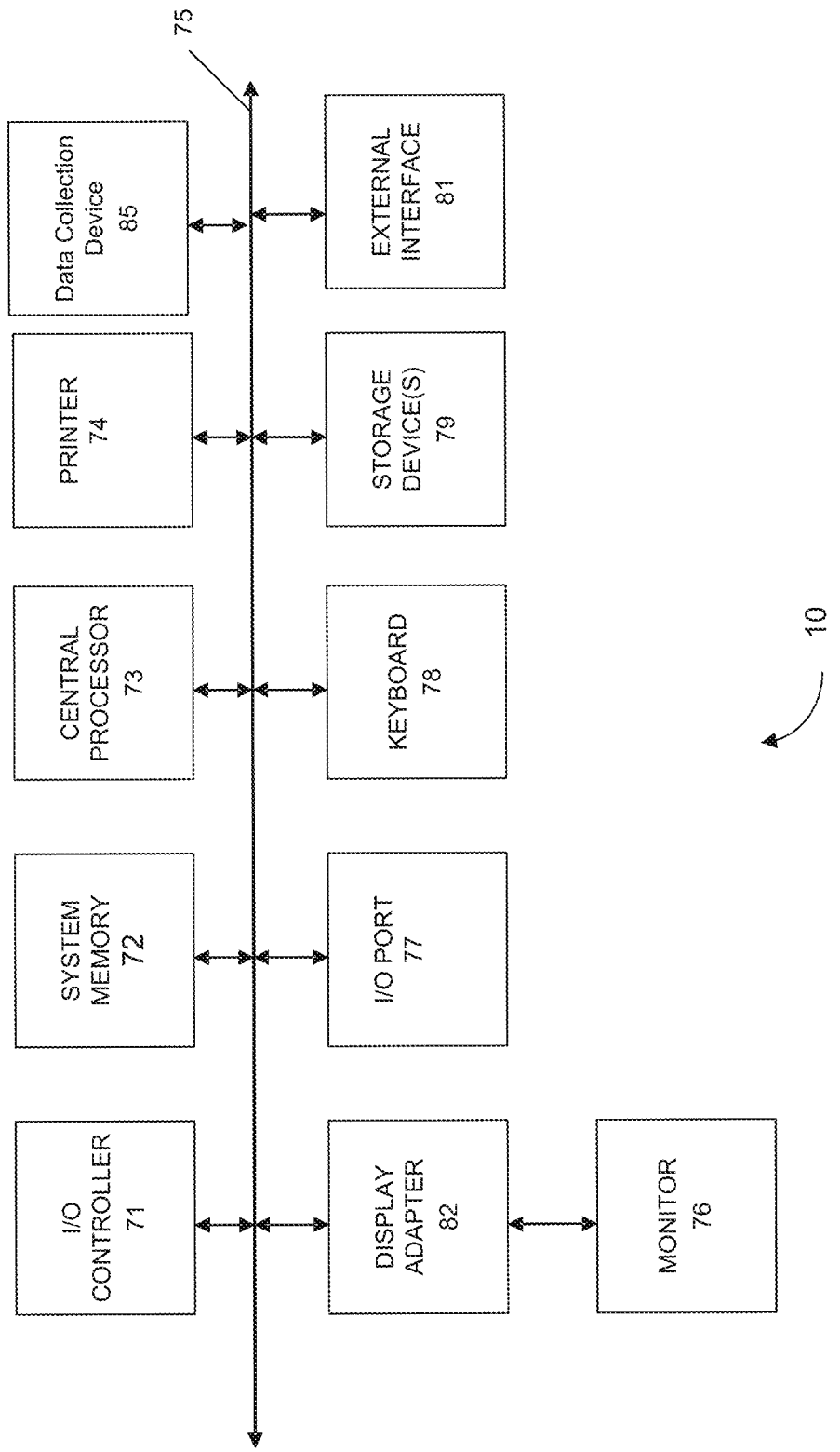
FIG. 39 shows a block diagram of an example computer system usable with system and methods according to embodiments of the present invention.

Any of the computer systems mentioned herein may utilize any suitable number of subsystems. Examples of such subsystems are shown in FIG. 39 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 39 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

X. REFERENCES

1. Stroun M, Maurice P, Vasioukhin V, Lyautey J, Lederrey C, Lefort F, et al. The origin and mechanism of circulating DNA. Ann N Y Acad Sci 2000; 906:161-8.
2. Lo Y M, Corbetta N, Chamberlain P F, Rai V, Sargent I L, Redman C W, et al. Presence of fetal DNA in maternal plasma and serum Lancet 1997; 350:485-7.
3. Chen X Q, Stroun M, Magnenat J L, Nicod L P, Kurt A M, Lyautey J, et al. Microsatellite alterations in plasma DNA of small cell lung cancer patients Nat Med 1996; 2:1033-5.
4. Lo Y M, Tein M S, Pang C C, Yeung C K, Tong K L, Hjelm N M Presence of donor-specific DNA in plasma of kidney and liver-transplant recipients. Lancet 1998; 351:1329-30.
5. Chiu R W K, Chan K C A, Gao Y, Lau V Y M, Zheng W, Leung T Y, et al. Noninvasive prenatal diagnosis of fetal chromosomal aneuploidy by massively parallel genomic sequencing of DNA in maternal plasma. Proc Natl Acad Sci USA 2008; 105:20458-63.
6. Leary R J, Sausen M, Kinde I, Papadopoulos N, Carpten J D, Craig D, et al. Detection of chromosomal alterations in the circulation of cancer patients with whole-genome sequencing. Sci Transl Med 2012; 4:162ra154.
7. Chan K C A, Jiang P, Chan C W M, Sun K, Wong J, Hui E P, et al. Noninvasive detection of cancer-associated genome-wide hypomethylation and copy number aberrations by plasma DNA bisulfite sequencing. Proc Natl Acad Sci USA 2013; 110:18761-8.
8. De Vlaminck I, Valantine H A, Snyder T M, Strehl C, Cohen G, Luikart H, et al. Circulating cell-free DNA enables noninvasive diagnosis of heart transplant rejection. Sci Transl Med 2014; 6:241ra77.
9. Botezatu I, Serdyuk O, Potapova G, Shelepov V, Alechina R, Molyaka Y, et al. Genetic analysis of DNA excreted in urine: a new approach for detecting specific genomic DNA sequences from cells dying in an organism. Clin Chem 2000; 46:1078-84.
10. Al-Yatama M K, Mustafa A S, Ali S, Abraham S, Khan Z, Khaj a N. Detection of Y chromosome-specific DNA in the plasma and urine of pregnant women using nested polymerase chain reaction. Prenat Diagn 2001; 21:399-402.
11. Tsui N B Y, Jiang P, Chow K C K, Su X, Leung T Y, Sun H, et al. High resolution size analysis of fetal DNA in the urine of pregnant women by paired-end massively parallel sequencing. PLoS One 2012; 7:e48319.
12. Hung E C W, Shing T K F, Chim S S C, Yeung P C, Chan R W Y, Chik K W, et al. Presence of donor-derived DNA and cells in the urine of sex-mismatched hematopoietic stem cell transplant recipients: implication for the transrenal hypothesis. Clin Chem 2009; 55:715-22.
13. Su Y-H, Wang M, Brenner D E, Norton P A, Block T M. Detection of mutated K-ras DNA in urine, plasma, and serum of patients with colorectal carcinoma or adenomatous polyps. Ann N Y Acad Sci 2008; 1137:197-206.
14. Chan K C A, Leung S F, Yeung S W, Chan A T C, Lo Y M D. Quantitative analysis of the transrenal excretion of circulating EBV DNA in nasopharyngeal carcinoma patients. Clin Cancer Res 2008; 14:4809-13.
15. Zhang J, Tong K-L, Li P K T, Chan A Y W, Yeung C-K, Pang C C P, et al. Presence of Donor- and Recipient-derived DNA in Cell-free Urine Samples of Renal Transplantation Recipients: Urinary DNA Chimerism. Clin Chem 1999; 45:1741-6.
16. Szarvas T, Kovalszky I, Bedi K, Szendroi A, Majoros A, Riesz P, et al. Deletion analysis of tumor and urinary DNA to detect bladder cancer: urine supernatant versus urine sediment. Oncol Rep 2007; 18:405-9.
17. Birkenkamp-Demtroder K, Nordentoft I, Christensen E, Hoyer S, Reinert T, Vang S, et al. Genomic Alterations in Liquid Biopsies from Patients with Bladder Cancer. Eur Urol 2016; 70:75-82.
18. Li Y, Zhong X Y, Kang A, Troeger C, Holzgreve W, Hahn S. Inability to detect cell free fetal DNA in the urine of normal pregnant women nor in those affected by preeclampsia associated HELLP syndrome. J Soc Gynecol Investig. 2003; 10:503-8.
19. Fernandez A F, Assenov Y, Martin-Subero J I, Balint B, Siebert R, Taniguchi H, et al. A DNA methylation fingerprint of 1628 human samples. Genome Res 2012; 22:407-19.
20. Consortium R E, Kundaje A, Meuleman W, Ernst J, Bilenky M, Yen A, et al. Integrative analysis of 111 reference human epigenomes. Nature 2015; 518:317-30.
21. Houseman E A, Accomando W P, Koestler D C, Christensen B C, Marsit C J, Nelson H H, et al. DNA methylation arrays as surrogate measures of cell mixture distribution. BMC Bioinformatics 2012; 13:86.
22. Sun K, Jiang P, Chan K C A, Wong J, Cheng Y K Y, Liang R H S, et al. Plasma DNA tissue mapping by genome-wide methylation sequencing for noninvasive prenatal, cancer, and transplantation assessments. Proc Natl Acad Sci USA 2015; 112:E5503-12.
23. Yu S C Y, Lee S W Y, Jiang P, Leung T Y, Chan K C A, Chiu R W K, et al. High-resolution profiling of fetal DNA clearance from maternal plasma by massively parallel sequencing. Clin Chem 2013; 59:1228-37.
24. Chan K C A, Jiang P, Zheng Y W L, Liao G J W, Sun H, Wong J, et al. Cancer genome scanning in plasma: detection of tumor-associated copy number aberrations, single-nucleotide variants, and tumoral heterogeneity by massively parallel sequencing. Clin Chem 2013; 59:211-24.
25. Lun F M F, Chiu R W K, Sun K, Leung T Y, Jiang P, Chan K C A, et al. Noninvasive prenatal methylomic analysis by genomewide bisulfite sequencing of maternal plasma DNA. Clin Chem 2013; 59:1583-94.
26. Jiang P, Sun K, Lun F M F, Guo A M, Wang H, Chan K C A, et al. Methy-Pipe: an integrated bioinformatics pipeline for whole genome bisulfite sequencing data analysis. PLoS One 2014; 9:e100360.
27. Lui Y Y N, Chik K W, Chiu R W K, Ho C Y, Lam C W K, Lo Y M D. Predominant hematopoietic origin of cell-free dna in plasma and serum after sex-mismatched bone marrow transplantation. Clin Chem 2002; 48:421-7.
28. Hodges E, Molaro A, Dos Santos C O, Thekkat P, Song Q, Uren P J, et al. Directional DNA methylation changes and complex intermediate states accompany lineage specificity in the adult hematopoietic compartment. Mol Cell 2011; 44:17-28.
29. Ito K, Minamiura N, Yamamoto T. Human urine DNase I: immunological identity with human pancreatic DNase I, and enzymic and proteochemical properties of the enzyme. J Biochem 1984; 95:1399-406.
30. Nadano D, Yasuda T, Kishi K. Measurement of deoxyribonuclease I activity in human tissues and body fluids by a single radial enzyme-diffusion method. Clin Chem 1993; 39:448-52.
31. Jiang P, Chan C W M, Chan K C A, Cheng S H, Wong J, Wong V W-S, et al. Lengthening and shortening of plasma DNA in hepatocellular carcinoma patients. Proc Natl Acad Sci USA 2015; 112:E1317-25.
32. Underhill H R, Kitzman J O, Hellwig S, Welker N C, Daza R, Baker D N, et al. Fragment Length of Circulating Tumor DNA. PLoS Genet 2016; 12:e1006162.
33. Feinberg A P, Vogelstein B. Hypomethylation distinguishes genes of some human cancers from their normal counterparts. Nature 1983; 301:89-92.
34. Beroukhim R, Mermel C H, Porter D, Wei G, Raychaudhuri S, Donovan J, et al. The landscape of somatic copy-number alteration across human cancers. Nature 2010; 463:899-905.
35. Krzywinski M, Schein J, Birol I, Connors J, Gascoyne R, Horsman D, et al. Circos: an information aesthetic for comparative genomics. Genome Res 2009; 19:1639-45.
36. Lo Y M D, Chan K C A, Sun H, Chen E Z, Jiang P, Lun F M F, et al. Maternal plasma DNA sequencing reveals the genome-wide genetic and mutational profile of the fetus. Sci Transl Med 2010; 2:61ra91.
37. Snyder M W, Kircher M, Hill A J, Daza R M, Shendure J. Cell-free DNA Comprises an In Vivo Nucleosome Footprint that Informs Its Tissues-Of-Origin. Cell 2016; 164:57-68.
38. The Cancer Genome Atlas Research Network. Comprehensive molecular characterization of urothelial bladder carcinoma. Nature 2014; 507:315-22.
39. Meersche K Van den, Soetaert K, Oevelen D Van. xsample( ): An R Function for Sampling Linear Inverse Problems. J Stat Softw 2009; 30:1-15.

What is claimed is:

1. A method of analyzing a biological sample of an organism, the biological sample being a urine sample, the biological sample including a mixture of cell-free DNA molecules from a plurality of tissues types, the method comprising:
identifying N genomic sites, N being an integer greater than or equal to 10;
for each of M tissue types:
obtaining N tissue-specific methylation levels at the N genomic sites, N being greater than or equal to M, wherein the tissue-specific methylation levels form a matrix A of dimensions N by M, wherein a first tissue type of the M tissue types corresponds to a first diseased tissue type corresponding to a first disease of a first organ, wherein the first diseased tissue type corresponds to cancerous urothelium cells, wherein a second tissue type of the M tissue types corresponds to normal urothelium, and wherein a third tissue type of the M tissue types corresponds to a second diseased tissue type corresponding to a second disease of the first organ;
analyzing, by a computer system, a plurality of cell-free DNA molecules from the biological sample, the plurality of cell-free DNA molecules being at least 1,000 cell-free DNA molecules, wherein analyzing a cell-free DNA molecule includes:
identifying a location of the cell-free DNA molecule in a reference genome corresponding to the organism;
identifying a set of the plurality of cell-free DNA molecules that are each located at any one of the N genomic sites;

measuring N mixture methylation levels at the N genomic sites using the set of the plurality of cell-free DNA molecules;

determining, by the computer system, a first fractional contribution of the first diseased tissue type in the mixture using the N mixture methylation levels and the N tissue-specific methylation levels of each of the M tissue types; and using the first fractional contribution of the first diseased tissue type to determine a level of the first disease for the first organ in the organism.

2. The method of claim 1, the method further comprising:

determining, by the computer system, a second fractional contribution of the second diseased tissue type in the mixture using the N mixture methylation levels and the N tissue-specific methylation levels of each of the M tissue types; and using the second fractional contribution of the second diseased tissue type to determine a level of the second disease for the first organ in the organism.

3. The method of claim 1, wherein a fourth tissue type of the M tissue types corresponds to a third diseased tissue type corresponding to a third disease of a second organ, the method further comprising:

determining, by the computer system, a second fractional contribution of the third diseased tissue type in the mixture using the N mixture methylation levels and the N tissue-specific methylation levels of each of the M tissue types; and using the second fractional contribution of the third diseased tissue type to determine a level of the third disease for the second organ in the organism.

4. The method of claim 1, wherein the first organ is a bladder.

5. The method of claim 4, wherein the level of the first disease is that the first disease exists.

6. The method of claim 5, further comprising treating the organism for bladder cancer using chemotherapy.

7. The method of claim 1, wherein the level of the first disease is that the first disease exists.

8. The method of claim 7, further comprising treating the organism for cancer using chemotherapy, drugs, diet, or surgery.

9. The method of claim 8, wherein treating the organism uses chemotherapy or surgery.

10. The method of claim 1, the method further comprising:

preparing the urine sample by adding ethylenediaminetetraacetic acid (EDTA).

11. The method of claim 1, further comprising determining a proportional contribution of cell-free DNA and cellular DNA in the biological sample.

12. The method of claim 1, wherein the N genomic sites comprise sites that have less than a threshold amount of inter-individual variation.

13. The method of claim 1, wherein the M tissue types comprise kidney, neutrophils, B-cells, and T-cells.

14. The method of claim 1, further comprising:

receiving the biological sample, wherein:

analyzing the plurality of cell-free DNA molecules comprises:

sequencing the cell-free DNA molecules to obtain sequence reads, and aligning the sequence reads to the reference genome to identify the location of the cell-free DNA molecules;

measuring N mixture methylation levels comprises:

using treatment with bisulfite, methylation immunoprecipitation, treatment with a methylation-binding protein, or treatment with a methylation-sensitive restrictive enzyme.

15. The method of claim 1, wherein a fourth tissue type of the M tissue types corresponds to a third diseased tissue type corresponding to a first disease of a second organ, wherein the second organ is not the first organ.

16. The method of claim 15, wherein the second organ is the kidney, and the first disease of the second organ is glomerulonephritis or nephrotic syndrome.

17. The method of claim 1, wherein using the first fractional contribution of the first diseased tissue type to determine the level of the first diseased tissue type for the first organ in the organism comprises comparing the first fractional contribution to a cutoff value.

18. The method of claim 1, wherein the level of the first disease is that the first disease is muscle invasive.

19. A system, comprising:

a detector, wherein the detector is configured to measure a physical characteristic of a plurality of cell-free DNA molecules from a biological sample of an organism, the biological sample being a urine sample, the biological sample including a mixture of cell-free DNA molecules from a plurality of tissues types, the plurality of cell-free DNA molecules being at least 1,000 cell-free DNA molecules, wherein the detector is further configured to send measurement data to a logic system; and the logic system, wherein the logic system is configured to:

identify N genomic sites, N being an integer greater than or equal to 10;

obtain N tissue-specific methylation levels for each of M tissue types at the N genomic sites, N being greater than or equal to M, wherein:

the tissue-specific methylation levels form a matrix A of dimensions N by M, a first tissue type of the M tissue types corresponds to a first diseased tissue type corresponding to a first disease of a first organ, the first tissue type corresponds to cancerous urothelium cells, a second tissue type of the M tissue types corresponds to normal urothelium, and a third tissue type of the M tissue types corresponds to a second diseased tissue type corresponding to a second disease of the first organ;

analyze the plurality of cell-free DNA molecules, wherein the logic system is further configured to identify a location of the cell-free DNA molecule in a reference genome corresponding to the organism for each cell-free DNA molecule of the plurality of cell-free DNA molecules;

identify a set of the plurality of cell-free DNA molecules that are each located at any one of the N genomic sites;

determine, using the measurement data, N mixture methylation levels at the N genomic sites using the set of the plurality of cell-free DNA molecules;

determine a first fractional contribution of the first diseased tissue type in the mixture using the N mixture methylation levels and the N tissue-specific methylation levels of each of the M tissue types;

determine a level of the first disease for the first organ in the organism using the first fractional contribution; and output the level of the first disease to a display.

20. The system of claim 19, further comprising:
an assay device configured to provide a signal of the physical characteristic, wherein:
the detector detects the signal to measure the physical characteristic.

21. The system of claim 20, wherein the assay device and the detector are part of a methylation-aware sequencer.

22. The system of claim 20, further comprising:
a sample holder.

23. The system of claim 22, wherein the sample holder comprises probes or primers.

24. The system of claim 19, wherein the physical characteristic is fluorescence intensity.

* * * * *